US012723049B2

(12) United States Patent
Arachchilage et al.

(10) Patent No.: US 12,723,049 B2
(45) Date of Patent: Sep. 1, 2026

(54) METHODS FOR TREATING SPINOCEREBELLAR ATAXIA TYPE 3

(71) Applicant: PTC Therapeutics, Inc., Warren, NJ (US)

(72) Inventors: Gayan Mirihana Arachchilage, South Plainfield, NJ (US); Michael A. Arnold, South Plainfield, NJ (US); Scott Barraza, South Plainfield, NJ (US); Anuradha Bhattacharyya, South Plainfield, NJ (US); Gary Mitchell Karp, South Plainfield, NJ (US)

(73) Assignee: PTC Therapeutics, Inc., Warren, NJ (US)

( * ) Notice: Subject to any disclaimer, the term of this patent is extended or adjusted under 35 U.S.C. 154(b) by 364 days.

(21) Appl. No.: 18/264,189

(22) PCT Filed: Feb. 2, 2022

(86) PCT No.: PCT/US2022/014934

§ 371 (c)(1),
(2) Date: Aug. 3, 2023

(87) PCT Pub. No.: WO2022/169868

PCT Pub. Date: Aug. 11, 2022

(65) Prior Publication Data

US 2024/0043444 A1 Feb. 8, 2024

Related U.S. Application Data

(60) Provisional application No. 63/146,151, filed on Feb. 5, 2021.

(51) Int. Cl.
*C07D 495/04* (2006.01)
*A61P 21/00* (2006.01)

(52) U.S. Cl.
CPC ............ *C07D 495/04* (2013.01); *A61P 21/00* (2018.01); *A61K 2121/00* (2013.01); *C07B 2200/07* (2013.01)

(58) Field of Classification Search
CPC ...... C07D 495/04; A61P 21/00; A61K 31/519
See application file for complete search history.

(56) References Cited

U.S. PATENT DOCUMENTS

| | | | |
|---|---|---|---|
| 3,475,429 | A | 10/1969 | Woitun et al. |
| 5,532,257 | A | 7/1996 | Hase et al. |
| 5,654,307 | A | 8/1997 | Bridges et al. |
| 6,211,195 | B1 | 4/2001 | Webb et al. |
| 6,492,383 | B1 | 12/2002 | Munchhof et al. |
| 2004/0138251 | A1 | 7/2004 | Boschelli et al. |
| 2012/0053173 | A1 | 3/2012 | Banno et al. |
| 2013/0209549 | A1 | 8/2013 | Dickey |
| 2013/0317045 | A1 | 11/2013 | Hadd et al. |
| 2014/0005183 | A1 | 1/2014 | Galatsis et al. |
| 2014/0323544 | A1 | 10/2014 | Bestwick et al. |
| 2015/0344497 | A1 | 12/2015 | Zhou et al. |
| 2016/0002273 | A1 | 1/2016 | Blum et al. |
| 2018/0118748 | A1 | 5/2018 | Slaugenhaupt et al. |
| 2018/0258425 | A1 | 9/2018 | Rigo et al. |
| 2019/0000844 | A1 | 1/2019 | Babu et al. |
| 2020/0239940 | A1 | 7/2020 | Guo et al. |
| 2022/0056043 | A1 | 2/2022 | Li et al. |
| 2024/0024490 | A1 | 1/2024 | Choudhary et al. |

FOREIGN PATENT DOCUMENTS

| | | | |
|---|---|---|---|
| CA | 3082907 | A1 | 5/2019 |
| CL | 202102104 | | 4/2022 |
| CN | 103242341 | A | 8/2013 |
| CN | 110312528 | A | 10/2019 |
| CO | NC20170011017 | A2 | 3/2018 |
| CO | NC20180001425 | A2 | 5/2018 |
| CO | NC20180013803 | A2 | 1/2019 |
| CO | NC20210008895 | A2 | 7/2021 |
| EP | 2014663 | A1 | 1/2009 |
| EP | 3020829 | A1 | 5/2016 |
| EP | 3828829 | A1 | 6/2021 |
| JP | 2009007341 | A | 1/2009 |
| KR | 102390370 | B1 | 4/2022 |
| WO | 2004/065392 | A1 | 8/2004 |
| WO | 2005007083 | A2 | 1/2005 |
| WO | 2009085226 | A2 | 7/2009 |
| WO | 2012/044993 | A1 | 4/2012 |
| WO | 2013026516 | A1 | 2/2013 |
| WO | 2015053624 | A2 | 4/2015 |
| WO | 2016115434 | A1 | 7/2016 |
| WO | 2017053781 | A1 | 3/2017 |
| WO | 2018075937 | A1 | 4/2018 |
| WO | 2018134685 | A2 | 7/2018 |
| WO | 2020/167628 | | 8/2020 |
| WO | 2020167624 | A1 | 8/2020 |
| WO | 2020245233 | A1 | 12/2020 |
| WO | 2021/118929 | | 6/2021 |

(Continued)

OTHER PUBLICATIONS

International Search Report for PCT/US2022/075966 date mailed Jan. 19, 2023.
Written Opinion for PCT/US2022/075966 date mailed Jan. 19, 2023.
Pubchem, SID 274791846, Modify Date: Nov. 21, 2016, Available: Dec. 18, 2015.
International Search Report for PCT/US2022/2075967 date mailed Jan. 19, 2023.
Written Opinion for PCT/US2022/075967 date mailed Jan. 19, 2023.
Pubchem, SID 365025105, Available Date: May 25, 2018.
Pubchem, SID 439055238, Available Date: Dec. 19, 2020.
International Search Report for PCT/US2022/075969 date mailed Jan. 19, 2023.
Written Opinion for PCT/US2022/075969 date mailed Jan. 19, 2023.
Pubchem, SID 377008396, Available Date: Dec. 4, 2018.

(Continued)

*Primary Examiner* — Susanna Moore
(74) *Attorney, Agent, or Firm* — Hoffmann & Baron, LLP

(57) ABSTRACT

The present description relates to methods of treating spinocerebellar ataxia type 3 (SCA3) using substituted thieno [3,2-d]pyrimidine compounds, forms, and pharmaceutical compositions thereof.

16 Claims, No Drawings

Specification includes a Sequence Listing.

(56) References Cited

FOREIGN PATENT DOCUMENTS

| | | | |
|---|---|---|---|
| WO | 2021142351 | A1 | 7/2021 |
| WO | 2022169864 | A1 | 8/2022 |
| WO | 2022169866 | A1 | 8/2022 |
| WO | 2022169868 | A1 | 8/2022 |
| WO | 2023039368 | A1 | 3/2023 |
| WO | 2023039369 | A1 | 3/2023 |
| WO | 2023039370 | A1 | 3/2023 |
| WO | 2023081858 | A1 | 5/2023 |
| WO | 2023250316 | A1 | 12/2023 |

OTHER PUBLICATIONS

International Search Report for PCT/US2020/017423 date mailed May 12, 2020.
Written Opinion for PCT/US2020/017423 date mailed May 12, 2020.
International Search Report for PCT/US2020/017430 date mailed May 19, 2020.
Written Opinion for PCT/US2020/017430 date mailed May 19, 2020.
International Search Report for PCT/US2020/063612 date mailed Mar. 1, 2021.
Written Opinion for PCT/US2020/063612 date mailed Mar. 1, 2021.
Panchal et al., "Evaluation of basic, heterocyclic ring systems as templates for use as potassium competitive acid blockers (pCABs)", Bioorganic & Medicinal Chemistry Letters, vol. 19, No. 23, Dec. 1, 2009 (Dec. 1, 2009), available online Jul. 4, 2009, pp. 6813-6817, XP026736113.
Database Registry [Online] Chemical Abstracts Service, Columbus, Ohio, US; May 2, 2017 (May 2, 2017), XP002802124, Database accession No. 2094356-55-3, 7-methyl-N-[[1-methyl-3-(trifluoromethyl)-thieno[3,2-d]pyrimidin-4-amine.
International Search Report for PCT/US2022/014929 date mailed Jun. 21, 2022.
Written Opinion for PCT/US2022/014929 date mailed Jun. 21, 2022.
International Search Report for PCT/US2022/014932 date mailed Jun. 15, 2022.
Written Opinion for PCT/US2022/014932 date mailed Jun. 15, 2022.
International Search Report for PCT/US2022/014934 date mailed Jun. 15, 2022.
Written Opinion for PCT/US2022/014934 date mailed Jun. 15, 2022.
Vippagunta et al., "Crystalline solids," Advanced Drug Delivery Reviews, vol. 48, Issue 1, May 16, 2001, pp. 3-26.
V. Craig Jordan, "Tamoxifen: A Most Unlikely Pioneering Medicine," Nature Reviews: Drug Discovery, vol. 2 (Mar. 2003) pp. 205-213.
Xiong Shu-Hua et al., "Diagnosis and Treatment Update on Autoimmune Autonomic Gangliopathy," pp. 690-693 A Chinese journal of clinical neuroscience No. 20 vol. 6 Dec. 31, 2012.
CAS Database Registry STN No. 1349454-03-0, entered on Dec. 6, 2011.
"Chemical Encyclopedia", scientific publishing house "Great Russian Encyclopedia," Moskva, vol. 4, pp. 499-501, 1995.
CAS Database Registry STN No. 2167522-70-3, entered on Jan. 1, 2018.
CAS Database Registry STN No. 2021176-84-9, entered on Oct. 28, 2016.
CAS Database Registry STN No. 1881342-47-7, entered on Mar. 8, 2016.
CAS Database Registry STN No. 1878819-09-0, entered on Mar. 3, 2016.
CAS Database Registry STN No. 1876870-61-9, entered on Mar. 1, 2016.
CAS Database Registry STN No. 1876583-64-0, entered on Mar. 1, 2016.
CAS Database Registry STN No. 1876399-06-2, entered on Feb. 29, 2016.
CAS Database Registry STN No. 1874906-94-1, entered on Feb. 26, 2016.
CAS Database Registry STN No. 1870492-22-0, entered on Feb. 19, 2016.
CAS Database Registry STN No. 1858986-81-8, entered on Feb. 3, 2016.
CAS Database Registry STN No. 1858871-72-3, entered on Feb. 3, 2016.
CAS Database Registry STN No. 2302366-29-4, entered on Apr. 7, 2016.
CAS Database Registry STN No. 2300574-14-3, entered on Apr. 4, 2016.
CAS Database Registry STN No. 2299694-59-8, entered on Apr. 3, 2019.
CAS Database Registry STN No. 2299370-15-1, entered on Apr. 3, 2019.
CAS Database Registry STN No. 2295625-99-7, entered on Mar. 28, 2019.
CAS Database Registry STN No. 2295625-98-6, entered on Mar. 28, 2019.
CAS Database Registry STN No. 2294501-42-9, entered on Mar. 27, 2019.
CAS Database Registry STN No. 2294382-59-3, entered on Mar. 27, 2019.
CAS Database Registry STN No. 2294379-83-0, entered on Mar. 27, 2019.
CAS Database Registry STN No. 2294353-32-3, entered on Mar. 27, 2019.
CAS Database Registry STN No. 2293758-23-1, entered on Mar. 26, 2019.
CAS Database Registry STN No. 2293235-24-0, entered on Mar. 26, 2019.
CAS Database Registry STN No. 2293231-63-5, entered on Mar. 26, 2019.
CAS Database Registry STN No. 2293211-33-1, entered on Mar. 26, 2019.
CAS Database Registry STN No. 2293211-30-8, entered on Mar. 26, 2019.
Gold-Von Simson, et al., "Kinetin in Familial Dysautonomia Carriers: Implication for a New Therapeutic Strategy Targeting mRNA Splicing," Pediatric Research, vol. 65(3), pp. 341-346, Mar. 2009.
Pedro J. Campos et al., "A Versatile Synthesis of Pyrrolo-, Furo- and Thienopyridines via Photocyclization of 3-Amino-2-alkene Imines in an Acid Medium," Tetrahedron, vol. 55, pp. 14079-14088, Dec. 3, 1999.
Sylvia L. Anderson et al., "Familial Dysautonomia Is Caused by Mutations of the IKAP Gene," Am. J. Hum. Genet., vol. 68, pp. 753-758, electronically published Jan. 22, 2001.
David Cheishvili et al., "IKAP/Elp1 involvement in cytoskeleton regulation and implication for familial dysautonomia," Human Molecular Genetics, vol. 20(8), pp. 1584-1594, Advance Access published Jan. 27, 2011.
Michael J. Munchhof et al., "Design and SAR of thienopyrimidine and thienopyridine inhibitors of VEGFR-2 kinase activity," Bioorg. & Med. Chem. Lett., vol. 14, 2004, pp. 21-24, Jan. 5, 2004.
David Cheishvili et al., "IKAP/hELP1 deficiency in the cerebrum of familial dysautonomia patients results in down regulation of genes involved in oligodendrocyte differentiation and in myelination," Human Molecular Genetics, 2007, vol. 16(17), pp. 2097-2104, Advanced Access published Jun. 25, 2007.
Evers Melvin M. et al., "Ataxin-3 protein modification as a treatment strategy for spinocerebellar ataxia type 3: Removal of the CAG containing exon", Neurobiology of Disease, [Online] vol. 58, May 6, 2013 (May 6, 2013), pp. 49-56, XP093217684.
Craig S. Mcintosh et al., "Removal of the Polyglutamine Repeat of Ataxin-3 by Redirecting pre-mRNA Processing", International Journal of Molecular Sciences, vol. 20, No. 21, Oct. 31, 2019 (Oct. 31, 2019), p. 5434, XP055712430.

(56) References Cited

OTHER PUBLICATIONS

Lodewijk J. A. Toonen et al., "Antisense oligonucleotide-mediated exon skipping as a strategy to reduce proteolytic cleavage of ataxin-3," Scientific Reports, vol. 6, No. 1, Oct. 12, 2016 (Oct. 12, 2016), XP055563933.
CAS Database Registry STN No. 2371515-24-9, entered on Sep. 1, 2019.
CAS Database Registry STN No. 1981326-49-1, entered on Aug. 28, 2016.
CAS Database Registry STN No. 1967610-91-8, entered Aug. 5, 2016.
CAS Database Registry STN No. 2327421-67-8, entered on Jun. 10, 2019.
CAS Database Registry STN No. 878601-07-1, entered on Mar. 30, 2006.
CAS Database Registry STN No. 879332-90-8, entered on Apr. 5, 2006.
CAS Database Registry STN No. 1349123-32-5, entered on Dec. 5, 2011.
CAS Database Registry STN No. 1967539-15-6, entered on Aug. 5, 2016.
CAS Database Registry STN No. 1914470-24-8, entered on May 20, 2016.
Berge et al., Pharmaceutical Salts, Journal of Pharmaceutical Sciences, 1977, pp. 1-19, vol. 66, Issue 1.
NCBI Database, 389066036, (Submission Date) Jun. 12, 2019 https://pubchem.ncbi.nlm.nih.gov/substance/389066036First Inventor: Database: NCBIID No. 389066036.
Philip L. Gould, Salt Selection for Basic Drugs, International Journal of Pharmaceutics, 1986, pp. 201-217, vol. 33, Issues 1-3.
Reeteka Sud et al., "Antisense-mediated Exon Skipping Decreases Tau Protein expression: A Potential Therapy for Tauopathies," Molecular Therapy-Nucleic Acids, 3, 2014, 7, published online Jul. 29, 2014, p. e180.
Fei Liu et al., "Tau exon 10 alternative splicing and tauopathies," Molecular Neurodegeneration, 3, 2008, 1, published Jul. 10, 2008, p. 8.
CAS Database Registry STN No. 1098386-78-7, entered on Feb. 1, 2009.
CAS Database Registry STN No. 939979-48-3, entered on Jun. 28, 2007.
Klockgether Thomas et al: "Spinocerebellar ataxia", Nature Reviews Disease Primers, Nature Publishing Group UK, London, vol. 5, No. 1, Apr. 11, 2019 (Apr. 11, 2019), pp. 1-21, XP036756583.
Written Opinion for PCT/US2023/068717 date mailed Nov. 8, 2023.
International Search Report for PCT/US2023/068717 date mailed Nov. 8, 2023.
Crespo et al., "Design, Synthesis, and Biological Activities of New Thieno[3,2-d]pyrimidines as Selective Type 4 Phosphodiesterase Inhibitors," J. Med. Chem., 41, published on web Sep. 12, 1998, pp. 4021-4035.
Barbara Makova et al., "Cytoprotective activities of kinetin purine isosteres", Bioorganic & Medicinal Chemistry, vol. 33, 2021, available online Jan. 6, 2021, pp. 1-14.

METHODS FOR TREATING SPINOCEREBELLAR ATAXIA TYPE 3

CROSS-REFERENCE TO RELATED APPLICATIONS

This application is a national phase entry under 35 USC § 371 of International Application PCT/US2022/014934, filed Feb. 2, 2022, which claims the benefit of, and priority to U.S. Provisional Patent Application No. 63/146,151 filed on Feb. 5, 2021, the contents of which are herein incorporated by reference in its entirety for all purposes.

TECHNICAL FIELD

The present description relates to methods of treating spinocerebellar ataxia type 3 (SCA3) using substituted thieno[3,2-d]pyrimidine compounds, forms, and pharmaceutical compositions thereof.

BACKGROUND

Spinocerebellar ataxia type 3 (SCA3), also known as Machado-Joseph disease (MJD), is a rare autosomal dominantly inherited disease characterized by progressive ataxia. SCA3 is the most common dominant ataxia worldwide. Although the accurate patient population is unknown, it has been estimated that the average prevalence is 1-5/100,000 with higher frequency in China, Portugal, Brazil, Netherlands, Germany, and Japan. It is also significant in the United States wherein SCA3 accounts for ~21% of dominant ataxia. Based on the age of onset, there are three subtypes of SCA3: subtype 1 (early-onset, 10-30 yr), subtype 2 (average-onset, 30-50 yr), and subtype 3 (late-onset, 50-70 yr). The SCA3 patients usually survive 10 to 20 years after the onset of symptoms. Symptoms include slowly progressive clumsiness in the arms and legs, a staggering lurching gait that can be mistaken for drunkenness, difficulty with speech and swallowing, impaired eye movements sometimes accompanied by double vision or bulging eyes, and lower limb spasticity; some individuals develop sustained muscle contractions that cause twisting of the body and limbs, repetitive movements, and abnormal postures; and others may develop twitching of the face or tongue, neuropathy, or problems with urination and the autonomic nervous system.

SCA3 is caused by an unstable expansion of cytosine-adenine-guanine (CAG) trinucleotide repeats in the A TXN3 gene that transcribes into mutant A TXN3 (mATXNT3) mRNA. This expansion in the mATXN3 mRNA leads to production of mutant ataxin-3 protein (ATXN3) containing a polymorphic polyglutamine (polyQ) tract. Both the mATXN3 mRNA and the mutant ATXN3 protein disrupt several cellular processes resulting in neurodegeneration in the cerebellum, brainstem, and other connected brain regions.

The number of CAG repeats in the ATXN3 mRNA ranges 10-45 in the healthy population, whereas in SCA3 patients, it can vary from 61-87. The number of CAG repeats between 45-60 is associated with an incomplete penetrance of the disease. As evidenced in other polyQ disorders, the number of repeats inversely correlates with the age of onset in SCA3 patients.

In several preclinical models of SCA3, reduction of ATXN3 protein levels improves SCA3 pathology, thus confirming the importance of ATNX3 lowering as a therapeutic target to ameliorate the downstream pathogenic effects. The present description relates to the use of a compound of Formula (I) or a form or composition thereof for treating SCA3. These sets of compounds induce exon 4 skipping in the ATXN3 pre-mRNA during the splicing process. Exon 4 skipping of ATXN3 mRNA changes the open reading frame (ORF) and creates premature termination codons (PTCs) in the AXTN3 exon 4-skipped mRNA (ΔE4 mRNA). It has been shown that such exon skipping splicing events could serve to reduce gene expression by creating mRNAs with premature termination codons, thus signaling the mRNAs to be degraded rather than translated into proteins. Similarly, ATXN3 ΔE4 mRNA produced in the presence of these compounds will undergo mRNA degradation resulting in decreased levels of ATXN3 mRNA, resulting in ATXN3 protein lowering.

To date, there are no disease-modifying therapies available for SCA3, and there exists a need for improved methods and compositions for treating SCA3 and the symptoms associated therewith. International Application No. PCT/US2020/063612 discloses substituted thieno[3,2-d]pyrimidine compounds useful for therapeutically targeting pre-mRNA splicing mechanisms in the IKBKAP gene and for the treatment of familial dysautonomia and International Application No. PCT/US2020/063612 discloses compounds that improve pre-mRNA splicing in the IKBKAP gene. Neither application discloses compounds that induce exon 4 skipping in ATXN3 pre-mRNA splicing. In addition, neither application discloses compounds that result in ATXN3 protein lowering, in particular ATXN3 protein lowering due to mRNA degradation of ATXN3 ΔE4 mRNA produced in the presence of the compounds. Furthermore, neither application discloses compounds that are useful for treating SCA3.

The compounds described herein represent potential ATXN3 pre-mRNA splicing compounds that could be used as a disease-modifying treatment for SCA3.

All other documents referred to herein are incorporated by reference into the present application as though fully set forth herein.

SUMMARY

The present description relates to a method or use of a compound for treating spinocerebellar ataxia type 3 (SCA3), also known as Machado-Joseph disease (MJD), in a subject in need thereof comprising administering to the subject an effective amount of a compound of Formula (I):

(I)

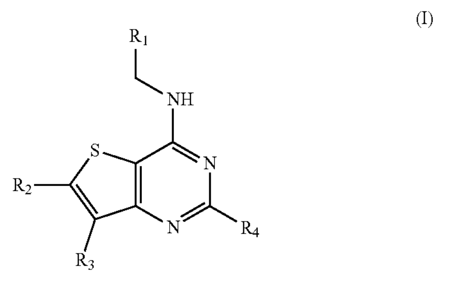

or a form thereof, wherein $R_1$, $R_2$, $R_3$, and $R_4$ are defined herein.

DETAILED DESCRIPTION

An aspect of the present description relates to a method or use of a compound for treating spinocerebellar ataxia type 3

(SCA3), also known as Machado-Joseph disease (MJD), in a subject in need thereof comprising administering to the subject an effective amount ofa compound of Formula (I):

(I)

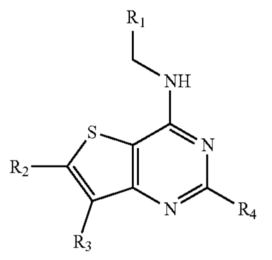

or a form thereof, wherein:

$R_1$ is selected from the group consisting of phenyl and heteroaryl, wherein heteroaryl is a 5-8 membered monocyclic or bicyclic aromatic carbon atom ring structure radical containing 1-3 heteroatoms selected from N, O, and S, and wherein phenyl or heteroaryl is optionally substituted with one, two, three, or four, independently selected $R_{1a}$ substituents:

$R_{1a}$ is independently selected from the group consisting of cyano, halo, hydroxy, $C_{1-6}$alkyl, halo-$C_{1-6}$alkyl, deutero-$C_{1-6}$alkyl, and $C_{1-6}$alkoxy;

$R_2$ is selected from the group consisting of hydrogen, $C_{1-6}$alkyl, $C_{2-6}$alkenyl, $C_{2-6}$alkynyl, $C_{3-10}$cycloalkyl, phenyl, heterocyclyl, and heteroaryl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S, wherein $C_{1-6}$alkyl, $C_{2-6}$alkenyl, and $C_{2-6}$alkynyl optionally contain a chiral carbon having an (R) or (S) configuration, and wherein $C_{1-6}$alkyl, $C_{2-6}$alkenyl, $C_{2-6}$alkynyl, $C_{3-10}$cycloalkyl, phenyl, heterocyclyl, or heteroaryl are optionally substituted with one, two, three, or four independently selected $R_{2a}$ substituents;

$R_{2a}$ is independently selected from the group consisting of cyano, halo, hydroxy, oxo, $C_{1-6}$alkyl, halo-$C_{1-6}$alkyl, deutero-$C_{1-6}$alkyl, $C_{2-6}$alkenyl, $C_{2-6}$alkynyl, $C_{1-6}$alkoxy, halo-$C_{1-6}$alkoxy, carboxyl, amino, $C_{1-6}$alkyl-amino, halo-$C_{1-6}$alkyl-amino, deutero-$C_{1-6}$alkyl-amino, $(C_{1-6}alkyl)_2$-amino, $C_{3-10}$cycloalkyl-amino, phenyl-amino, heterocyclyl-amino, heteroaryl-amino, $C_{1-6}$alkyl-thio, $C_{1-6}$alkyl-sulfonyl, $C_{3-10}$cycloalkyl, phenyl, heterocyclyl, and heteroaryl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S, and wherein each instance of $C_{3-10}$cycloalkyl, phenyl, heterocyclyl or heteroaryl is optionally substituted with one, two, three or four independently selected $R_{2a'}$ substituents;

$R_{2a'}$ is independently selected from the group consisting of cyano, halo, hydroxy, oxo, $C_{1-6}$alkyl, halo-$C_{1-6}$alkyl, deutero-$C_{1-6}$alkyl, and $C_{1-6}$alkoxy;

$R_3$ is selected from the group consisting of hydrogen, cyano, halo, hydroxy, $C_{1-6}$alkyl, halo-$C_{1-6}$alkyl, $C_{1-6}$alkoxy, amino, $C_{1-6}$alkyl-amino, $(C_{1-6}alkyl)_2$-amino, $C_{3-10}$cycloalkyl, phenyl, heterocyclyl, and heteroaryl, wherein heterocyclyl is a 3-7 membered monocyclic carbon atom ring structure radical containing 1-3 heteroatoms selected from N, O, and S, and wherein heteroaryl is a 5-8 membered monocyclic or bicyclic aromatic carbon atom ring structure radical containing 1-3 heteroatoms selected from N, O, and S, and wherein $C_{1-6}$alkyl, $C_{3-10}$cycloalkyl, phenyl, heterocyclyl, or heteroaryl is optionally substituted with one, two, three, or four independently selected $R_{3a}$ substituents;

$R_{3a}$ is independently selected from the group consisting of cyano, halo, hydroxy, $C_{1-6}$alkyl, halo-$C_{1-6}$alkyl, and $C_{1-6}$alkoxy;

$R_4$ is selected from the group consisting of hydrogen, cyano, halo, hydroxy, $C_{1-6}$alkyl, halo-$C_{1-6}$alkyl, $C_{1-6}$alkoxy, carbamoyl, $C_{3-10}$cycloalkyl, phenyl, and heterocyclyl, and wherein heterocyclyl is a 3-7 membered monocyclic carbon atom ring structure radical containing 1-3 heteroatoms selected from N, O, and S; and wherein the form of the compound is selected from the group consisting of a salt, hydrate, solvate, and tautomer form thereof.

One aspect of the method or use includes a compound of Formula (I), wherein $R_1$ is selected from the group consisting of phenyl and heteroaryl, wherein heteroaryl is a 5-8 membered monocyclic or bicyclic aromatic carbon atom ring structure radical containing 1-3 heteroatoms selected from N, O, and S, and wherein phenyl or heteroaryl are optionally substituted with one, two, three, or four, independently selected $R_{1a}$ substituents.

Another aspect of the method or use includes a compound of Formula (1), wherein Ri is selected from the group consisting of phenyl and heteroaryl, wherein heteroaryl is a 5-8 membered monocyclic or bicyclic aromatic carbon atom ring structure radical containing 1-3 heteroatoms selected from N, O, and S, and wherein phenyl or heteroaryl is optionally substituted with one or two independently selected $R_{1a}$ substituents.

Another aspect of the method or use includes a compound of Formula (I), wherein $R_1$ is phenyl, and wherein phenyl is optionally substituted with one, two, three, or four independently selected $R_{1a}$ substituents.

Another aspect of the method or use includes a compound of Formula (1), wherein $R_1$ is phenyl, and wherein phenyl is substituted with one $R_{1a}$ substituent.

Another aspect of the method or use includes a compound of Formula (I), wherein Ri is heteroaryl, wherein heteroaryl is a 5-8 membered monocyclic or bicyclic aromatic carbon atom ring structure radical containing 1-3 heteroatoms selected from N, O, and S, and wherein heteroaryl is optionally substituted with one, two, three, or four independently selected $R_{1a}$ substituents.

Another aspect of the method or use includes a compound of Formula (I), wherein Ri is heteroaryl, wherein heteroaryl is a 5-8 membered monocyclic or bicyclic aromatic carbon atom ring structure radical containing 1-3 heteroatoms selected from N, O, and S, and wherein heteroaryl is optionally substituted with one or two independently selected $R_{1a}$ substituents.

Another aspect of the method or use includes a compound of Formula (I), wherein $R_1$ is heteroaryl selected from the group consisting of furanyl, thiophenyl, 1H-pyrrolyl, 1H-pyrazolyl, 1H-imidazolyl, 1H-1,2,3-triazolyl, 2H-1,2,3-triazolyl, 1H-tetrazolyl, 1,2-thiazolyl, 1,3-thiazolyl, 1,2-oxazolyl, 1,3-oxazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, and wherein heteroaryl is optionally substituted with one, two, three, or four independently selected $R_{1a}$ substituents.

Another aspect of the method or use includes a compound of Formula (I), wherein $R_1$ is heteroaryl selected from the group consisting of furanyl, thiophenyl, 1H-pyrrolyl, 1H-pyrazolyl, 1H-imidazolyl, 1H-1,2,3-triazolyl, 2H-1,2,3-triazolyl, 1-tetrazolyl, 1,2-thiazolyl, 1,3-thiazolyl, 1,2-oxazolyl, 1,3-oxazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, and wherein heteroaryl is optionally substituted with one or two independently selected Ri substituents.

Another aspect of the method or use includes a compound of Formula (I), wherein $R_1$ is heteroaryl selected from the group consisting of furanyl, thiophenyl, 1H-pyrrolyl, 1H-pyrazolyl, 1H-imidazolyl, 1H-1,2,3-triazolyl, 2H-1,2,3-triazolyl, 1H-tetrazolyl, 1,2-thiazolyl, 1,3-thiazolyl, 1,2-oxazolyl, 1,3-oxazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, and wherein heteroaryl is optionally substituted with one $R_{1a}$ substituent.

Another aspect of the method or use includes a compound of Formula (I), wherein $R_1$ is heteroaryl selected from the group consisting of furanyl, thiophenyl, 1H-pyrrolyl, 1H-pyrazolyl, 1H-imidazolyl, 1H-1,2,3-triazolyl, 2H-1,2,3-triazolyl, 1H-tetrazolyl, 1,2-thiazolyl, 1,3-thiazolyl, 1,2-oxazolyl, 1,3-oxazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, and wherein heteroaryl is optionally substituted with two independently selected Ria substituents.

Another aspect of the method or use includes a compound of Formula (1), wherein $R_1$ is heteroaryl selected from the group consisting of furanyl, thiophenyl, 1H-pyrrolyl, 1H-pyrazolyl, 1H-imidazolyl, 2H-1,2,3-triazolyl, 1H-tetrazolyl, 1,2-thiazolyl, 1,3-thiazolyl, 1,2-oxazolyl, 1,3-oxazolyl, 1,2-thiazolyl, 1,3-thiazolyl, 1,2-oxazolyl, 1,3-oxazolyl, pyridinyl, pyrimidinyl, and pyrazinyl, and wherein heteroaryl is optionally substituted with one, two, three, or four independently selected $R_{1a}$ substituents.

Another aspect of the method or use includes a compound of Formula (I), wherein R is heteroaryl selected from the group consisting of furanyl, thiophenyl, 1H-pyrrolyl, 1H-pyrazolyl, 1H-imidazolyl, 2H-1,2,3-triazolyl, 1H-tetrazolyl, 1,2-thiazolyl, 1,3-thiazolyl, 1,2-oxazolyl, 1,3-oxazolyl, 1,2-thiazolyl, 1,3-thiazolyl, 1,2-oxazolyl, 1,3-oxazolyl, pyridinyl, pyrimidinyl, and pyrazinyl, and wherein heteroaryl is optionally substituted with one or two independently selected Ria substituents.

Another aspect of the method or use includes a compound of Formula (I), wherein Ri is heteroaryl selected from the group consisting of furanyl, thiophenyl, 1H-pyrrolyl, 1H-pyrazolyl, 1H-imidazolyl, 2H-1,2,3-triazolyl, 1H-tetrazolyl, 1,2-thiazolyl, 1,3-thiazolyl, 1,2-oxazolyl, 1,3-oxazolyl, 1,2-thiazolyl, 1,3-thiazolyl, 1,2-oxazolyl, 1,3-oxazolyl, pyridinyl, pyrimidinyl, and pyrazinyl, and wherein heteroaryl is optionally substituted with one $R_{1a}$ substituents.

Another aspect of the method or use includes a compound of Formula (I), wherein $R_1$ is heteroaryl selected from the group consisting of furanyl, thiophenyl, 1H-pyrrolyl, 1H-pyrazolyl, 1H-imidazolyl, 2H-1,2,3-triazolyl, 1H-tetrazolyl, 1,2-thiazolyl, 1,3-thiazolyl, 1,2-oxazolyl, 1,3-oxazolyl, 1,2-thiazolyl, 1,3-thiazolyl, 1,2-oxazolyl, 1,3-oxazolyl, pyridinyl, pyrimidinyl, and pyrazinyl, and wherein heteroaryl is optionally substituted with two independently selected Ria substituents.

Another aspect of the method or use includes a compound of Formula (I), wherein Ri is heteroaryl selected from the group consisting of furan-2-yl, furan-3-yl, thiophen-2-yl, thiophen-3-yl, 1H-pyrrol-2-yl, 1H-pyrrol-3-yl, 1H-pyrazol-1-yl, 1H-pyrazol-3-yl, 1H-pyrazol-4-yl, 1H-pyrazol-5-yl, 1H-imidazol-1-yl, 1H-imidazol-2-yl, 1H-imidazol-4-yl, 1H-imidazol-5-yl, 1H-1,2,3-triazol-1-yl, 1H-1,2,3-triazol-4-yl, 2H-1,2,3-triazol-2-yl, 2H-1,2,3-triazol-4-yl, 1H-tetrazol-1-yl, 1H-tetrazol-5-yl, 1,2-thiazol-3-yl, 1,2-thiazol-4-yl, 1,2-thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, tetrazol-5-yl, 1,2,3-triazol-4-yl, 1,2,3-triazol-5-yl, 1,2,3-thiadiazol-4-yl, 1,2,3-thiadiazol-5-yl, pyridin-2-yl, pyridin-3-yl, pyridin-4-yl, pyrimidin-2-yl, pyrimidin-4-yl, pyrazin-2-yl, pyridazin-3-yl, pyridazin-4-yl, benzofuran-2-yl, benzofuran-5-yl, and quinoline-4-yl, and wherein heteroaryl is optionally substituted with one, two, three, or four independently selected $R_{1a}$ substituents.

Another aspect of the method or use includes a compound of Formula (I), wherein $R_1$ is heteroaryl selected from the group consisting of furan-2-yl, furan-3-yl, thiophen-2-yl, thiophen-3-yl, 1H-pyrrol-2-yl, 1H-pyrrol-3-yl, 1H-pyrazol-1-yl, 1H-pyrazol-3-yl, 1H-pyrazol-4-yl, 1H-pyrazol-5-yl, 1H-imidazol-1-yl, 1H-imidazol-2-yl, 1H-imidazol-4-yl, 1H-imidazol-5-yl, 1H-1,2,3-triazol-1-yl, 1H-1,2,3-triazol-4-yl, 2H-1,2,3-triazol-2-yl, 2H-1,2,3-triazol-4-yl, 1H-tetrazol-1-yl, 1H-tetrazol-5-yl, 1,2-thiazol-3-yl, 1,2-thiazol-4-yl, 1,2-thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, tetrazol-5-yl, 1,2,3-triazol-4-yl, 1,2,3-triazol-5-yl, 1,2,3-thiadiazol-4-yl, 1,2,3-thiadiazol-5-yl, pyridin-2-yl, pyridin-3-yl, pyridin-4-yl, pyrimidin-2-yl, pyrimidin-4-yl, pyrazin-2-yl, pyridazin-3-yl, pyridazin-4-yl, benzofuran-2-yl, benzofuran-5-yl, and quinoline-4-yl, and wherein heteroaryl is optionally substituted with one or two independently selected $R_{1a}$ substituents.

Another aspect of the method or use includes a compound of Formula (I), wherein $R_1$ is heteroaryl selected from the group consisting of furan-2-yl, furan-3-yl, thiophen-2-yl, thiophen-3-yl, 1H-pyrrol-2-yl, 1H-pyrrol-3-yl, 1H-pyrazol-1-yl, 1H-pyrazol-3-yl, 1H-pyrazol-4-yl, 1H-pyrazol-5-yl, 1H-imidazol-1-yl, 1H-imidazol-2-yl, 1H-imidazol-4-yl, 1H-imidazol-5-yl, 1H-1,2,3-triazol-1-yl, 1H-1,2,3-triazol-4-yl, 2H-1,2,3-triazol-2-yl, 2H-1,2,3-triazol-4-yl, 1H-tetrazol-1-yl, 1H-tetrazol-5-yl, 1,2-thiazol-3-yl, 1,2-thiazol-4-yl, 1,2- thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, tetrazol-5-yl, 1,2,3-triazol-4-yl, 1,2,3-triazol-5-yl, 1,2,3-thiadiazol-4-yl, 1,2,3-thiadiazol-5-yl, pyridin-2-yl, pyridin-3-yl, pyridin-4-yl, pyrimidin-2-yl, pyrimidin-4-yl, pyrazin-2-yl, pyridazin-3-yl, pyridazin-4-yl, benzofuran-2-yl, benzofuran-5-yl, and quinoline-4-yl, and wherein heteroaryl is optionally substituted with one $R_{1a}$ substituent.

Another aspect of the method or use includes a compound of Formula (I), wherein $R_1$ is heteroaryl selected from the group consisting of furan-2-yl, furan-3-yl, thiophen-2-yl, thiophen-3-yl, 1H-pyrrol-2-yl, 1H-pyrrol-3-yl, 1H-pyrazol-1-yl, 1H-pyrazol-3-yl, 1H-pyrazol-4-yl, 1H-pyrazol-5-yl, 1H-imidazol-1-yl, 1H-imidazol-2-yl, 1H-imidazol-4-yl, 1H-imidazol-5-yl, 1H-1,2,3-triazol-1-yl, 1H-1,2,3-triazol-4-yl, 2H-1,2,3-triazol-2-yl, 2H-1,2,3-triazol-4-yl, 1H-tetrazol-1-yl, 1H-tetrazol-5-yl, 1,2-thiazol-3-yl, 1,2-thiazol-4-yl, 1,2-thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, tetrazol-5-yl, 1,2,3-triazol-4-yl, 1,2,3-triazol-5-yl, 1,2,3-thiadiazol-4-yl, 1,2,3-thiadiazol-5-yl, pyridin-2-yl, pyridin-3-yl, pyridin-4-yl, pyrimidin-2-yl, pyrimidin-4-yl, pyrazin-2-yl, pyridazin-3-yl, pyridazin-4-yl, benzofuran-2-yl, benzofuran-5-yl, and quinoline-4-yl, and wherein heteroaryl is optionally substituted with two independently selected Ria substituents.

Another aspect of the method or use includes a compound of Formula (I), wherein $R_1$ is heteroaryl selected from the group consisting of furan-2-yl, furan-3-yl, thiophen-2-yl, thiophen-3-yl, 1H-pyrrol-2-yl, I-pyrrol-3-yl, 1H-pyrazol-3-yl, lR-pyrazol-4-yl, 1H-pyrazol-5-yl, 1H-imidazol-2-yl, 1H-imidazol-4-yl, 1H-imidazol-5-yl, 2H-1,2,3-triazol-4-yl, 1H-tetrazol-5-yl, 1,2-thiazol-4-yl, 1,2-thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, pyridin-2-yl, pyridin-3-yl, pyridin-4-yl, pyrimidin-2-yl, pyrimidin-4-yl, and pyrazin-2-yl, and wherein heteroaryl is optionally substituted with one, two, three, or four independently selected $R_{1a}$ substituents.

Another aspect of the method or use includes a compound of Formula (1), wherein $R_1$ is heteroaryl selected from the group consisting of furan-2-yl, furan-3-yl, thiophen-2-yl, thiophen-3-yl, 1H-pyrrol-2-yl, 1H-pyrrol-3-yl, 11H-pyrazol-3-yl, 1H-pyrazol-4-yl, 1H-pyrazol-5-yl, 1H-imidazol-2-yl, 1H-imidazol-4-yl, 1H-imidazol-5-yl, 2H-1,2,3-triazol-4-yl, TH-tetrazol-5-yl, 1,2-thiazol-4-yl, 1,2-thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, pyridin-2-yl, pyridin-3-yl, pyridin-4-yl, pyrimidin-2-yl, pyrimidin-4-yl, and pyrazin-2-yl, and wherein heteroaryl is optionally substituted with one or two independently selected Ria substituents.

Another aspect of the method or use includes a compound of Formula (I), wherein Ri is heteroaryl selected from the group consisting of furan-2-yl, furan-3-yl, thiophen-2-yl, thiophen-3-yl, 1H-pyrrol-2-yl, 1H-pyrrol-3-yl, 1H-pyrazol-3-yl, 1H-pyrazol-4-yl, 1H-pyrazol-5-yl, 1H-imidazol-2-yl, 1H-imidazol-4-yl, 1H-imidazol-5-yl, 2H-1,2,3-triazol-4-yl, 1H-tetrazol-5-yl, 1,2-thiazol-4-yl, 1,2-thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, pyridin-2-yl, pyridin-3-yl, pyridin-4-yl, pyrimidin-2-yl, pyrimidin-4-yl, and pyrazin-2-yl, and wherein heteroaryl is optionally substituted with one $R_{1a}$ substituent.

Another aspect of the method or use includes a compound of Formula (1), wherein $R_1$ is heteroaryl selected from the group consisting of furan-2-yl, furan-3-yl, thiophen-2-yl, thiophen-3-yl, 1H-pyrrol-2-yl, 1H-pyrrol-3-yl, 1H-pyrazol-3-yl, 1H-pyrazol-4-yl, 1H-pyrazol-5-yl, 1H-imidazol-2-yl, 1H-imidazol-4-yl, 1H-imidazol-5-yl, 2H-1,2,3-triazol-4-yl, 1H-tetrazol-5-yl, 1,2-thiazol-4-yl, 1,2-thiazol-5-yl, 1,3-thiazol-2-yl, 1,3-thiazol-4-yl, 1,3-thiazol-5-yl, 1,2-oxazol-3-yl, 1,2 oxazol-4-yl, 1,2-oxazol-5-yl, 1,3-oxazol-2-yl, 1,3-oxazol-4-yl, 1,3-oxazol-5-yl, pyridin-2-yl, pyridin-3-yl, pyridin-4-yl, pyrimidin-2-yl, pyrimidin-4-yl, and pyrazin-2-yl, and wherein heteroaryl is optionally substituted with two independently selected $R_{1a}$substituents.

One aspect of the method or use includes a compound of Formula (I), wherein Ri, is independently selected from the group consisting of cyano, halo, hydroxy, $C_{1-6}$alkyl, halo-$C_{1-6}$alkyl, deutero-$C_{1-6}$alkyl, and $C_{1-6}$alkoxy.

Another aspect of the method or use includes a compound of Formula (1), wherein Rja is independently selected from the group consisting of halo and $C_{1-6}$alkyl.

Another aspect of the method or use includes a compound of Formula (1), wherein $R_{1a}$ is halo, wherein halo is selected from the group consisting of fluoro, chloro, bromo, and iodo.

Another aspect of the method or use includes a compound of Formula (I), wherein $R_{1a}$ is fluoro.

Another aspect of the method or use includes a compound of Formula (I), wherein Ri, is $C_{1-6}$alkyl selected from the group consisting of methyl, ethyl, propyl, butyl, pentyl, and hexyl.

Another aspect of the method or use includes a compound of Formula (I), wherein $R_{1a}$ is methyl.

One aspect of the method or use includes a compound of Formula (I), wherein $R_2$ is selected from the group consisting of hydrogen, $C_{1-6}$alkyl, $C_{2-6}$alkenyl, $C_{2-6}$alkynyl, $C_{3-10}$cycloalkyl, phenyl, heterocyclyl, and heteroaryl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S, wherein $C_{1-6}$alkyl, $C_{2-6}$alkenyl, and $C_{2-6}$alkynyl optionally contain a chiral carbon having an (R) or (S) configuration, and wherein $C_{1-6}$alkyl, $C_{2-6}$alkenyl, $C_{2-6}$alkynyl, $C_{3-10}$cycloalkyl, phenyl, heterocyclyl, and heteroaryl are optionally substituted with one, two, three, or four independently selected $R_{2a}$ substituents.

Another aspect of the method or use includes a compound of Formula (I), wherein $R_2$ is hydrogen.

Another aspect of the method or use includes a compound of Formula (I), wherein $R_2$ is $C_{1-6}$alkyl, wherein $C_{1-6}$alkyl optionally contains a chiral carbon having an (R) or (S) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl, wherein $C_{1-6}$alkyl contains a chiral carbon having an (R) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl, wherein $C_{1-6}$alkyl contains a chiral carbon having an (S) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl selected from the group consisting of methyl, ethyl, propyl, butyl, pentyl, and hexyl, wherein $C_{1-6}$alkyl optionally contains a chiral carbon having an (R) or (S) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl selected from the group consisting of methyl, ethyl, propyl, butyl, pentyl, and hexyl, wherein $C_{1-6}$alkyl contains a chiral carbon having an (R) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl selected from the group consisting of methyl, ethyl, propyl, butyl, pentyl, and hexyl, wherein $C_{1-6}$alkyl contains a chiral carbon having an (5) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl selected from the group consisting of methyl, ethyl, propyl, butyl, and pentyl, wherein $C_{1-6}$alkyl optionally contains a chiral carbon having an (R) or (S) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl selected from the group consisting of methyl, ethyl, propyl, butyl, and pentyl, wherein $C_{1-6}$alkyl contains a chiral carbon having an (R) configuration, and wherein $C_{1-6}$alkyl is optionally substituted with one, two, three, or four, independently selected $R_{2a}$ substituents.

Another aspect of the method or use includes a compound of Formula (I), wherein $R_2$ is $C_{1-6}$alkyl selected from the group consisting of methyl, ethyl, propyl, butyl, and pentyl, wherein $C_{1-6}$alkyl contains a chiral carbon having an (S) configuration, and wherein $C_{1-6}$alkyl is optionally substituted with one, two, three, or four, independently selected $R_{2a}$ substituents.

Another aspect of the method or use includes a compound of Formula (I), wherein $R_2$ is heterocyclyl, wherein heterocyclyl is a 3-7 membered monocyclic carbon atom ring structure radical containing 1-3 heteroatoms selected from N, O, and S, and wherein heterocyclyl is optionally substituted with one, two, three, or four independently selected $R_{2a}$ substituents.

Another aspect of the method or use includes a compound of Formula (I), wherein $R_2$ is heterocyclyl, wherein heterocyclyl is a 3-7 membered monocyclic carbon atom ring structure radical containing 1-3 heteroatoms selected from N, O, and S, and wherein heterocyclyl is optionally substituted with one, two, three, or four independently selected $R_{2a}$ substituents.

Another aspect of the method or use includes a compound of Formula (I), wherein $R_2$ is heterocyclyl, wherein heterocyclyl is a 3-7 membered monocyclic carbon atom ring structure radical containing 1-3 heteroatoms selected from N, O, and S, and wherein heterocyclyl is optionally substituted with one, two, three, or four independently selected $R_{2a}$ substituents.

Another aspect of the method or use includes a compound of Formula (1), wherein $R_2$ is heterocyclyl selected from the group consisting of azetidinyl, oxetanyl, pyrazolidinyl, tetrahydrofuranyl, oxazolidinyl, thiazolidinyl, isothiazolidinyl, pyrrolidinyl, piperidinyl, piperazinyl, 2H-pyranyl, tetrahydropyranyl, morpholinyl, 1,3-oxazinanyl, 1,3-oxazinan-2-on-yl, and azepanyl, and wherein heterocyclyl is optionally substituted with one, two, three, or four independently selected $R_{2a}$ substituents.

Another aspect of the method or use includes a compound of Formula (I), wherein $R_2$ is heterocyclyl selected from the group consisting of azetidinyl and pyrrolidinyl, and wherein heterocyclyl is optionally substituted with one, two, three, or four independently selected $R_{2a}$ substituents.

Another aspect of the method or use includes a compound of Formula (I), wherein $R_2$ is heterocyclyl selected from the group consisting of azetidin-2-yl, azetidin-3-yl, oxetan-2-yl, oxetan-3-yl, pyrazolidin-1-yl, pyrazolidin-2-yl, pyrazolidin-3-yl, pyrazolidin-4-yl, pyrazolidin-5-yl, tetrahydrofuran-1-yl, tetrahydrofuran-2-yl, oxazolidin-2-yl, oxazolidin-4-yl, oxazolidin-5-yl, thiazolidin-2-yl, thiazolidin-4-yl, thiazolidin-5-yl, isothiazolidin-3-yl, isothiazolidin-4-yl, isothiazolidin-5-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, 2H-pyran-2-yl, 2H-pyran-3-yl, 2H-pyran-4-yl, 2H-pyran-5-yl, 2H-pyran-6-yl, tetrahydropyran-2-yl, tetrahydropyran-3-yl, tetrahydropyran-4-yl, morpholin-2-yl, morpholin-3-yl, morpholin-4-yl, 1,3-oxazinan-2-yl, 1,3-oxazinan-3-yl, 1,3-oxazinan-4-yl, 1,3-oxazinan-2-on-6-yl, azepan-1-yl, azepan-2-yl, azepan-3-yl, and azepan-4-yl, and wherein heterocyclyl is optionally substituted with one, two, three, or four independently selected $R_{2a}$ substituents.

Another aspect of the method or use includes a compound of Formula (I), wherein $R_2$ is heterocyclyl selected from the group consisting of azetidin-3-yl and pyrrolidin-3-yl, and wherein heterocyclyl is optionally substituted with one, two, three, or four independently selected $R_{2a}$ substituents.

One aspect of the method or use includes a compound of Formula (1), wherein $R_{2a}$ is independently selected from the group consisting of cyano, halo, hydroxy, oxo, $C_{1-6}$alkyl, halo-$C_{1-6}$alkyl, deutero-$C_{1-6}$alkyl, $C_{2-6}$alkenyl, $C_{2-6}$alkynyl, $C_{1-6}$alkoxy, halo-$C_{1-6}$alkoxy, carboxyl, amino, $C_{1-6}$alkyl-amino, halo-$C_{1-6}$alkyl-amino, deutero-$C_{1-6}$alkyl-amino, $(C_{1-6}alkyl)_2$-amino, $C_{3-10}$cycloalkyl-amino, phenyl-amino, heterocyclyl-amino, heteroaryl-amino, $C_{1-6}$alkyl-thio, $C_{1-6}$alkyl-sulfonyl, $C_{3-10}$cycloalkyl, phenyl, heterocyclyl, and heteroaryl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S, and wherein each instance of $C_{3-10}$cycloalkyl, phenyl, heterocyclyl or heteroaryl is optionally substituted with one, two, three or four independently selected $R_{2a'}$ substituents.

Another aspect of the method or use includes a compound of Formula (I), wherein $R_{2a}$ is independently selected from the group consisting of halo, hydroxy, $C_{1-6}$alkyl, $C_{1-6}$alkoxy, amino, $C_{1-6}$alkyl-amino, $C_{3-10}$cycloalkyl-amino, $C_{3-10}$ cycloalkyl, or heterocyclyl, wherein each instance of $C_{3-10}$cycloalkyl or heterocyclyl is optionally substituted with one, two, three or four independently selected $R_{2a'}$ substituents.

Another aspect of the method or use includes a compound of Formula (I), wherein $R_{2a}$ is halo selected from the group consisting of fluoro, chloro, bromo, and iodo.

Another aspect of the method or use includes a compound of Formula (I), wherein $R_{2a}$ is fluoro.

Another aspect of the method or use includes a compound of Formula (I), wherein $R_{2a}$ is hydroxy.

Another aspect of the method or use includes a compound of Formula (I), wherein $R_{2a}$ is $C_{1-6}$alkyl selected from the group consisting of methyl, ethyl, propyl, butyl, pentyl, and hexyl.

Another aspect of the method or use includes a compound of Formula (I), wherein $R_{2a}$ is methyl.

Another aspect of the method or use includes a compound of Formula (I), wherein $R_{2a}$ is $C_{1-6}$alkoxy selected from the group consisting of methoxy, ethoxy, propoxy, isopropoxy, butoxy, and tert-butoxy.

Another aspect of the method or use includes a compound of Formula (I), wherein $R_{2a}$ is methoxy.

Another aspect of the method or use includes a compound of Formula (I), wherein $R_{2a}$ is amino.

Another aspect of the method or use includes a compound of Formula (I), wherein $R_{2a}$ is $C_{1-6}$alkyl-amino, and wherein $C_{1-6}$alkyl is selected from the group consisting of methyl, ethyl, propyl, isopropyl, butyl, sec-butyl, isobutyl, and tert-butyl.

Another aspect of the method or use includes a compound of Formula (1), wherein $R_{2a}$ is methyl-amino.

Another aspect of the method or use includes a compound of Formula (I), wherein $R_{2a}$ is $C_{3-10}$cycloalkyl-amino, wherein $C_{3-10}$ cycloalkyl is selected from the group consisting of cyclopropyl, cyclobutyl, cyclopentyl, cyclohexyl, cycloheptyl, and cyclooctyl, and wherein $C_{3-10}$cycloalkyl is optionally substituted with one, two, three or four independently selected $R_{2a'}$ substituents.

Another aspect of the method or use includes a compound of Formula (I), wherein $R_{2a}$ is cyclobutyl-amino.

Another aspect of the method or use includes a compound of Formula (1), wherein $R_{2a}$ is $C_{3-10}$ cycloalkyl, wherein $C_{3-10}$cycloalkyl is selected from cyclopropyl, cyclobutyl, cyclopentyl, cyclohexyl, cycloheptyl, and cyclooctyl, and wherein $C_{3-10}$cycloalkyl is optionally substituted with one, two, three or four independently selected $R_{2a'}$ substituents.

Another aspect includes a compound of Formula (I), wherein $R_{2a}$ is cyclopropyl, optionally substituted with one, two, three or four independently selected $R_{2a'}$ substituents.

Another aspect of the method or use includes a compound of Formula (I), wherein $R_{2a}$ is heterocyclyl selected from the group consisting of azetidinyl, oxetanyl, pyrazolidinyl, tetrahydrofuranyl, oxazolidinyl, thiazolidinyl, isothiazolidinyl, pyrrolidinyl, piperidinyl, piperazinyl, 2H-pyranyl, tetrahydropyranyl, morpholinyl, 1,3-oxazinanyl, 1,3-oxazinan-2-on-yl, and azepanyl, and wherein heterocyclyl is optionally substituted with one, two, three, or four independently selected $R_{2a'}$ substituents.

Another aspect of the method or use includes a compound of Formula (1), wherein $R_{2a}$ is 1,3-oxazinan-2-on-yl.

Another aspect of the method or use includes a compound of Formula (I), wherein $R_{2a}$ is heterocyclyl selected from the group consisting of azetidin-2-yl, azetidin-3-yl, oxetan-2-yl, oxetan-3-yl, pyrazolidin-1-yl, pyrazolidin-2-yl, pyrazolidin-3-yl, pyrazolidin-4-yl, pyrazolidin-5-yl, tetrahydrofuran-1-yl, tetrahydrofuran-2-yl, oxazolidin-2-yl, oxazolidin-4-yl, oxazolidin-5-yl, thiazolidin-2-yl, thiazolidin-4-yl, thiazolidin-5-yl, isothiazolidin-3-yl, isothiazolidin-4-yl, isothiazolidin-5-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, 2H-pyran-2-yl, 2H-pyran-3-yl, 2H-pyran-4-yl, 2H-pyran-5-yl, 2H-pyran-6-yl, tetrahydropyran-2-yl, tetrahydropyran-3-yl, tetrahydropyran-4-yl, morpholin-2-yl, morpholin-3-yl, morpholin-4-yl, 1,3-oxazinan-2-yl, 1,3-oxazinan-3-yl, 1,3-oxazinan-4-yl, 1,3-oxazinan-2-on-6-yl, azepan-1-yl, azepan-2-yl, azepan-3-yl, and azepan-4-yl, and wherein heterocyclyl is optionally substituted with one, two, three, or four independently selected $R_{2a'}$ substituents.

Another aspect of the method or use includes a compound of Formula (I), wherein $R_{2a}$ is 1,3-oxazinan-2-on-6-yl.

One aspect includes a compound of Formula (I), wherein $R_3$ is selected from the group consisting of hydrogen, cyano, halo, hydroxy, $C_{1-6}$alkyl, halo-$C_{1-6}$alkyl, $C_{1-6}$alkoxy, amino, $C_{1-6}$alkyl-amino, $(C_{1-6}alkyl)_2$-amino, $C_{3-10}$cycloalkyl, phenyl, heterocyclyl, and heteroaryl, wherein heterocyclyl is a 3-7 membered monocyclic carbon atom ring structure radical containing 1-3 heteroatoms selected from N, O, and S, and wherein heteroaryl is a 5-8 membered monocyclic or bicyclic aromatic carbon atom ring structure radical containing 1-3 heteroatoms selected from N, O, and S, and wherein each instance of $C_{1-6}$alkyl, $C_{3-10}$cycloalkyl, phenyl, heterocyclyl, or heteroaryl is optionally substituted with one, two, three, or four independently selected $R_{3a}$ substituents.

Another aspect includes a compound of Formula (1), wherein $R_3$ is selected from the group consisting of hydrogen, cyano, halo, $C_{1-6}$alkyl, $C_{1-6}$alkoxy, $C_{3-10}$cycloalkyl, and phenyl, and wherein $C_{1-6}$alkyl, $C_{3-10}$cycloalkyl, or phenyl is optionally substituted with one, two, three, or four independently selected $R_{1a}$ substituents.

Another aspect of the method or use includes a compound of Formula (I), wherein $R_3$ is hydrogen.

Another aspect of the method or use includes a compound of Formula (I), wherein $R_3$ is cyano.

Another aspect of the method or use includes a compound of Formula (I), wherein $R_3$ is halo selected from the group consisting of fluoro, chloro, bromo, and iodo.

Another aspect of the method or use includes a compound of Formula (I), wherein $R_3$ is bromo.

Another aspect of the method or use includes a compound of Formula (I), wherein $R_3$ is hydroxy.

Another aspect of the method or use includes a compound of Formula (I), wherein $R_3$ is selected from the group consisting of methyl, ethyl, propyl, butyl, pentyl, and hexyl, and wherein $C_{1-6}$alkyl is optionally substituted with one, two, three, or four independently selected $R_3$, substituents.

Another aspect of the method or use includes a compound of Formula (I), wherein $R_3$ is $C_{1-6}$-alkyl selected from the group consisting of methyl and ethyl, and wherein $C_{1-6}$alkyl is optionally substituted with one, two, three, or four independently selected $R_{3a}$ substituents.

Another aspect of the method or use includes a compound of Formula (1), wherein $R_3$ is $C_{1-6}$alkoxy selected from the group consisting of methoxy, ethoxy, propoxy, isopropoxy, butoxy, and tert-butoxy.

Another aspect of the method or use includes a compound of Formula (I), wherein $R_3$ is methoxy.

Another aspect of the method or use includes a compound of Formula (I), wherein $R_3$ is $C_{3-10}$cycloalkyl selected from the group consisting of cyclopropyl, cyclobutyl, cyclopentyl, cyclohexyl, cycloheptyl, and cyclooctyl, and wherein $C_{3-10}$ cycloalkyl is optionally substituted with one, two, three, or four independently selected $R_{3a}$ substituents.

Another aspect of the method or use includes a compound of Formula (I), wherein $R_3$ is cyclopropyl, optionally substituted with one, two, three, or four independently selected $R_{3a}$ substituents.

Another aspect of the method or use includes a compound of Formula (I), wherein $R_3$ is phenyl, optionally substituted with one, two, three, or four independently selected $R_{3a}$ substituents.

One aspect of the method or use includes a compound of Formula (1), wherein $R_{3a}$ is selected from the group consisting of cyano, halo, hydroxy, $C_{1-6}$alkyl, halo-$C_{1-6}$alkyl, and $C_{1-6}$alkoxy.

Another aspect of the method or use includes a compound of Formula (I), wherein $R_3$, is selected from the group consisting of halo and $C_{1-6}$alkoxy.

Another aspect of the method or use includes a compound of Formula (I), wherein $R_{3a}$ is halo selected from the group consisting of fluoro, chloro, bromo, and iodo.

Another aspect of the method or use includes a compound of Formula (I), wherein $R_{3a}$ is chloro.

Another aspect of the method or use includes a compound of Formula (I), wherein $R_{3a}$ is $C_{1-6}$alkoxy selected from the group consisting of methoxy, ethoxy, propoxy, isopropoxy, butoxy, and tert-butoxy.

Another aspect of the method or use includes a compound of Formula (I), wherein $R_{3a}$ is methoxy.

One aspect of the method or use includes a compound of Formula (I), wherein $R_4$ is selected from the group consisting of hydrogen, cyano, halo, hydroxy, $C_{1-6}$alkyl, halo-$C_{1-6}$alkyl, $C_{1-6}$alkoxy, carbamoyl, $C_{3-10}$cycloalkyl, phenyl, and heterocyclyl, and wherein heterocyclyl is a 3-7 membered monocyclic carbon atom ring structure radical containing 1-3 heteroatoms selected from N, O, and S.

Another aspect of the method or use includes a compound of Formula (I), wherein $R_4$ is selected from the group consisting of hydrogen, cyano, halo, $C_{1-6}$alkyl, halo-$C_{1-6}$alkyl, carbamoyl, $C_{3-10}$cycloalkyl, and phenyl.

Another aspect of the method or use includes a compound of Formula (I), wherein $R_4$ is hydrogen.

Another aspect of the method or use includes a compound of Formula (1), wherein $R_4$ is cyano.

Another aspect of the method or use includes a compound of Formula (I), wherein $R_4$ is halo selected from the group consisting of fluoro, chloro, bromo, and iodo.

Another aspect of the method or use includes a compound of Formula (I), wherein $R_4$ is halo selected the group consisting of chloro and bromo.

Another aspect of the method or use includes a compound of Formula (I), wherein $R_4$ is $C_{1-6}$alkyl selected from the group consisting of methyl, ethyl, propyl, butyl, pentyl, and hexyl.

Another aspect of the method or use includes a compound of Formula (I), wherein $R_4$ is $C_{1-6}$alkyl selected from the group consisting of methyl and ethyl.

Another aspect of the method or use includes a compound of Formula (I), wherein $R_4$ is halo-$C_{1-6}$alkyl, wherein $C_{1-6}$alkyl is selected from the group consisting of methyl, ethyl, propyl, butyl, pentyl, and hexyl, and wherein $C_{1-6}$alkyl is partially or completely substituted with one or more halogen atoms where allowed by available valences.

Another aspect of the method or use includes a compound of Formula (I), wherein $R_4$ is halo-$C_{1-6}$alkyl, and wherein $C_{1-6}$alkyl is methyl substituted with three fluorine atoms.

Another aspect of the method or use includes a compound of Formula (I), wherein $R_4$ is carbamoyl.

Another aspect of the method or use includes a compound of Formula (I), wherein $R_4$ is $C_{3-10}$cycloalkyl selected from the group consisting of cyclopropyl, cyclobutyl, cyclopentyl, cyclohexyl, cycloheptyl, and cyclooctyl.

Another aspect of the method or use includes a compound of Formula (I), wherein $R_4$ is cyclopropyl.

Another aspect of the method or use includes a compound of Formula (I), wherein $R_4$ is phenyl.

One aspect of the method or use includes a compound of Formula (I) or a form thereof includes a compound selected from the group consisting of:

1

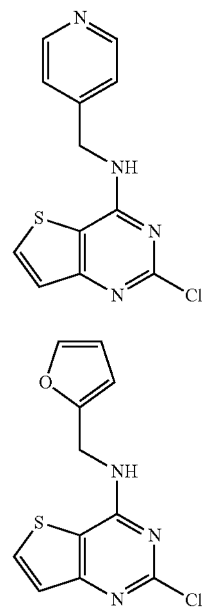

2

-continued
3
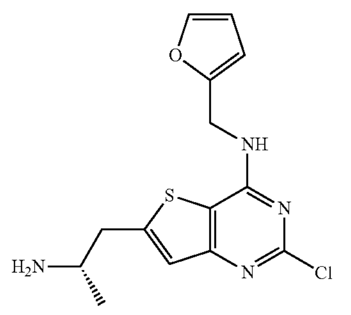
4
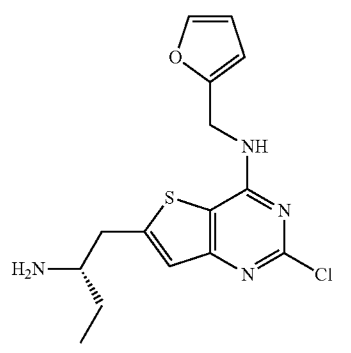
5
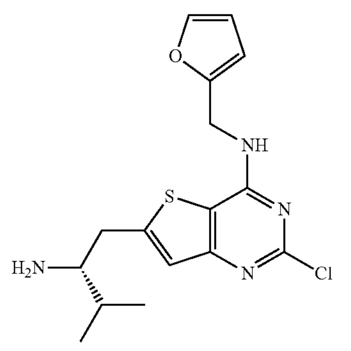
6
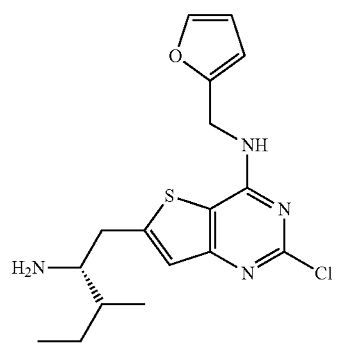
-continued
7
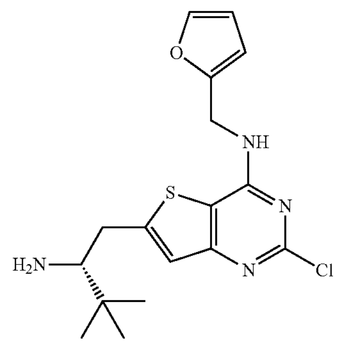
8
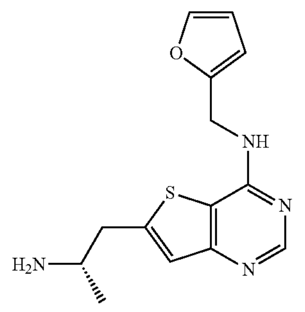
9
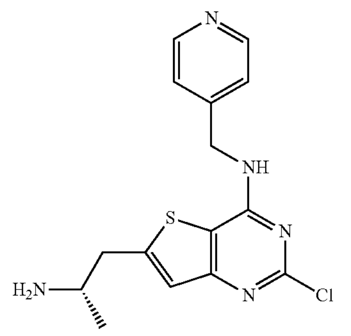
10
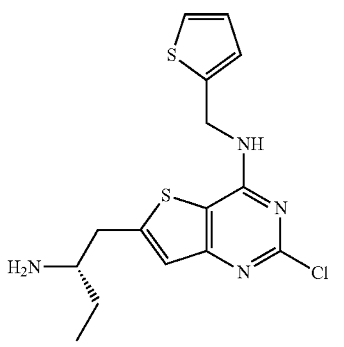
11
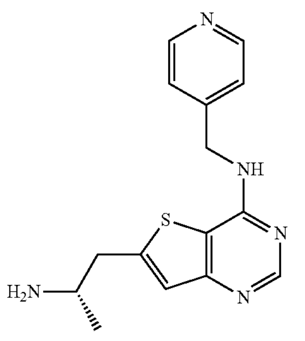

-continued
12
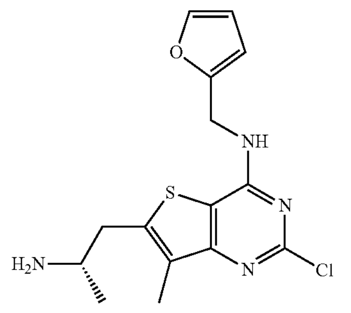
13
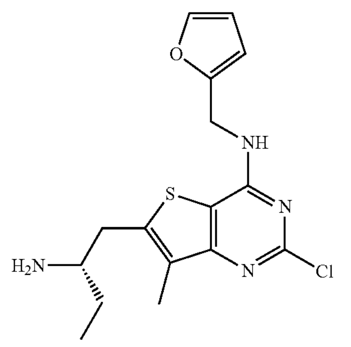
14
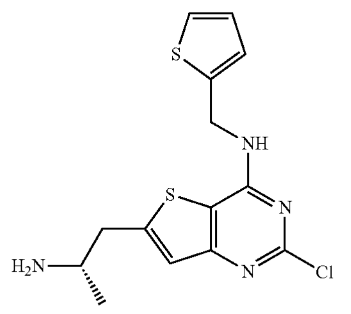
15
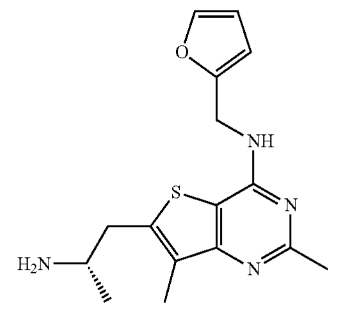
16
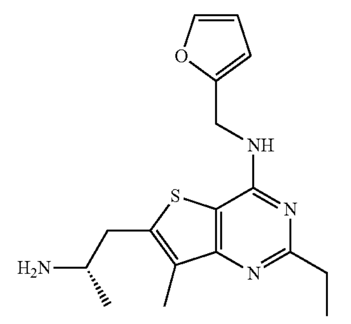
-continued
17
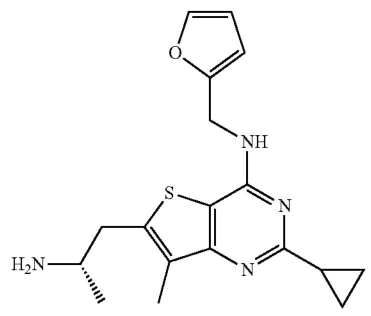
18
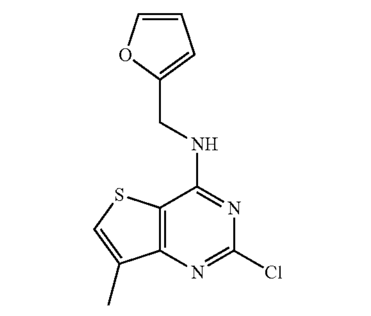
19
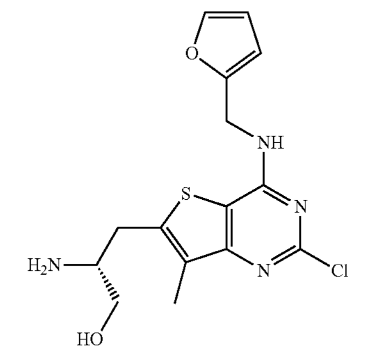
20
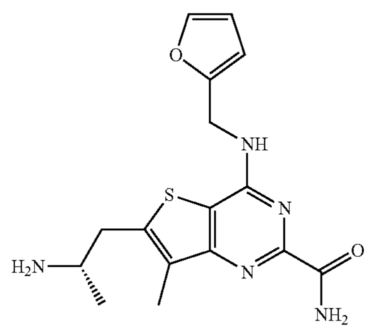
21
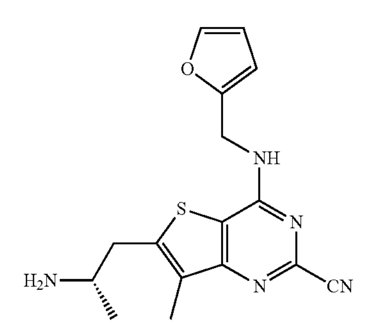

-continued
22
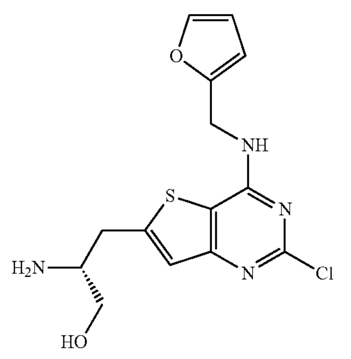
23
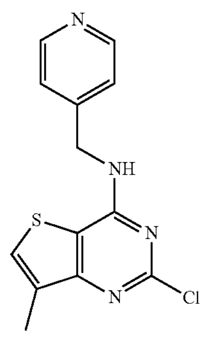
24
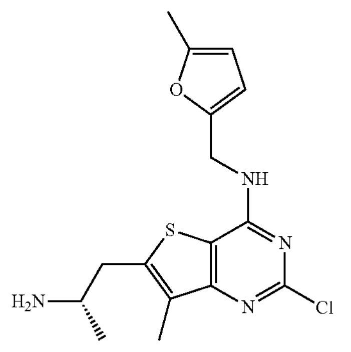
25
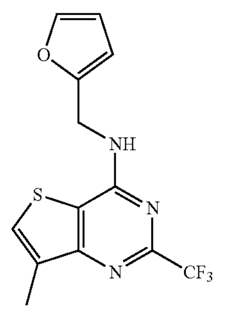
26
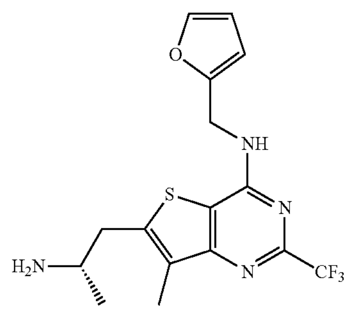
-continued
27
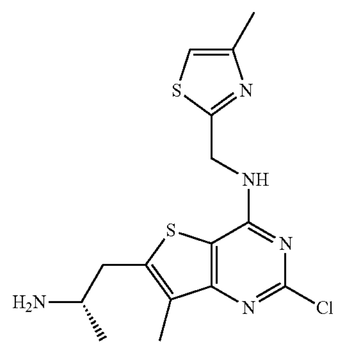
28
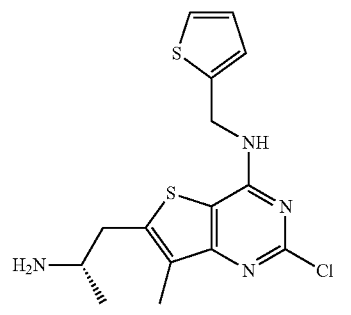
29
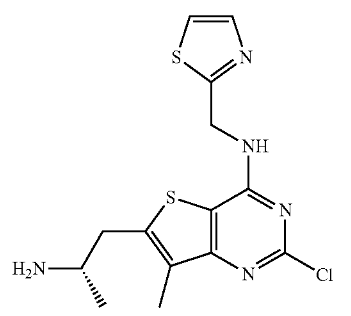
30
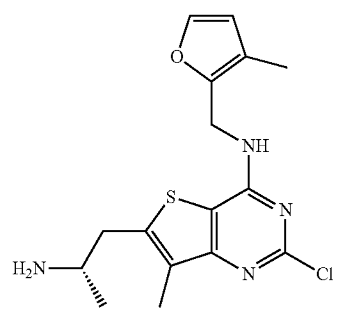
31
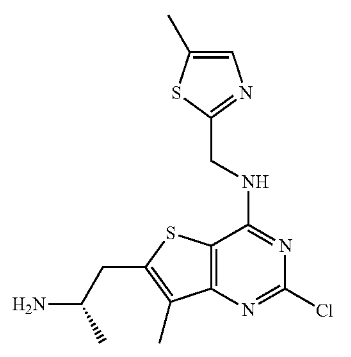

-continued
32
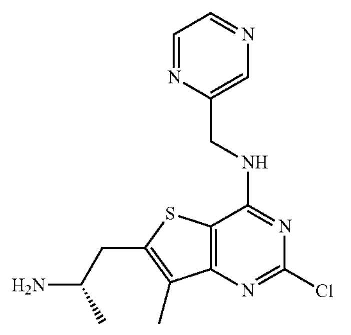
33
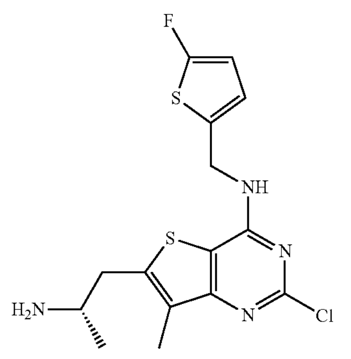
34
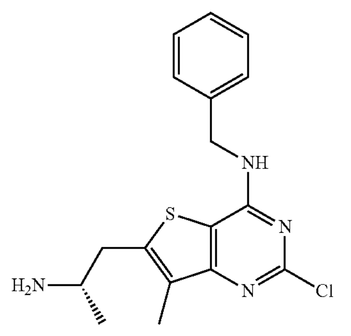
35
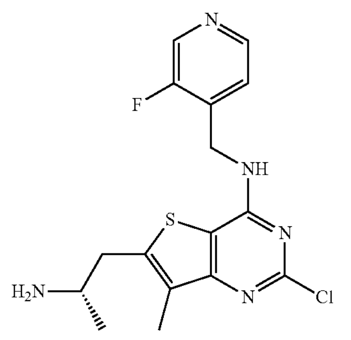
-continued
36
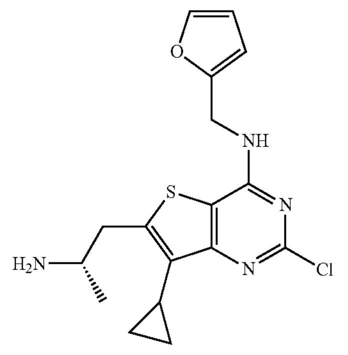
37
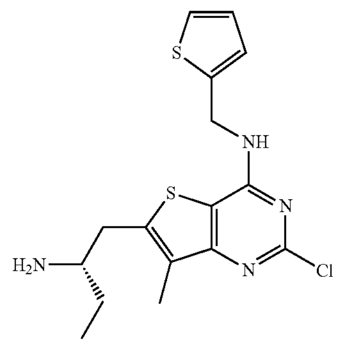
38
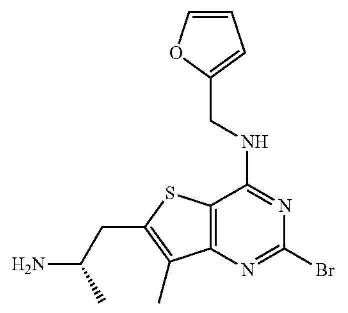
39
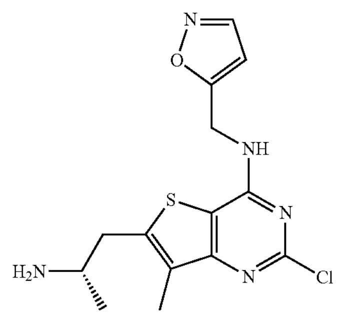
40
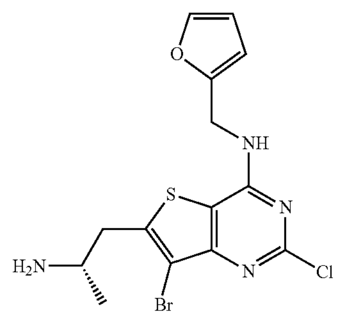

-continued
41
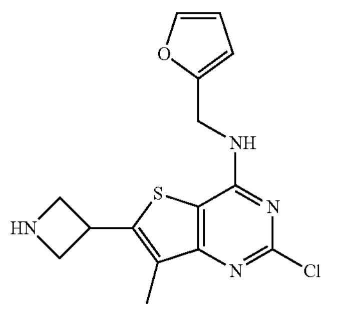
42
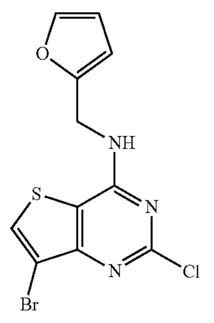
43
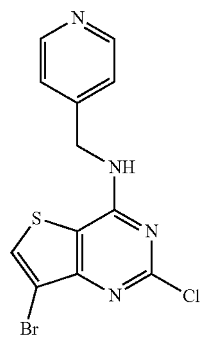
44
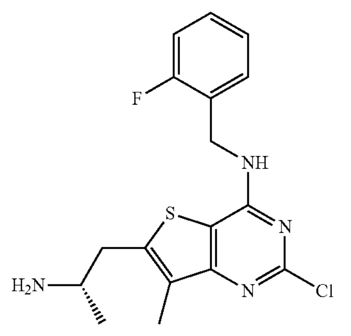
45
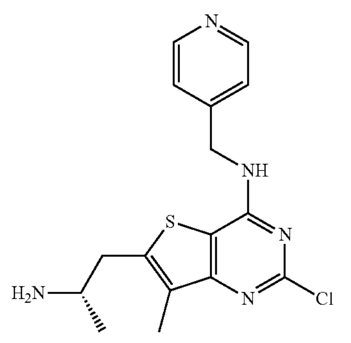
-continued
46
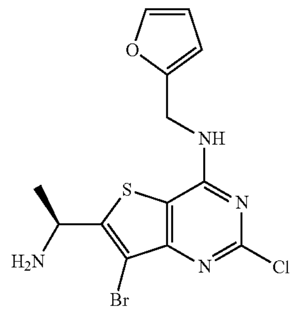
47
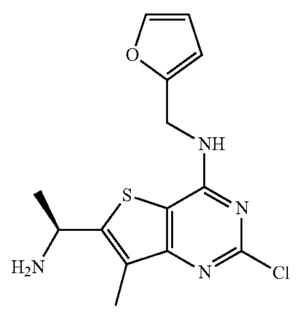
48
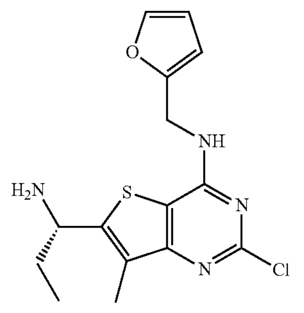
49
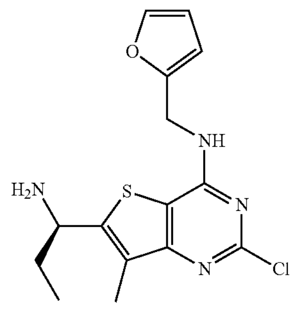
50
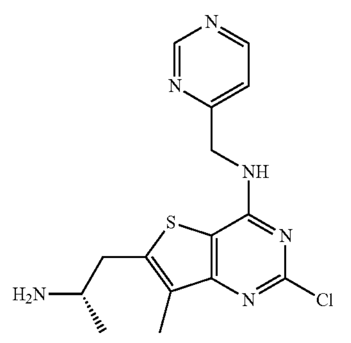

-continued
51
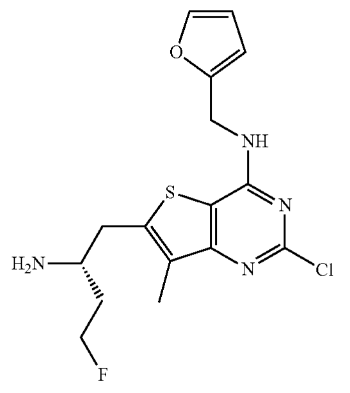
52
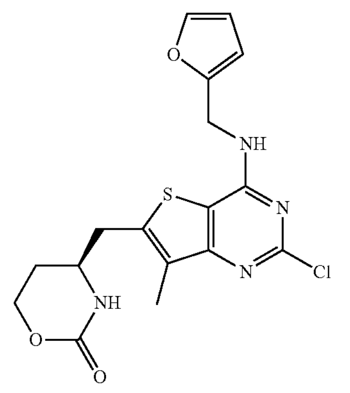
53
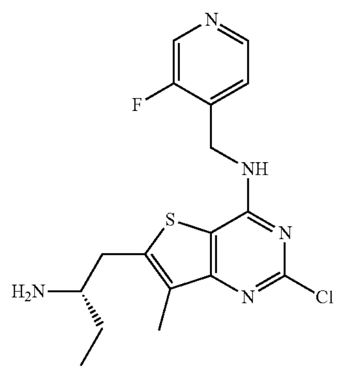
54
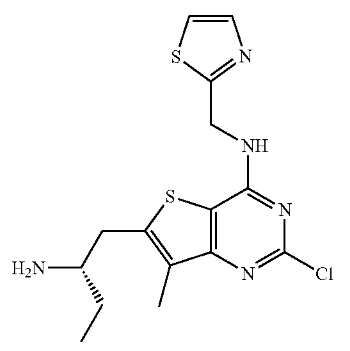
-continued
55
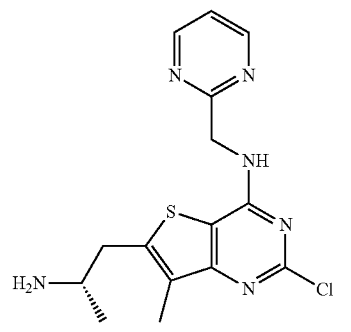
56
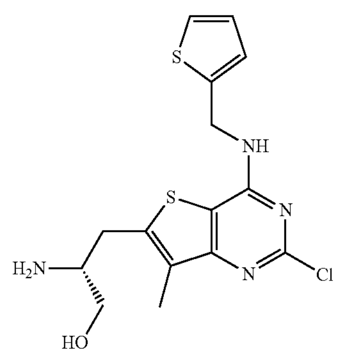
57
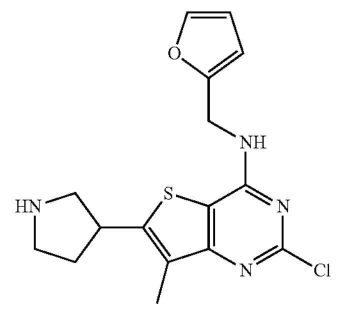
58
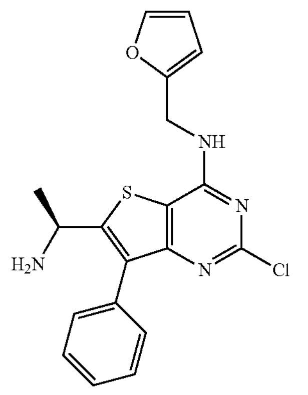

-continued
59
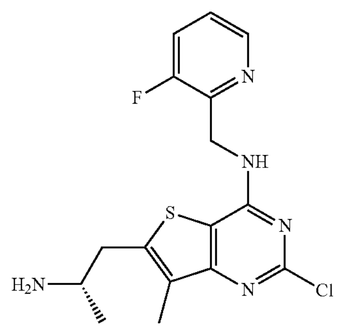
60
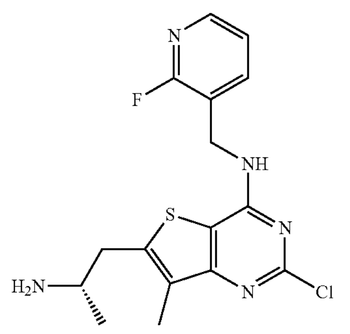
61
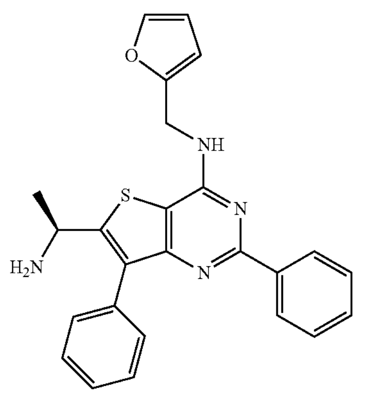
62
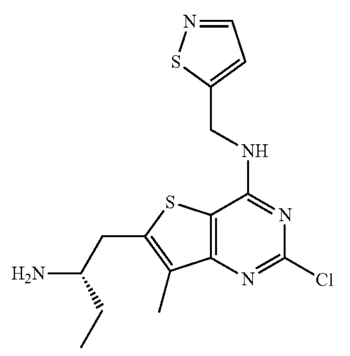
-continued
63
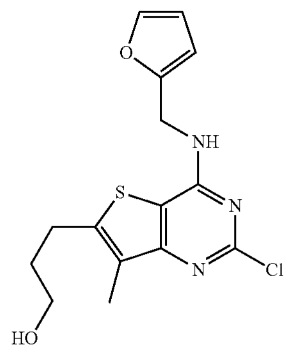
64
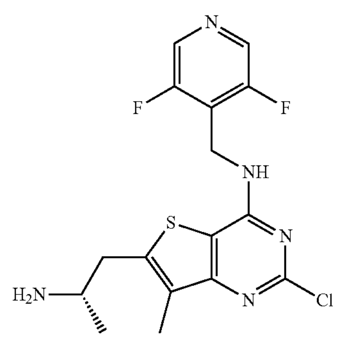
65
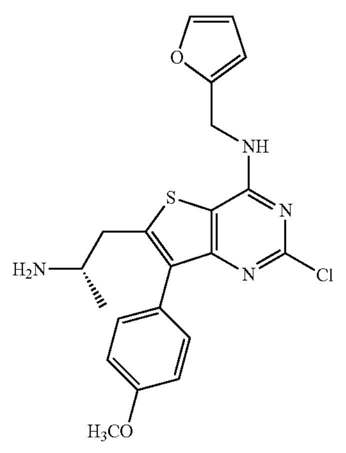
66
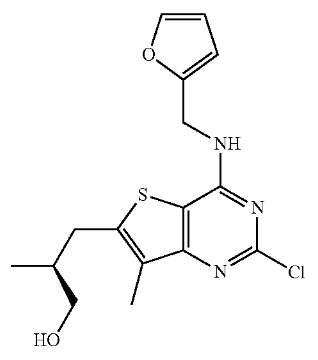

-continued
67
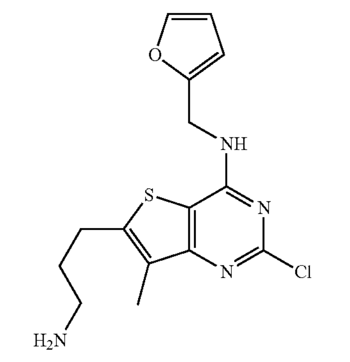
68
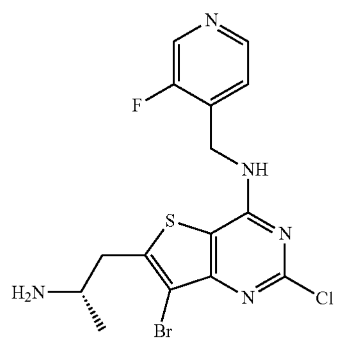
69
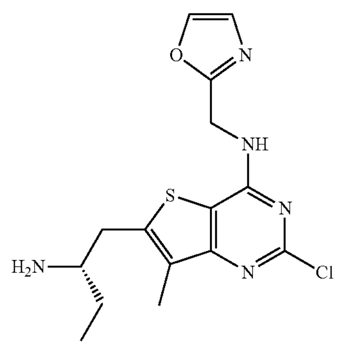
70
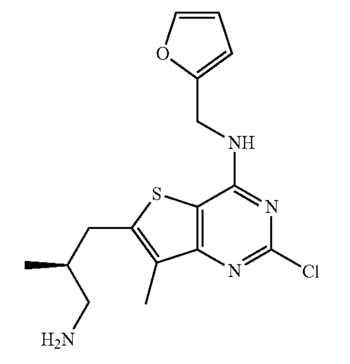
71
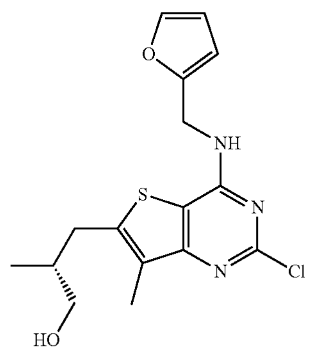
72
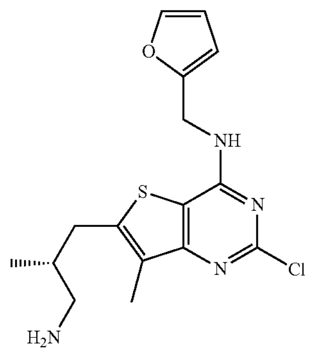
73
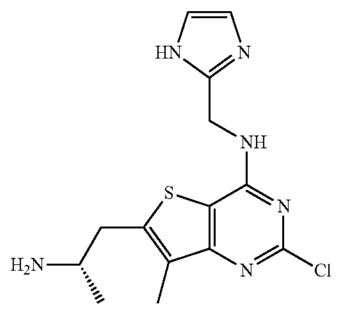
74
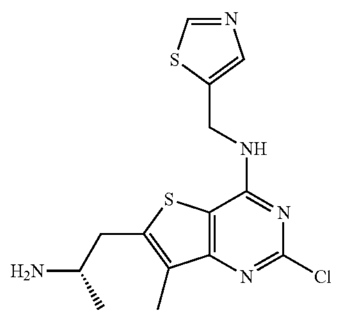
75
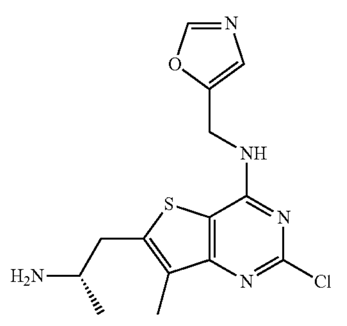

-continued
76
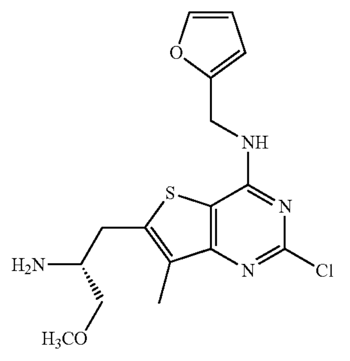
77
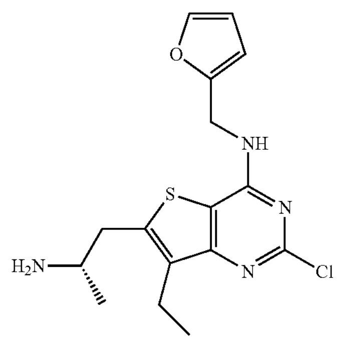
78
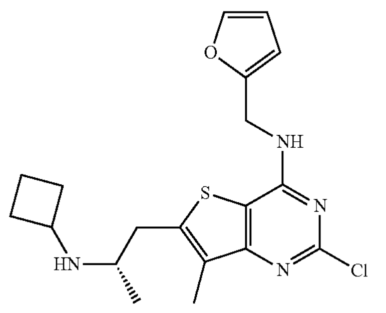
79
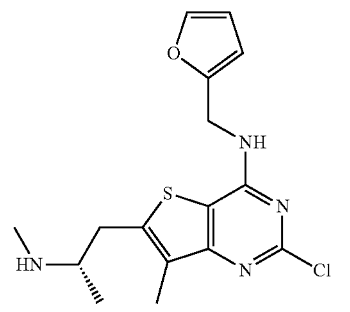
80
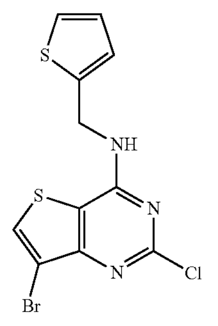
-continued
81
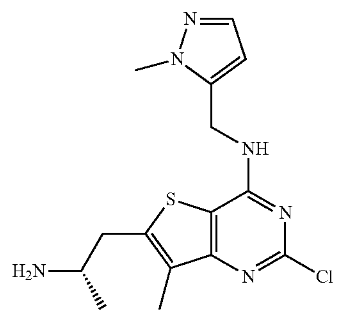
82
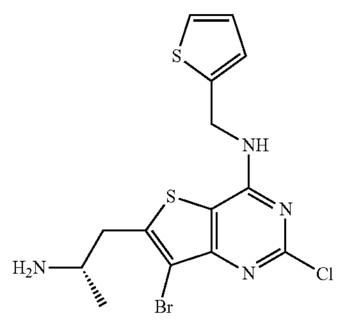
83
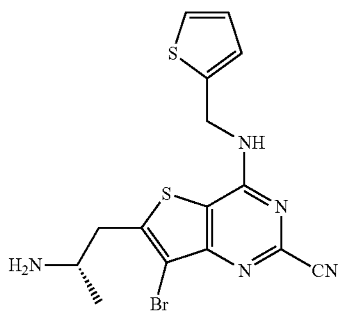
84
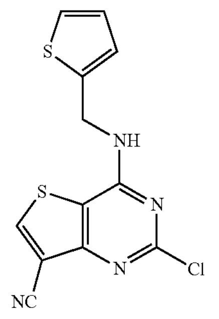
85
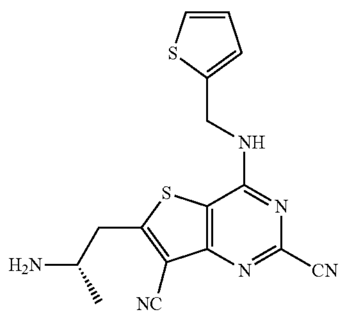

-continued
86
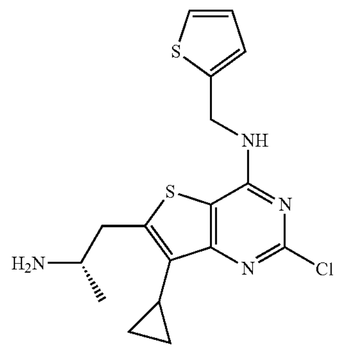
87
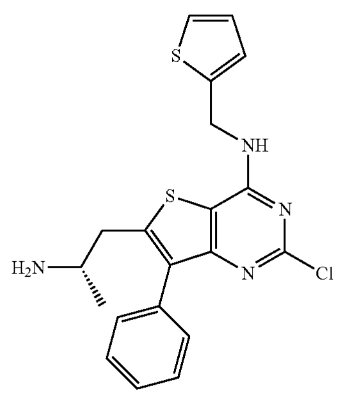
88
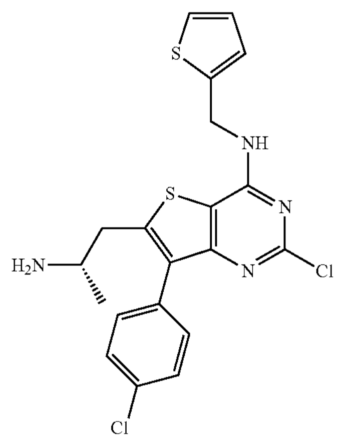
89
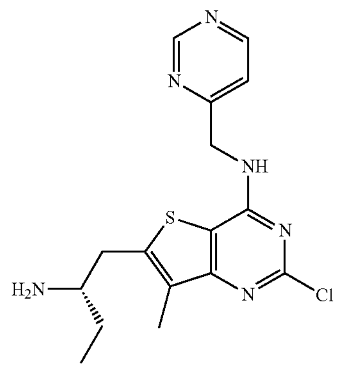
-continued
90
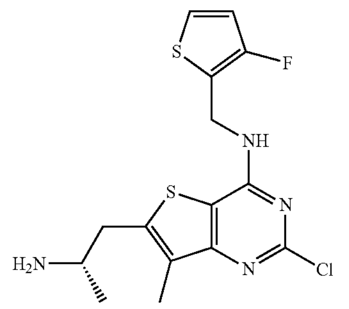
91
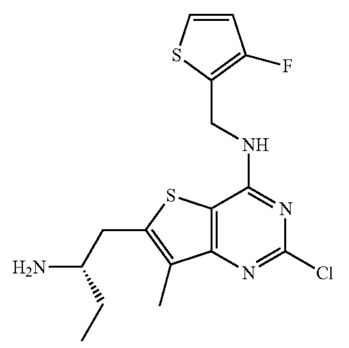
92
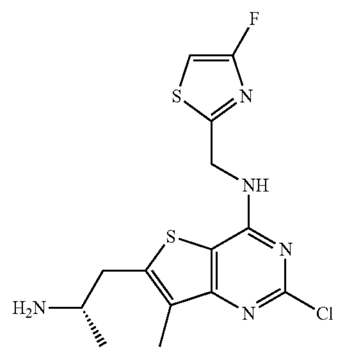
93
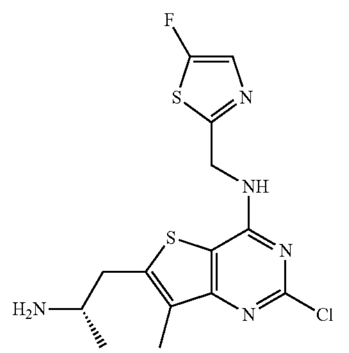
94
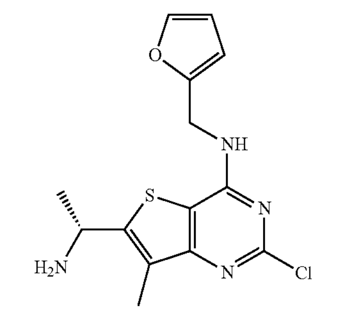

95
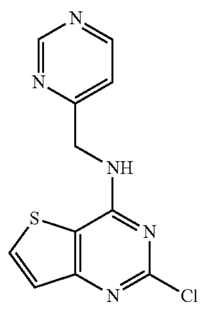
96
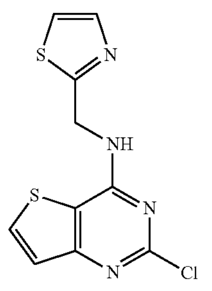
97
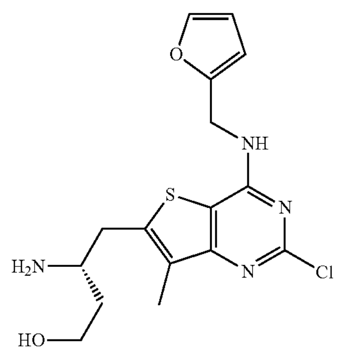
98
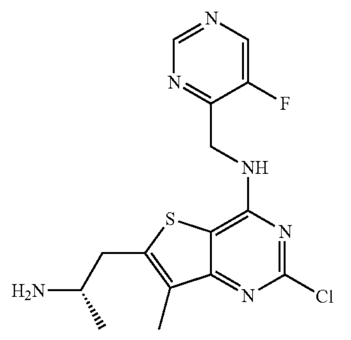
99
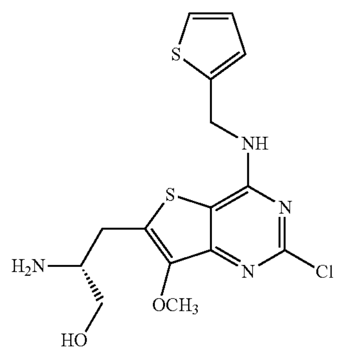
100
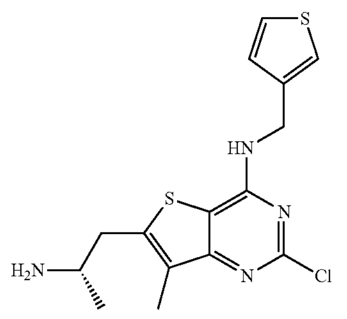
101
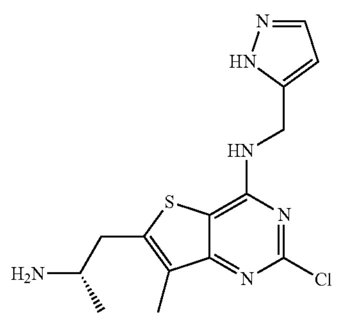
102
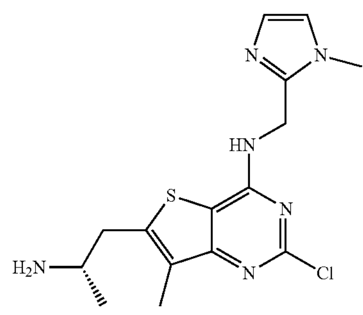
103
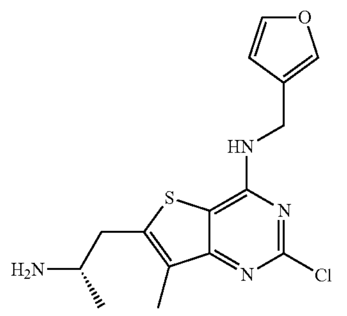
104
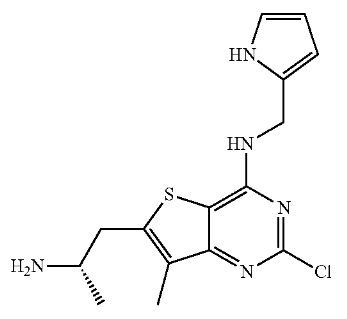

-continued
105
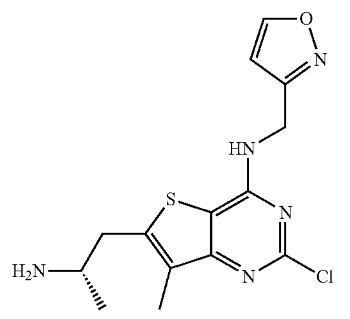
106
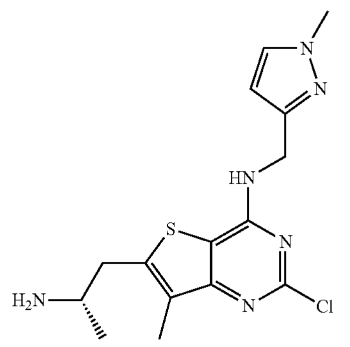
107
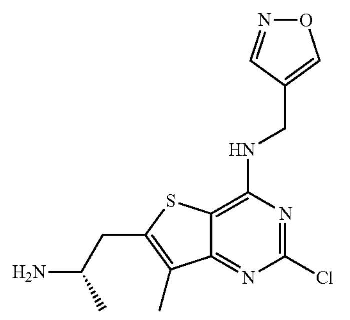
108
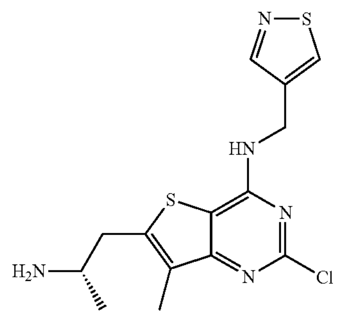
109
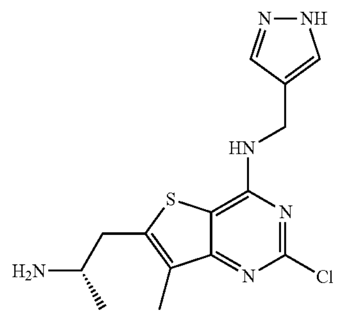
-continued
110
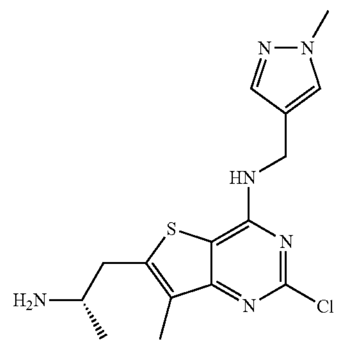
111
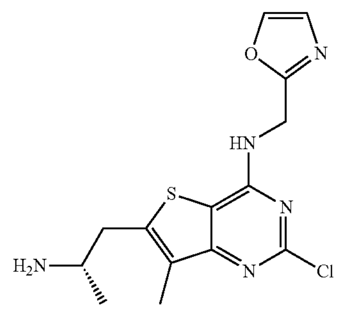
112
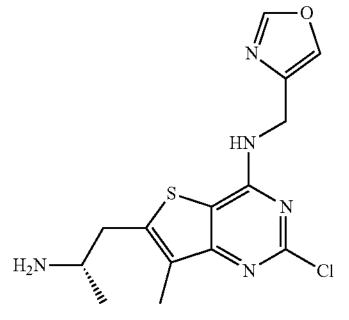
113
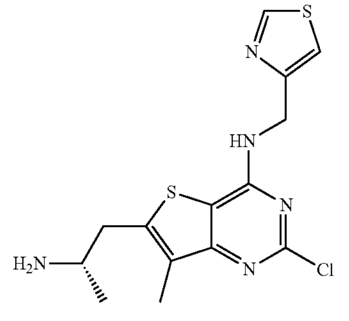
114
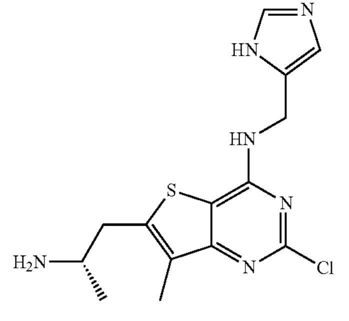

-continued
115
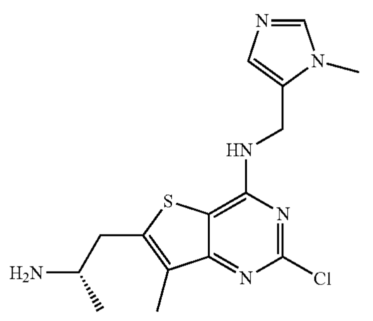
116
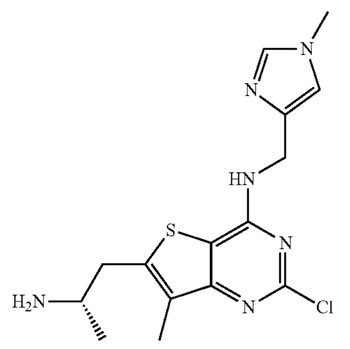
117
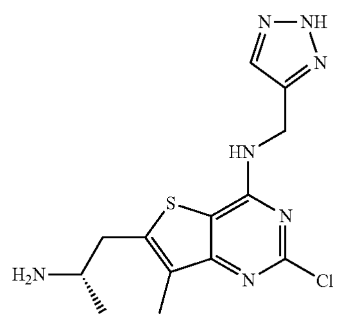
118
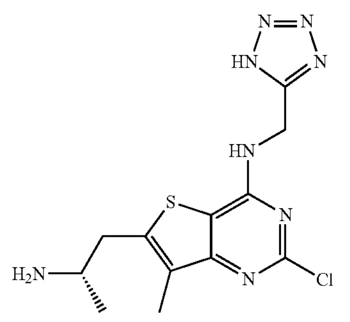
119
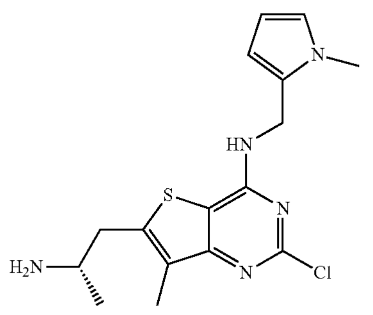
-continued
120
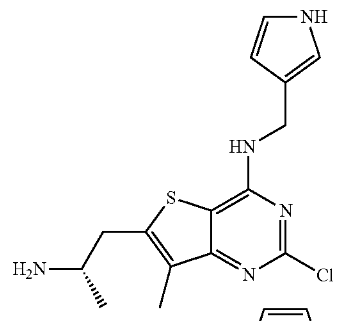
121
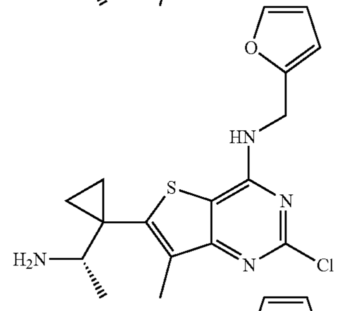
122
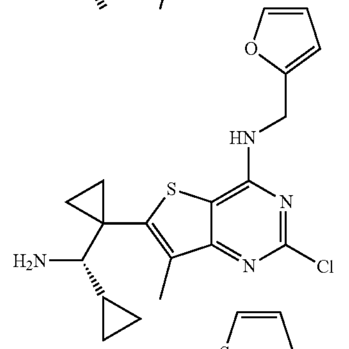
123
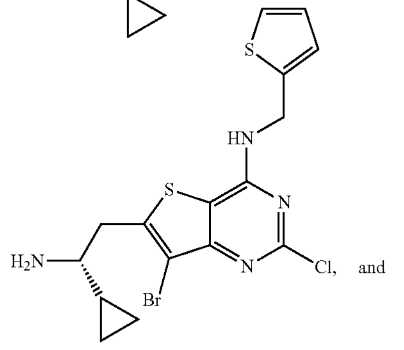
and
124
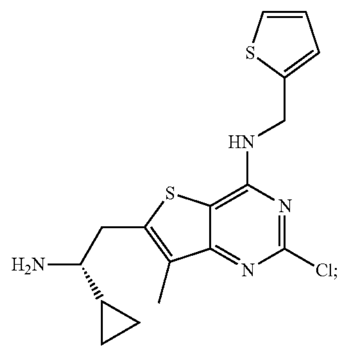
;
wherein the form of the compound is selected from the group consisting of a salt, hydrate, solvate, and tautomer form thereof.

Another aspect of the method or use includes a compound of Formula (I) or a form thereof (wherein compound number (#[1]) indicates that the salt form was isolated) includes a compound selected from the group consisting of:

| Cpd | Name |
|---|---|
| 1 | 2-chloro-N-[(pyridin-4-yl)methyl]thieno[3,2-d]pyrimidin-4-amine |
| 2 | 2-chloro-N-[(furan-2-yl)methyl]thieno[3,2-d]pyrimidin-4-amine |
| 3[1] | 6-[(2S)-2-aminopropyl]-2-chloro-N-[(furan-2-yl)methyl]thieno[3,2-d]pyrimidin-4-amine |
| 4[1] | 6-[(2S)-2-aminobutyl]-2-chloro-N-[(furan-2-yl)methyl]thieno[3,2-d]pyrimidin-4-amine |
| 5[1] | 6-[(2R)-2-amino-3-methylbutyl]-2-chloro-N-[(furan-2-yl)methyl]thieno[3,2-d]pyrimidin-4-amine |
| 6[1] | 6-[(2R,3S)-2-amino-3-methylpentyl]-2-chloro-N-[(furan-2-yl)methyl]thieno[3,2-d]pyrimidin-4-amine |
| 7[1] | 6-[(2R)-2-amino-3,3-dimethylbutyl]-2-chloro-N-[(furan-2-yl)methyl]thieno[3,2-d]pyrimidin-4-amine |
| 8[1] | 6-[(2S)-2-aminopropyl]-N-[(furan-2-yl)methyl]thieno[3,2-d]pyrimidin-4-amine |
| 9[1] | 6-[(2S)-2-aminopropyl]-2-chloro-N-[(pyridin-4-yl)methyl]thieno[3,2-d]pyrimidin-4-amine |
| 10[1] | 6-[(2S)-2-aminobutyl]-2-chloro-N-[(thiophen-2-yl)methyl]thieno[3,2-d]pyrimidin-4-amine |
| 11[1] | 6-[(2S)-2-aminopropyl]-N-[(pyridin-4-yl)methyl]thieno[3,2-d]pyrimidin-4-amine |
| 12[1] | 6-[(2S)-2-aminopropyl]-2-chloro-N-[(furan-2-yl)methyl]-7-methylthieno[3,2-d]pyrimidin-4-amine |
| 13[1] | 6-[(2S)-2-aminobutyl]-2-chloro-N-[(furan-2-yl)methyl]-7-methylthieno[3,2-d]pyrimidin-4-amine |
| 14[1] | 6-[(2S)-2-aminopropyl]-2-chloro-N-[(thiophen-2-yl)methyl]thieno[3,2-d]pyrimidin-4-amine |
| 15[1] | 6-[(2S)-2-aminopropyl]-N-[(furan-2-yl)methyl]-2,7-dimethylthieno[3,2-d]pyrimidin-4-amine |
| 16[1] | 6-[(2S)-2-aminopropyl]-2-ethyl-N-[(furan-2-yl)methyl]-7-methylthieno[3,2-d]pyrimidin-4-amine |
| 17[1] | 6-[(2S)-2-aminopropyl]-2-cyclopropyl-N-[(furan-2-yl)methyl]-7-methylthieno[3,2-d]pyrimidin-4-amine |
| 18[1] | 2-chloro-N-[(furan-2-yl)methyl]-7-methylthieno[3,2-d]pyrimidin-4-amine |
| 19[1] | (2R)-2-amino-3-(2-chloro-4-{[(furan-2-yl)methyl]amino}-7-methylthieno[3,2-d]pyrimidin-6-yl)propan-1-ol |
| 20[1] | 6-[(2S)-2-aminopropyl]-4-{[(furan-2-yl)methyl]amino}-7-methylthieno[3,2-d]pyrimidine-2-carboxamide |
| 21[1] | 6-[(2S)-2-aminopropyl]-4-{[(furan-2-yl)methyl]amino}-7-methylthieno[3,2-d]pyrimidine-2-carbonitrile |
| 22 | (2R)-2-amino-3-(2-chloro-4-{[(furan-2-yl)methyl]amino}thieno[3,2-d]pyrimidin-6-yl)propan-1-ol |
| 23 | 2-chloro-7-methyl-N-[(pyridin-4-yl)methyl]thieno[3,2-d]pyrimidin-4-amine |
| 24[1] | 6-[(2S)-2-aminopropyl]-2-chloro-7-methyl-N-[(5-methylfuran-2-yl)methyl]thieno[3,2-d]pyrimidin-4-amine |
| 25 | N-[(furan-2-yl)methyl]-7-methyl-2-(trifluoromethyl)thieno[3,2-d]pyrimidin-4-amine |
| 26[1] | 6-[(2S)-2-aminopropyl]-N-[(furan-2-yl)methyl]-7-methyl-2-(trifluoromethyl)thieno[3,2-d]pyrimidin-4-amine |
| 27[1] | 6-[(2S)-2-aminopropyl]-2-chloro-7-methyl-N-[(4-methyl-1,3-thiazol-2-yl)methyl]thieno[3,2-d]pyrimidin-4-amine |
| 28[1] | 6-[(2S)-2-aminopropyl]-2-chloro-7-methyl-N-[(thiophen-2-yl)methyl]thieno[3,2-d]pyrimidin-4-amine |
| 29[1] | 6-[(2S)-2-aminopropyl]-2-chloro-7-methyl-N-[(1,3-thiazol-2-yl)methyl]thieno[3,2-d]pyrimidin-4-amine |
| 30[1] | 6-[(2S)-2-aminopropyl]-2-chloro-7-methyl-N-[(3-methylfuran-2-yl)methyl]thieno[3,2-d]pyrimidin-4-amine |
| 31[1] | 6-[(2S)-2-aminopropyl]-2-chloro-7-methyl-N-[(5-methyl-1,3-thiazol-2-yl)methyl]thieno[3,2-d]pyrimidin-4-amine |
| 32[1] | 6-[(2S)-2-aminopropyl]-2-chloro-7-methyl-N-[(pyrazin-2-yl)methyl]thieno[3,2-d]pyrimidin-4-amine |
| 33[1] | 6-[(2S)-2-aminopropyl]-2-chloro-N-[(5-fluorothiophen-2-yl)methyl]-7-methylthieno[3,2-d]pyrimidin-4-amine |
| 34[1] | 6-[(2S)-2-aminopropyl]-N-benzyl-2-chloro-7-methylthieno[3,2-d]pyrimidin-4-amine |
| 35[1] | 6-[(2S)-2-aminopropyl]-2-chloro-N-[(3-fluoropyridin-4-yl)methyl]-7-methylthieno[3,2-d]pyrimidin-4-amine |
| 36[1] | 6-[(2S)-2-aminopropyl]-2-chloro-7-cyclopropyl-N-[(furan-2-yl)methyl]thieno[3,2-d]pyrimidin-4-amine |
| 37[1] | 6-[(2S)-2-aminobutyl]-2-chloro-7-methyl-N-[(thiophen-2-yl)methyl]thieno[3,2-d]pyrimidin-4-amine |
| 38[1] | 6-[(2S)-2-aminopropyl]-2-bromo-N-[(furan-2-yl)methyl]-7-methylthieno[3,2-d]pyrimidin-4-amine |
| 39[1] | 6-[(2S)-2-aminopropyl]-2-chloro-7-methyl-N-[(1,2-oxazol-5-yl)methyl]thieno[3,2-d]pyrimidin-4-amine |
| 40[1] | 6-[(2S)-2-aminopropyl]-7-bromo-2-chloro-N-[(furan-2-yl)methyl]thieno[3,2-d]pyrimidin-4-amine |
| 41[1] | 6-(azetidin-3-yl)-2-chloro-N-[(furan-2-yl)methyl]-7-methylthieno[3,2-d]pyrimidin-4-amine |
| 42 | 7-bromo-2-chloro-N-[(furan-2-yl)methyl]thieno[3,2-d]pyrimidin-4-amine |
| 43 | 7-bromo-2-chloro-N-[(pyridin-4-yl)methyl]thieno[3,2-d]pyrimidin-4-amine |
| 44[1] | 6-[(2S)-2-aminopropyl]-2-chloro-N-[(2-fluorophenyl)methyl]-7-methylthieno[3,2-d]pyrimidin-4-amine |

-continued

| Cpd | Name |
|---|---|
| 45[1] | 6-[(2S)-2-aminopropyl]-2-chloro-7-methyl-N-[(pyridin-4-yl)methyl]thieno[3,2-d]pyrimidin-4-amine |
| 46[1] | 6-[(1S)-1-aminoethyl]-7-bromo-2-chloro-N-[(furan-2-yl)methyl]thieno[3,2-d]pyrimidin-4-amine |
| 47[1] | 6-[(1S)-1-aminoethyl]-2-chloro-N-[(furan-2-yl)methyl]-7-methylthieno[3,2-d]pyrimidin-4-amine |
| 48[1] | 6-[(1S)-1-aminopropyl]-2-chloro-N-[(furan-2-yl)methyl]-7-methylthieno[3,2-d]pyrimidin-4-amine |
| 49[1] | 6-[(1R)-1-aminopropyl]-2-chloro-N-[(furan-2-yl)methyl]-7-methylthieno[3,2-d]pyrimidin-4-amine |
| 50[1] | 6-[(2S)-2-aminopropyl]-2-chloro-7-methyl-N-[(pyrimidin-4-yl)methyl]thieno[3,2-d]pyrimidin-4-amine |
| 51[1] | 6-[(2S)-2-amino-4-fluorobutyl]-2-chloro-N-[(furan-2-yl)methyl]-7-methylthieno[3,2-d]pyrimidin-4-amine |
| 52 | (4S)-4-[(2-chloro-4-{[(furan-2-yl)methyl]amino}-7-methylthieno[3,2-d]pyrimidin-6-yl)methyl]-1,3-oxazinan-2-one |
| 53[1] | 6-[(2S)-2-aminobutyl]-2-chloro-N-[(3-fluoropyridin-4-yl)methyl]-7-methylthieno[3,2-d]pyrimidin-4-amine |
| 54[1] | 6-[(2S)-2-aminobutyl]-2-chloro-7-methyl-N-[(1,3-thiazol-2-yl)methyl]thieno[3,2-d]pyrimidin-4-amine |
| 55[1] | 6-[(2S)-2-aminopropyl]-2-chloro-7-methyl-N-[(pyrimidin-2-yl)methyl]thieno[3,2-d]pyrimidin-4-amine |
| 56[1] | (2R)-2-amino-3-(2-chloro-7-methyl-4-{[(thiophen-2-yl)methyl]amino}thieno[3,2-d]pyrimidin-6-yl)propan-1-ol |
| 57[1] | 2-chloro-N-[(furan-2-yl)methyl]-7-methyl-6-(pyrrolidin-3-yl)thieno[3,2-d]pyrimidin-4-amine |
| 58[1] | 6-[(1S)-1-aminoethyl]-2-chloro-N-[(furan-2-yl)methyl]-7-phenylthieno[3,2-d]pyrimidin-4-amine |
| 59[1] | 6-[(2S)-2-aminopropyl]-2-chloro-N-[(3-fluoropyridin-2-yl)methyl]-7-methylthieno[3,2-d]pyrimidin-4-amine |
| 60[1] | 6-[(2S)-2-aminopropyl]-2-chloro-N-[(2-fluoropyridin-3-yl)methyl]-7-methylthieno[3,2-d]pyrimidin-4-amine |
| 61[1] | 6-[(1S)-1-aminoethyl]-N-[(furan-2-yl)methyl]-2,7-diphenylthieno[3,2-d]pyrimidin-4-amine |
| 62[1] | 6-[(2S)-2-aminobutyl]-2-chloro-7-methyl-N-[(1,2-thiazol-5-yl)methyl]thieno[3,2-d]pyrimidin-4-amine |
| 63 | 3-(2-chloro-4-{[(furan-2-yl)methyl]amino}-7-methylthieno[3,2-d]pyrimidin-6-yl)propan-1-ol |
| 64[1] | 6-[(2S)-2-aminopropyl]-2-chloro-N-[(3,5-difluoropyridin-4-yl)methyl]-7-methylthieno[3,2-d]pyrimidin-4-amine |
| 65[1] | 6-[(2S)-2-aminopropyl]-2-chloro-N-[(furan-2-yl)methyl]-7-(4-methoxyphenyl)thieno[3,2-d]pyrimidin-4-amine |
| 66 | (2S)-3-(2-chloro-4-{[(furan-2-yl)methyl]amino}-7-methylthieno[3,2-d]pyrimidin-6-yl)-2-methylpropan-1-ol |
| 67[1] | 6-(3-aminopropyl)-2-chloro-N-[(furan-2-yl)methyl]-7-methylthieno[3,2-d]pyrimidin-4-amine |
| 68[1] | 6-[(2S)-2-aminopropyl]-7-bromo-2-chloro-N-[(3-fluoropyridin-4-yl)methyl]thieno[3,2-d]pyrimidin-4-amine |
| 69[1] | 6-[(2S)-2-aminobutyl]-2-chloro-7-methyl-N-[(1,3-oxazol-2-yl)methyl]thieno[3,2-d]pyrimidin-4-amine |
| 70[1] | 6-[(2S)-3-amino-2-methylpropyl]-2-chloro-N-[(furan-2-yl)methyl]-7-methylthieno[3,2-d]pyrimidin-4-amine |
| 71 | (2R)-3-(2-chloro-4-{[(furan-2-yl)methyl]amino}-7-methylthieno[3,2-d]pyrimidin-6-yl)-2-methylpropan-1-ol |
| 72[1] | 6-[(2R)-3-amino-2-methylpropyl]-2-chloro-N-[(furan-2-yl)methyl]-7-methylthieno[3,2-d]pyrimidin-4-amine |
| 73[1] | 6-[(2S)-2-aminopropyl]-2-chloro-N-[(1H-imidazol-2-yl)methyl]-7-methylthieno[3,2-d]pyrimidin-4-amine |
| 74[1] | 6-[(2S)-2-aminopropyl]-2-chloro-7-methyl-N-[(1,3-thiazol-5-yl)methyl]thieno[3,2-d]pyrimidin-4-amine |
| 75[1] | 6-[(2S)-2-aminopropyl]-2-chloro-7-methyl-N-[(1,3-oxazol-5-yl)methyl]thieno[3,2-d]pyrimidin-4-amine |
| 76[1] | 6-[(2R)-2-amino-3-methoxypropyl]-2-chloro-N-[(furan-2-yl)methyl]-7-methylthieno[3,2-d]pyrimidin-4-amine |
| 77[1] | 6-[(2S)-2-aminopropyl]-2-chloro-7-ethyl-N-[(furan-2-yl)methyl]thieno[3,2-d]pyrimidin-4-amine |
| 78[1] | 2-chloro-6-[(2S)-2-(cyclobutylamino)propyl]-N-[(furan-2-yl)methyl]-7-methylthieno[3,2-d]pyrimidin-4-amine |
| 79[1] | 2-chloro-N-[(furan-2-yl)methyl]-7-methyl-6-[(2S)-2-(methylamino)propyl]thieno[3,2-d]pyrimidin-4-amine |
| 80 | 7-bromo-2-chloro-N-[(thiophen-2-yl)methyl]thieno[3,2-d]pyrimidin-4-amine |
| 81[1] | 6-[(2S)-2-aminopropyl]-2-chloro-7-methyl-N-[(1-methyl-1H-pyrazol-5-yl)methyl]thieno[3,2-d]pyrimidin-4-amine |
| 82[1] | 6-[(2S)-2-aminopropyl]-7-bromo-2-chloro-N-[(thiophen-2-yl)methyl]thieno[3,2-d]pyrimidin-4-amine |
| 83[1] | 6-[(2S)-2-aminopropyl]-7-bromo-4-{[(thiophen-2-yl)methyl]amino}thieno[3,2-d]pyrimidine-2-carbonitrile |

-continued

| Cpd | Name |
|---|---|
| 84 | 2-chloro-4-{[(thiophen-2-yl)methyl]amino}thieno[3,2-d]pyrimidine-7-carbonitrile |
| 85[1] | 6-[(2S)-2-aminopropyl]-4-{[(thiophen-2-yl)methyl]amino}thieno[3,2-d]pyrimidine-2,7-dicarbonitrile |
| 86[1] | 6-[(2S)-2-aminopropyl]-2-chloro-7-cyclopropyl-N-[(thiophen-2-yl)methyl]thieno[3,2-d]pyrimidin-4-amine |
| 87[1] | 6-[(2S)-2-aminopropyl]-2-chloro-7-phenyl-N-[(thiophen-2-yl)methyl]thieno[3,2-d]pyrimidin-4-amine |
| 88[1] | 6-[(2S)-2-aminopropyl]-2-chloro-7-(4-chlorophenyl)-N-[(thiophen-2-yl)methyl]thieno[3,2-d]pyrimidin-4-amine |
| 89[1] | 6-[(2S)-2-aminobutyl]-2-chloro-7-methyl-N-[(pyrimidin-4-yl)methyl]thieno[3,2-d]pyrimidin-4-amine |
| 90[1] | 6-[(2S)-2-aminopropyl]-2-chloro-N-[(3-fluorothiophen-2-yl)methyl]-7-methylthieno[3,2-d]pyrimidin-4-amine |
| 91[1] | 6-[(2S)-2-aminobutyl]-2-chloro-N-[(3-fluorothiophen-2-yl)methyl]-7-methylthieno[3,2-d]pyrimidin-4-amine |
| 92[1] | 6-[(2S)-2-aminopropyl]-2-chloro-N-[(4-fluoro-1,3-thiazol-2-yl)methyl]-7-methylthieno[3,2-d]pyrimidin-4-amine |
| 93[1] | 6-[(2S)-2-aminopropyl]-2-chloro-N-[(5-fluoro-1,3-thiazol-2-yl)methyl]-7-methylthieno[3,2-d]pyrimidin-4-amine |
| 94[1] | 6-[(1R)-1-aminoethyl]-2-chloro-N-[(furan-2-yl)methyl]-7-methylthieno[3,2-d]pyrimidin-4-amine |
| 95 | 2-chloro-N-[(pyrimidin-4-yl)methyl]thieno[3,2-d]pyrimidin-4-amine |
| 96 | 2-chloro-N-[(1,3-thiazol-2-yl)methyl]thieno[3,2-d]pyrimidin-4-amine |
| 97[1] | (3S)-3-amino-4-(2-chloro-4-{[(furan-2-yl)methyl]amino}-7-methylthieno[3,2-d]pyrimidin-6-yl)butan-1-ol |
| 98[1] | 6-[(2S)-2-aminopropyl]-2-chloro-N-[(5-fluoropyrimidin-4-yl)methyl]-7-methylthieno[3,2-d]pyrimidin-4-amine |
| 99[1] | (2R)-2-amino-3-(2-chloro-7-methoxy-4-{[(thiophen-2-yl)methyl]amino}thieno[3,2-d]pyrimidin-6-yl)propan-1-ol |
| 100 | 6-[(2S)-2-aminopropyl]-2-chloro-7-methyl-N-[(thiophen-3-yl)methyl]thieno[3,2-d]pyrimidin-4-amine |
| 101 | 6-[(2S)-2-aminopropyl]-2-chloro-7-methyl-N-[(1H-pyrazol-5-yl)methyl]thieno[3,2-d]pyrimidin-4-amine |
| 102 | 6-[(2S)-2-aminopropyl]-2-chloro-7-methyl-N-[(1-methyl-1H-imidazol-2-yl)methyl]thieno[3,2-d]pyrimidin-4-amine |
| 103 | 6-[(2S)-2-aminopropyl]-2-chloro-N-[(furan-3-yl)methyl]-7-methylthieno[3,2-d]pyrimidin-4-amine |
| 104 | 6-[(2S)-2-aminopropyl]-2-chloro-7-methyl-N-[(1H-pyrrol-2-yl)methyl]thieno[3,2-d]pyrimidin-4-amine |
| 105 | 6-[(2S)-2-aminopropyl]-2-chloro-7-methyl-N-[(1,2-oxazol-3-yl)methyl]thieno[3,2-d]pyrimidin-4-amine |
| 106 | 6-[(2S)-2-aminopropyl]-2-chloro-7-methyl-N-[(1-methyl-1H-pyrazol-3-yl)methyl]thieno[3,2-d]pyrimidin-4-amine |
| 107 | 6-[(2S)-2-aminopropyl]-2-chloro-7-methyl-N-[(1,2-oxazol-4-yl)methyl]thieno[3,2-d]pyrimidin-4-amine |
| 108 | 6-[(2S)-2-aminopropyl]-2-chloro-7-methyl-N-[(1,2-thiazol-4-yl)methyl]thieno[3,2-d]pyrimidin-4-amine |
| 109 | 6-[(2S)-2-aminopropyl]-2-chloro-7-methyl-N-[(1H-pyrazol-4-yl)methyl]thieno[3,2-d]pyrimidin-4-amine |
| 110 | 6-[(2S)-2-aminopropyl]-2-chloro-7-methyl-N-[(1-methyl-1H-pyrazol-4-yl)methyl]thieno[3,2-d]pyrimidin-4-amine |
| 111 | 6-[(2S)-2-aminopropyl]-2-chloro-7-methyl-N-[(1,3-oxazol-2-yl)methyl]thieno[3,2-d]pyrimidin-4-amine |
| 112 | 6-[(2S)-2-aminopropyl]-2-chloro-7-methyl-N-[(1,3-oxazol-4-yl)methyl]thieno[3,2-d]pyrimidin-4-amine |
| 113 | 6-[(2S)-2-aminopropyl]-2-chloro-7-methyl-N-[(1,3-thiazol-4-yl)methyl]thieno[3,2-d]pyrimidin-4-amine |
| 114 | 6-[(2S)-2-aminopropyl]-2-chloro-N-[(1H-imidazol-5-yl)methyl]-7-methylthieno[3,2-d]pyrimidin-4-amine |
| 115 | 6-[(2S)-2-aminopropyl]-2-chloro-7-methyl-N-[(1-methyl-1H-imidazol-5-yl)methyl]thieno[3,2-d]pyrimidin-4-amine |
| 116 | 6-[(2S)-2-aminopropyl]-2-chloro-7-methyl-N-[(1-methyl-1H-imidazol-4-yl)methyl]thieno[3,2-d]pyrimidin-4-amine |
| 117 | 6-[(2S)-2-aminopropyl]-2-chloro-7-methyl-N-[(2H-1,2,3-triazol-4-yl)methyl]thieno[3,2-d]pyrimidin-4-amine |
| 118 | 6-[(2S)-2-aminopropyl]-2-chloro-7-methyl-N-[(1H-tetrazol-5-yl)methyl]thieno[3,2-d]pyrimidin-4-amine |
| 119 | 6-[(2S)-2-aminopropyl]-2-chloro-7-methyl-N-[(1-methyl-1H-pyrrol-2-yl)methyl]thieno[3,2-d]pyrimidin-4-amine |
| 120[1] | 6-[(2S)-2-aminopropyl]-2-chloro-7-methyl-N-[(1H-pyrrol-3-yl)methyl]thieno[3,2-d]pyrimidin-4-amine |
| 121[1] | 6-[(S)-(1-(1-aminoethyl)cyclopropyl)]-2-chloro-N-[(furan-2-yl)methyl]-7-methylthieno[3,2-d]pyrimidin-4-amine |
| 122[1] | 6-[(S)-(1-(amino(cyclopropyl)methyl)cyclopropyl)]-2-chloro-N-[(furan-2-yl)methyl]-7-methylthieno[3,2-d]pyrimidin-4-amine |
| 123[1] | 6-[(2R)-2-amino-2-cyclopropylethyl]-7-bromo-2-chloro-N-[(thiophen-2-yl)methyl]thieno[3,2-d]pyrimidin-4-amine, and |

-continued

| Cpd | Name |
|---|---|
| 124[1] | 6-[(2R)-2-amino-2-cyclopropylethyl]-2-chloro-7-methyl-N-[(thiophen-2-yl)methyl]thieno[3,2-d]pyrimidin-4-amine; |

wherein the form of the compound is selected from the group consisting of a salt, hydrate, solvate, and tautomer form thereof.

Another aspect of the method or use includes a compound of Formula (1) or a form thereof is a compound salt selected from the group consisting of

| Cpd | Name |
|---|---|
| 3 | 6-[(2S)-2-aminopropyl]-2-chloro-N-[(furan-2-yl)methyl]thieno[3,2-d]pyrimidin-4-amine dihydrochloride |
| 4 | 6-[(2S)-2-aminobutyl]-2-chloro-N-[(furan-2-yl)methyl]thieno[3,2-d]pyrimidin-4-amine dihydrochloride |
| 5 | 6-[(2R)-2-amino-3-methylbutyl]-2-chloro-N-[(furan-2-yl)methyl]thieno[3,2-d]pyrimidin-4-amine dihydrochloride |
| 6 | 6-[(2R,3S)-2-amino-3-methylpentyl]-2-chloro-N-[(furan-2-yl)methyl]thieno[3,2-d]pyrimidin-4-amine dihydrochloride |
| 7 | 6-[(2R)-2-amino-3,3-dimethylbutyl]-2-chloro-N-[(furan-2-yl)methyl]thieno[3,2-d]pyrimidin-4-amine dihydrochloride |
| 8 | 6-[(2S)-2-aminopropyl]-N-[(furan-2-yl)methyl]thieno[3,2-d]pyrimidin-4-amine dihydrochloride |
| 9 | 6-[(2S)-2-aminopropyl]-2-chloro-N-[(pyridin-4-yl)methyl]thieno[3,2-d]pyrimidin-4-amine dihydrochloride |
| 10 | 6-[(2S)-2-aminobutyl]-2-chloro-N-[(thiophen-2-yl)methyl]thieno[3,2-d]pyrimidin-4-amine dihydrochloride |
| 11 | 6-[(2S)-2-aminopropyl]-N-[(pyridin-4-yl)methyl]thieno[3,2-d]pyrimidin-4-amine dihydrochloride |
| 12 | 6-[(2S)-2-aminopropyl]-2-chloro-N-[(furan-2-yl)methyl]-7-methylthieno[3,2-d]pyrimidin-4-amine dihydrochloride |
| 13 | 6-[(2S)-2-aminobutyl]-2-chloro-N-[(furan-2-yl)methyl]-7-methylthieno[3,2-d]pyrimidin-4-amine dihydrochloride |
| 14 | 6-[(2S)-2-aminopropyl]-2-chloro-N-[(thiophen-2-yl)methyl]thieno[3,2-d]pyrimidin-4-amine dihydrochloride |
| 15 | 6-[(2S)-2-aminopropyl]-N-[(furan-2-yl)methyl]-2,7-dimethylthieno[3,2-d]pyrimidin-4-amine dihydrochloride |
| 16 | 6-[(2S)-2-aminopropyl]-2-ethyl-N-[(furan-2-yl)methyl]-7-methylthieno[3,2-d]pyrimidin-4-amine dihydrochloride |
| 17 | 6-[(2S)-2-aminopropyl]-2-cyclopropyl-N-[(furan-2-yl)methyl]-7-methylthieno[3,2-d]pyrimidin-4-amine dihydrochloride |
| 18 | 2-chloro-N-[(furan-2-yl)methyl]-7-methylthieno[3,2-d]pyrimidin-4-amine hydrochloride |
| 19 | (2R)-2-amino-3-(2-chloro-4-{[(furan-2-yl)methyl]amino}-7-methylthieno[3,2-d]pyrimidin-6-yl)propan-1-ol dihydrochloride |
| 20 | 6-[(2S)-2-aminopropyl]-4-{[(furan-2-yl)methyl]amino}-7-methylthieno[3,2-d]pyrimidine-2-carboxamide trifluoroacetate |
| 21 | 6-[(2S)-2-aminopropyl]-4-{[(furan-2-yl)methyl]amino}-7-methylthieno[3,2-d]pyrimidine-2-carbonitrile trifluoroacetate |
| 24 | 6-[(2S)-2-aminopropyl]-2-chloro-7-methyl-N-[(5-methylfuran-2-yl)methyl]thieno[3,2-d]pyrimidin-4-amine dihydrochloride |
| 26 | 6-[(2S)-2-aminopropyl]-N-[(furan-2-yl)methyl]-7-methyl-2-(trifluoromethyl)thieno[3,2-d]pyrimidin-4-amine dihydrochloride |
| 27 | 6-[(2S)-2-aminopropyl]-2-chloro-7-methyl-N-[(4-methyl-1,3-thiazol-2-yl)methyl]thieno[3,2-d]pyrimidin-4-amine dihydrochloride |
| 28 | 6-[(2S)-2-aminopropyl]-2-chloro-7-methyl-N-[(thiophen-2-yl)methyl]thieno[3,2-d]pyrimidin-4-amine dihydrochloride |
| 29 | 6-[(2S)-2-aminopropyl]-2-chloro-7-methyl-N-[(1,3-thiazol-2-yl)methyl]thieno[3,2-d]pyrimidin-4-amine trifluoroacetate |
| 30 | 6-[(2S)-2-aminopropyl]-2-chloro-7-methyl-N-[(3-methylfuran-2-yl)methyl]thieno[3,2-d]pyrimidin-4-amine dihydrochloride |
| 31 | 6-[(2S)-2-aminopropyl]-2-chloro-7-methyl-N-[(5-methyl-1,3-thiazol-2-yl)methyl]thieno[3,2-d]pyrimidin-4-amine dihydrochloride |
| 32 | 6-[(2S)-2-aminopropyl]-2-chloro-7-methyl-N-[(pyrazin-2-yl)methyl]thieno[3,2-d]pyrimidin-4-amine dihydrochloride |
| 33 | 6-[(2S)-2-aminopropyl]-2-chloro-N-[(5-fluorothiophen-2-yl)methyl]-7-methylthieno[3,2-d]pyrimidin-4-amine dihydrochloride |
| 34 | 6-[(2S)-2-aminopropyl]-N-benzyl-2-chloro-7-methylthieno[3,2-d]pyrimidin-4-amine dihydrochloride |
| 35 | 6-[(2S)-2-aminopropyl]-2-chloro-N-[(3-fluoropyridin-4-yl)methyl]-7-methylthieno[3,2-d]pyrimidin-4-amine dihydrochloride |
| 36 | 6-[(2S)-2-aminopropyl]-2-chloro-7-cyclopropyl-N-[(furan-2-yl)methyl]thieno[3,2-d]pyrimidin-4-amine trifluoroacetate |
| 37 | 6-[(2S)-2-aminobutyl]-2-chloro-7-methyl-N-[(thiophen-2-yl)methyl]thieno[3,2-d]pyrimidin-4-amine dihydrochloride |

-continued

| Cpd | Name |
|---|---|
| 38 | 6-[(2S)-2-aminopropyl]-2-bromo-N-[(furan-2-yl)methyl]-7-methylthieno[3,2-d]pyrimidin-4-amine trifluoroacetate |
| 39 | 6-[(2S)-2-aminopropyl]-2-chloro-7-methyl-N-[(1,2-oxazol-5-yl)methyl]thieno[3,2-d]pyrimidin-4-amine hydrochloride |
| 40 | 6-[(2S)-2-aminopropyl]-7-bromo-2-chloro-N-[(furan-2-yl)methyl]thieno[3,2-d]pyrimidin-4-amine dihydrochloride |
| 41 | 6-(azetidin-3-yl)-2-chloro-N-[(furan-2-yl)methyl]-7-methylthieno[3,2-d]pyrimidin-4-amine trifluoroacetate |
| 44 | 6-[(2S)-2-aminopropyl]-2-chloro-N-[(2-fluorophenyl)methyl]-7-methylthieno[3,2-d]pyrimidin-4-amine dihydrochloride |
| 45 | 6-[(2S)-2-aminopropyl]-2-chloro-7-methyl-N-[(pyridin-4-yl)methyl]thieno[3,2-d]pyrimidin-4-amine dihydrochloride |
| 46 | 6-[(1S)-1-aminoethyl]-7-bromo-2-chloro-N-[(furan-2-yl)methyl]thieno[3,2-d]pyrimidin-4-amine hydrochloride |
| 47 | 6-[(1S)-1-aminoethyl]-2-chloro-N-[(furan-2-yl)methyl]-7-methylthieno[3,2-d]pyrimidin-4-amine hydrochloride |
| 48 | 6-[(1S)-1-aminopropyl]-2-chloro-N-[(furan-2-yl)methyl]-7-methylthieno[3,2-d]pyrimidin-4-amine hydrochloride |
| 49 | 6-[(1R)-1-aminopropyl]-2-chloro-N-[(furan-2-yl)methyl]-7-methylthieno[3,2-d]pyrimidin-4-amine hydrochloride |
| 50 | 6-[(2S)-2-aminopropyl]-2-chloro-7-methyl-N-[(pyrimidin-4-yl)methyl]thieno[3,2-d]pyrimidin-4-amine dihydrochloride |
| 51 | 6-[(2S)-2-amino-4-fluorobutyl]-2-chloro-N-[(furan-2-yl)methyl]-7-methylthieno[3,2-d]pyrimidin-4-amine dihydrochloride |
| 53 | 6-[(2S)-2-aminobutyl]-2-chloro-N-[(3-fluoropyridin-4-yl)methyl]-7-methylthieno[3,2-d]pyrimidin-4-amine dihydrochloride |
| 54 | 6-[(2S)-2-aminobutyl]-2-chloro-7-methyl-N-[(1,3-thiazol-2-yl)methyl]thieno[3,2-d]pyrimidin-4-amine dihydrochloride |
| 55 | 6-[(2S)-2-aminopropyl]-2-chloro-7-methyl-N-[(pyrimidin-2-yl)methyl]thieno[3,2-d]pyrimidin-4-amine dihydrochloride |
| 56 | (2R)-2-amino-3-(2-chloro-7-methyl-4-{[(thiophen-2-yl)methyl]amino}thieno[3,2-d]pyrimidin-6-yl)propan-1-ol dihydrochloride |
| 57 | 2-chloro-N-[(furan-2-yl)methyl]-7-methyl-6-(pyrrolidin-3-yl)thieno[3,2-d]pyrimidin-4-amine formate |
| 58 | 6-[(1S)-1-aminoethyl]-2-chloro-N-[(furan-2-yl)methyl]-7-phenylthieno[3,2-d]pyrimidin-4-amine formate |
| 59 | 6-[(2S)-2-aminopropyl]-2-chloro-N-[(3-fluoropyridin-2-yl)methyl]-7-methylthieno[3,2-d]pyrimidin-4-amine dihydrochloride |
| 60 | 6-[(2S)-2-aminopropyl]-2-chloro-N-[(2-fluoropyridin-3-yl)methyl]-7-methylthieno[3,2-d]pyrimidin-4-amine dihydrochloride |
| 61 | 6-[(1S)-1-aminoethyl]-N-[(furan-2-yl)methyl]-2,7-diphenylthieno[3,2-d]pyrimidin-4-amine formate |
| 62 | 6-[(2S)-2-aminobutyl]-2-chloro-7-methyl-N-[(1,2-thiazol-5-yl)methyl]thieno[3,2-d]pyrimidin-4-amine formate |
| 64 | 6-[(2S)-2-aminopropyl]-2-chloro-N-[(3,5-difluoropyridin-4-yl)methyl]-7-methylthieno[3,2-d]pyrimidin-4-amine dihydrochloride |
| 65 | 6-[(2S)-2-aminopropyl]-2-chloro-N-[(furan-2-yl)methyl]-7-(4-methoxyphenyl)thieno[3,2-d]pyrimidin-4-amine formate |
| 67 | 6-(3-aminopropyl)-2-chloro-N-[(furan-2-yl)methyl]-7-methylthieno[3,2-d]pyrimidin-4-amine hydrochloride |
| 68 | 6-[(2S)-2-aminopropyl]-7-bromo-2-chloro-N-[(3-fluoropyridin-4-yl)methyl]thieno[3,2-d]pyrimidin-4-amine dihydrochloride |
| 69 | 6-[(2S)-2-aminobutyl]-2-chloro-7-methyl-N-[(1,3-oxazol-2-yl)methyl]thieno[3,2-d]pyrimidin-4-amine dihydrochloride |
| 70 | 6-[(2S)-3-amino-2-methylpropyl]-2-chloro-N-[(furan-2-yl)methyl]-7-methylthieno[3,2-d]pyrimidin-4-amine hydrochloride |
| 72 | 6-[(2R)-3-amino-2-methylpropyl]-2-chloro-N-[(furan-2-yl)methyl]-7-methylthieno[3,2-d]pyrimidin-4-amine hydrochloride |
| 73 | 6-[(2S)-2-aminopropyl]-2-chloro-N-[(1H-imidazol-2-yl)methyl]-7-methylthieno[3,2-d]pyrimidin-4-amine dihydrochloride |
| 74 | 6-[(2S)-2-aminopropyl]-2-chloro-7-methyl-N-[(1,3-thiazol-5-yl)methyl]thieno[3,2-d]pyrimidin-4-amine dihydrochloride |
| 75 | 6-[(2S)-2-aminopropyl]-2-chloro-7-methyl-N-[(1,3-oxazol-5-yl)methyl]thieno[3,2-d]pyrimidin-4-amine dihydrochloride |
| 76 | 6-[(2R)-2-amino-3-methoxypropyl]-2-chloro-N-[(furan-2-yl)methyl]-7-methylthieno[3,2-d]pyrimidin-4-amine dihydrochloride |
| 77 | 6-[(2S)-2-aminopropyl]-2-chloro-7-ethyl-N-[(furan-2-yl)methyl]thieno[3,2-d]pyrimidin-4-amine hydrochloride |
| 78 | 2-chloro-6-[(2S)-2-(cyclobutylamino)propyl]-N-[(furan-2-yl)methyl]-7-methylthieno[3,2-d]pyrimidin-4-amine formate |
| 79 | 2-chloro-N-[(furan-2-yl)methyl]-7-methyl-6-[(2S)-2-(methylamino)propyl]thieno[3,2-d]pyrimidin-4-amine hydrochloride |
| 81 | 6-[(2S)-2-aminopropyl]-2-chloro-7-methyl-N-[(1-methyl-1H-pyrazol-5-yl)methyl]thieno[3,2-d]pyrimidin-4-amine hydrochloride |
| 82 | 6-[(2S)-2-aminopropyl]-7-bromo-2-chloro-N-[(thiophen-2-yl)methyl]thieno[3,2-d]pyrimidin-4-amine hydrochloride |

-continued

| Cpd | Name |
|---|---|
| 83 | 6-[(2S)-2-aminopropyl]-7-bromo-4-{[(thiophen-2-yl)methyl]amino}thieno[3,2-d]pyrimidine-2-carbonitrile formate |
| 85 | 6-[(2S)-2-aminopropyl]-4-{[(thiophen-2-yl)methyl]amino}thieno[3,2-d]pyrimidine-2,7-dicarbonitrile hydrochloride |
| 86 | 6-[(2S)-2-aminopropyl]-2-chloro-7-cyclopropyl-N-[(thiophen-2-yl)methyl]thieno[3,2-d]pyrimidin-4-amine formate |
| 87 | 6-[(2S)-2-aminopropyl]-2-chloro-7-phenyl-N-[(thiophen-2-yl)methyl]thieno[3,2-d]pyrimidin-4-amine hydrochloride |
| 88 | 6-[(2S)-2-aminopropyl]-2-chloro-7-(4-chlorophenyl)-N-[(thiophen-2-yl)methyl]thieno[3,2-d]pyrimidin-4-amine hydrochloride |
| 89 | 6-[(2S)-2-aminobutyl]-2-chloro-7-methyl-N-[(pyrimidin-4-yl)methyl]thieno[3,2-d]pyrimidin-4-amine dihydrochloride |
| 90 | 6-[(2S)-2-aminopropyl]-2-chloro-N-[(3-fluorothiophen-2-yl)methyl]-7-methylthieno[3,2-d]pyrimidin-4-amine dihydrochloride |
| 91 | 6-[(2S)-2-aminobutyl]-2-chloro-N-[(3-fluorothiophen-2-yl)methyl]-7-methylthieno[3,2-d]pyrimidin-4-amine dihydrochloride |
| 92 | 6-[(2S)-2-aminopropyl]-2-chloro-N-[(4-fluoro-1,3-thiazol-2-yl)methyl]-7-methylthieno[3,2-d]pyrimidin-4-amine dihydrochloride |
| 93 | 6-[(2S)-2-aminopropyl]-2-chloro-N-[(5-fluoro-1,3-thiazol-2-yl)methyl]-7-methylthieno[3,2-d]pyrimidin-4-amine dihydrochloride |
| 94 | 6-[(1R)-1-aminoethyl]-2-chloro-N-[(furan-2-yl)methyl]-7-methylthieno[3,2-d]pyrimidin-4-amine hydrochloride |
| 97 | (3S)-3-amino-4-(2-chloro-4-{[(furan-2-yl)methyl]amino}-7-methylthieno[3,2-d]pyrimidin-6-yl)butan-1-ol dihydrochloride |
| 98 | 6-[(2S)-2-aminopropyl]-2-chloro-N-[(5-fluoropyrimidin-4-yl)methyl]-7-methylthieno[3,2-d]pyrimidin-4-amine formate |
| 99 | (2R)-2-amino-3-(2-chloro-7-methoxy-4-{[(thiophen-2-yl)methyl]amino}thieno[3,2-d]pyrimidin-6-yl)propan-1-ol dihydrochloride |
| 121 | 6-[(S)-(1-(1-aminoethyl)cyclopropyl)]-2-chloro-N-[(furan-2-yl)methyl]-7-methylthieno[3,2-d]pyrimidin-4-amine formate |
| 122 | 6-[(S)-(1-(amino(cyclopropyl)methyl)cyclopropyl)]-2-chloro-N-[(furan-2-yl)methyl]-7-methylthieno[3,2-d]pyrimidin-4-amine formate |
| 123 | 6-[(2R)-2-amino-2-cyclopropylethyl]-7-bromo-2-chloro-N-[(thiophen-2-yl)methyl]thieno[3,2-d]pyrimidin-4-amine dihydrochloride, and |
| 124 | 6-[(2R)-2-amino-2-cyclopropylethyl]-2-chloro-7-methyl-N-[(thiophen-2-yl)methyl]thieno[3,2-d]pyrimidin-4-amine dihydrochloride; |

wherein the form of the compound is selected rom the group consisting of hydrate, solvate, and tautomer form thereof.

One aspect of the method or use includes the compound of Formula (1) or a form thereof, wherein exon 4 skipping in the ATXN3 pre-mRNA is induced during the splicing process.

One aspect of the method or use includes the compound of Formula (1) or a form thereof, wherein levels of ATXN-3 mRNA are decreased.

One aspect of the method or use includes the compound of Formula (1) or a form thereof, wherein ATXN3 protein is decreased.

One aspect of the present description relates to a pharmaceutical composition comprising a compound of Formula (I) or a form thereof and at least one pharmaceutically acceptable excipient for administering to a subject for the treatment of spinocerebellar ataxia type 3 (SCA3), also known as Machado-Joseph disease (MJD).

One aspect of the present description relates to the manufacture of a medicament for the treatment of spinocerebellar ataxia type 3 (SCA3), also known as Machado--Joseph disease (MJD), in a subject comprising a compound of Formula (I) or a form thereof and at least one pharmaceutically acceptable excipient.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Chemical Definitions

The chemical terms used above and throughout the description herein, unless specifically defined otherwise, shall be understood by one of ordinary skill in the art to have the following indicated meanings.

As used herein, the term "$C_{1-6}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), and the like. In certain aspects, $C_{1-6}$alkyl includes, but is not limited to, $C_{1-6}$alkyl, $C_{1-4}$alkyl and the like. A $C_{1-6}$alkyl radical is optionally substituted with substituent species as described herein where allowed by available valences.

As used herein, the term "hetero-$C_{1-6}$alkyl" generally refers to saturated hydrocarbon radicals having from one to six carbon atoms in a straight or branched chain configuration, in which one or more heteroatoms, such as an O, S or N atom, are members in the chain, including, but not limited to, but not limited to, hetero-methyl, hetero-ethyl, hetero-propyl, hetero-butyl, hetero-pentyl, hetero-hexyl and the like. In certain aspects, hetero-$C_{1-6}$alkyl includes, but is not limited to, hetero-$C_{2-6}$alkyl, hetero-$C_{1-4}$alkyl, hetero-$C_{2-4}$alkyl and the like. A hetero-$C_{1-6}$alkyl radical is optionally substituted with substituent species as described herein where allowed by available valences.

As used herein, the term "$C_{2-6}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In certain aspects, $C_{2-6}$alkenyl includes, but is not limited to, $C_{2-6}$alkenyl, $C_{2-4}$alkenyl and the like. A $C_{2-6}$alkenyl radical is optionally substituted with substituent species as described herein where allowed by available valences.

As used herein, the term "$C_{2-6}$alkynyl" generally refers to partially unsaturated hydrocarbon radicals having from two to eight carbon atoms in a straight or branched chain configuration and one or more carbon-carbon triple bonds therein, including, but not limited to, ethynyl (also referred to as acetylenyl), propynyl, butynyl and the like. In certain aspects, $C_{2-6}$alkynyl includes, but is not limited to, $C_{2-6}$alkynyl, $C_{2-4}$alkynyl and the like. A $C_{2-6}$alkynyl radical is optionally substituted with substituent species as described herein where allowed by available valences.

As used herein, the term "$C_{1-6}$alkoxy" generally refers to saturated hydrocarbon radicals having from one to eight carbon atoms in a straight or branched chain configuration of the formula: —O—$C_{1-6}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In certain aspects, $C_{1-6}$alkoxy includes, but is not limited to, $C_{1-6}$alkoxy, $C_{1-4}$alkoxy and the like. A $C_{1-6}$alkoxy radical is optionally substituted with substituent species as described herein where allowed by available valences.

As used herein, the term "oxo" refers to a radical of the formula: =0.

As used herein, the term "carboxyl" refers to a radical of the formula: —COOH, —C(O)OH or —$CO_2$H.

As used herein, the term "carbamoyl" refers to a radical of the formula: —C(O)$NH_2$.

As used herein, the term "$C_{3-10}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In certain aspects, $C_{3-10}$cycloalkyl includes, but is not limited to, $C_{3-8}$cycloalkyl, $C_{5-8}$cycloalkyl, $C_{3-10}$cycloalkyl and the like. A $C_{3-10}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an 0, S or N atom, including, but not limited to, furanyl, thiophenyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothiophenyl, benzoimidazolyl, 1,3-benzothiazolyl, 1,3-benzoxazolyl, purinyl, quinolinyl, isoquinolinyl, quinazolinyl, quinoxalinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thiophenyl may also be referred to as thienyl, pyridinyl may also be referred to as pyridyl, benzothiophenyl may also be referred to as benzothienyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include I H-imidazolyl and the like, the term triazolyl may also include TH-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, tetrahydropyranyl, thiopyranyl, 1,3-dioxanyl, 1,3-oxazinanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl and the like. A heterocyclyl radical is optionally substituted on a carbon or nitrogen atom ring member with substituent species as described herein where allowed by available valences.

As used herein, the term "cyano" refers to a radical of the formula: —CN.

As used herein, the term "amino" refers to a radical of the formula: —$NH_2$.

As used herein, the term "$C_{1-6}$alkyl-amino" refers to a radical of the formula: —NH—$C_{1-6}$alkyl.

As used herein, the term "halo-$C_{1-6}$alkyl-amino" refers to a radical of the formula: —NH—$C_{1-6}$alkyl, wherein $C_{1-6}$alkyl is partially or completely substituted with one or more halogen atoms where allowed by available valences.

As used herein, the term "deutero-Cp-alkyl-amino" refers to a radical of the formula: —NH—$C_{1-6}$alkyl, wherein $C_{1-6}$alkyl is partially or completely substituted with one or more deuterium atoms where allowed by available valences.

As used herein, the term "($C_{1-6}$alkyl)$_2$-amino" refers to a radical of the formula: —N($C_{1-6}$alkyl)$_2$.

As used herein, the term "phenyl-amino" refers to a radical of the formula: —NH-phenyl.

As used herein, the term "heterocyclyl-amino" refers to a radical of the formula: —NH-heterocyclyl.

As used herein, the term "heteroaryl-amino" refers to a radical of the formula: —NH-heteroaryl.

As used herein, the term "$C_{1-6}$alkyl-thio" refers to a radical of the formula: —S—$C_{1-6}$alkyl.

As used herein, the term "$C_{1-6}$alkyl-sulfonyl" refers to a radical of the formula: —$SO_2$—$C_{1-6}$alkyl.

As used herein, the term "halo" or "halogen" generally refers to a halogen atom radical, including fluoro, chloro, bromo and iodo.

As used herein, the term "halo-$C_{1-6}$alkoxy" refers to a radical of the formula: —O—$C_{1-6}$alkyl-halo, wherein $C_{1-6}$alkyl is partially or completely substituted with one or more halogen atoms where allowed by available valences.

As used herein, the term "halo-$C_{1-6}$alkyl" refers to a radical of the formula: —$C_{1-6}$alkyl-halo, wherein $C_{1-6}$alkyl is partially or completely substituted with one or more halogen atoms where allowed by available valences.

As used herein, the term "deutero-$C_{1-6}$alkyl" refers to a radical of the formula: —$C_{1-6}$alkyl-deutero, wherein $C_{1-6}$alkyl is partially or completely substituted with one or more deuterium atoms where allowed by available valences.

As used herein, the term "hydroxy" refers to a radical of the formula: —OH.

As used herein, the term "hydroxy-$C_{1-6}$alkyl" refers to a radical of the formula: —$C_{1-6}$alkyl-OH, wherein $C_{1-6}$alkyl is partially or completely substituted with one or more hydroxy radicals where allowed by available valences.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances, one or more substituents having a double bond (e.g., "oxo" or "═O") as the point of attachment may be described, shown or listed herein within a substituent group, wherein the structure may only show a single bond as the point of attachment to the core structure of Formula (I). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or a form thereof encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as ". . . $C_{3-10}$cycloalkyl, $C_{3-10}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-10}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) having a form selected from the group consisting of a free acid, free base, prodrug, salt, hydrate, solvate, clathrate, isotopologue, racemate, enantiomer, diastereomer, stereoisomer, polymorph and tautomer form thereof.

In certain aspects described herein, the form of the compound of Formula (I) is a free acid, free base or salt thereof.

In certain aspects described herein, the form of the compound of Formula (I) is a salt thereof.

In certain aspects described herein, the form of the compound of Formula (I) is an isotopologue thereof.

In certain aspects described herein, the form of the compound of Formula (I) is a stereoisomer, racemate, enantiomer or diastereomer thereof.

In certain aspects described herein, the form of the compound of Formula (I) is a tautomer thereof.

In certain aspects described herein, the form of the compound of Formula (I) is a pharmaceutically acceptable form.

In certain aspects described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) can form salts, which are intended to be included within the scope of this description. Reference to a compound of Formula (I) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride or dichloride.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (1) and forms thereof may further exist in a tautomeric form. All such tautomeric forms are contemplated and intended to be included within the scope of the compounds of Formula (I) or a form thereof as described herein.

The compounds of Formula (1) or a form thereof may contain asymmetric or chiral centers, and, therefore, exist in different stereoisomeric forms. The present description is intended to include all stereoisomeric forms of the compounds of Formula (l) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "chiral" refers to a carbon atom bonded to four nonidentical substituents. Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511).

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

Compound Uses

Provided herein are methods of treating a disease in a subject in need thereof. As used herein, the terms "subject" or "patient" refer to any animal, including mammals. For example, mice, rats, other rodents, rabbits, dogs, cats, swine, cattle, sheep, horses, primates, and humans. In some aspects, the subject is a human.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some aspects, the dosage of the compound, or a pharmaceutically acceptable salt thereof, administered to a subject or individual is about I mug to about 2 g, about 1 mg to about 1000 mg, about I mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

The present application provides a method of treating SCA3 in a subject in need thereof, comprising administering to the subject a therapeutically effective amount of a compound provided herein (i.e., a compound of Formula (I)).

Also provided herein is a method of treating a subject having a disease caused by abnormal repeat expansions in the ATXN3 gene which results in mutant ATXN3 protein possessing a polyQ expansion, comprising administering to the subject a therapeutically effective amount of a compound provided herein (i.e., a compound of Formula (I)).

Also provided herein are methods of lowering ATXN3 mutant protein in a subject, comprising administering to the subject a therapeutically effective amount of a compound provided herein (i.e., a compound of Formula (I)).

In some aspects of the methods provided herein, the compound is selected from the group of compounds of Formula (I) or a pharmaceutically acceptable salt thereof.

Also provided herein are methods of inducing exon skipping in mutant ATXN3 pre-mRNA in a subject, comprising administering to a subject an effective amount of a compound of Formula (I) or form thereof.

Also provided herein are methods of inducing exon skipping in mutant ATXN3 pre-mRNA in a cell, comprising contacting a cell (e.g. ex vivo or in vivo) with a compound of Formula (I) or form thereof.

Also provided herein are methods of inducing exon skipping in mutant ATXN3 pre-mRNA in a gene comprising contacting the gene (e.g., in a cell or subject expressing the gene) with a compound a compound of Formula (I) or a form thereof.

Also provided therein are methods of inducing exon 4 skipping in the mutant ATXN3 pre-mRNA in a subject in need thereof, the method comprising administering an effective amount of a compound Formula (I) or a form thereof to the subject.

Also provided therein are methods of inducing exon 4 skipping in the mutant ATXN3 pre-mRNA in a cell, the method comprising contacting the cell (e.g. ex vivo or in vivo) with a compound Formula (I) or a form thereof to the subject.

Also provided herein are methods of inducing exon 4 skipping in the mutant ATXN3 pre-mRNA in a gene comprising contacting the gene (e.g., in a cell or subject expressing the gene) with a compound a compound of Formula (1) or a form thereof.

Also provided therein are methods of producing ATXN3 ΔE4 in a subject in need thereof, the method comprising administering an effective amount of a compound Formula (I) or a form thereof to the subject.

Also provided therein are methods of producing ATXN3 ΔE4 in a cell, the method comprising contacting the cell (e.g. ex vivo or in vivo) with a compound Formula (I) or a form thereof to the subject.

Also provided herein are methods of producing ATXN3 ΔE4 in a gene comprising contacting the gene (e.g., in a cell or subject expressing the gene) with a compound a compound of Formula (I) or a form thereof.

Also provided herein are methods for decreasing mutant ATXN3 mRNA in a subject in need thereof, the method comprising administering an effective amount of a compound of Formula (I) or a form thereof to the subject. For example, such methods include decreasing mutant ATXN3 mRNA concentration in serum samples from the subject.

In some aspects, mutant ATXN3 mRNA can be measured in the serum, for example, in blood samples obtained from the subject prior to administration of a compound of Formula (I) or form thereof and in blood samples obtained from the subject following administration of a compound as provided herein. In some aspects, the blood samples obtained from the subject following administration are obtained after one day, two days, three days, four days, five days, six days, seven days, eight days, nine days, ten days, fourteen days, twenty-one days, twenty-eight days, and/or thirty days of administration of the compound as provided herein. See, for example, F. B. Axelrod et al., Pediatr Res (2011) 70(5): 480-483; and R. S. Shetty et al., Human Molecular Genetics (2011) 20(21): 4093-4101, both of which are incorporated by reference in their entirety.

Further provided herein is a method for decreasing mutant ATXN3 mRNA in a cell, the method comprising contacting the cell (e.g. ex vivo or in vivo) with a therapeutically effective amount of a compound of Formula (I) or a form salt thereof. The amount of mutant ATXN3 mRNA in the treated cell is decreased relative to a cell in a subject in the absence of a compound provided herein. The method for decreasing the amount of mutant ATXN3 mRNA in a cell may be performed by contacting the cell with a compound of Formula (I) or a form thereof in vitro, thereby decreasing the amount of mutant ATXN3 mRNA of a cell in vitro. Uses of such an in vitro method of decreasing the amount of mutant ATXN3 mRNA include, but are not limited to, use in a screening assay (for example, wherein a compound of Formula (I) or a form thereof is used as a positive control or standard compared to a compound or compounds of unknown activity or potency in decreasing the amount mutant ATXN3 mRNA).

In some aspects, the amount of mutant ATXN3 mRNA is decreased in a cell selected from the group consisting of a lung cell, a muscle cell, a liver cell, a heart cell, a brain cell, a kidney cell, a spleen cell, and a nerve cell (e.g., a sciatic nerve cell or a trigeminal nerve cell), or any combination thereof. In some aspects thereof, the amount of mutant ATXN3 mRNA is decreased in the plasma.

The method of decreasing mutant ATXN3 mRNA in a cell may be performed, for example, by contacting a cell, (e.g., a lung cell, a muscle cell, a liver cell, a heart cell, a brain cell, a kidney cell, a spleen cell, or a nerve cell), with a compound of Formula (I) or a form thereof in vivo, thereby decreasing the amount of mutant ATXN3 mRNA in a subject in vivo. The contacting is achieved by causing a compound of Formula (I) or a form thereof to be present in a subject in an amount effective to achieve a decrease in the amount of mutant ATXN3 mRNA. This may be achieved, for example, by administering an effective amount of a compound of Formula (I) or a form thereof to a subject. Uses of such an in vivo method of decreasing the amount of mutant ATXN3 mRNA include, but are not limited to, use in methods of treating a disease or condition, wherein a decrease in the amount of mutant ATXN3 mRNA is beneficial.

In some aspects thereof, the amount of mutant ATXN3 mRNA is decreased in a cell selected from the group consisting of a lung cell, a muscle cell, a liver cell, a heart cell, a brain cell, a kidney cell, a spleen cell, and a nerve cell (e.g., a sciatic nerve cell or a trigeminal nerve cell), or any combination thereof, for example in a subject suffering from SCA3. The method is preferably performed by administering an effective amount of a compound of Formula (I) or a form thereof to a subject who is suffering from SCA3.

Also provided herein are methods for decreasing ATXN3 mutant protein expression in a subject in need thereof, the method comprising administering an effective amount of a compound of Formula (I) or a pharmaceutically acceptable salt thereof to the subject. For example, such methods include decreasing ATXN3 mutant protein expression in serum samples from the subject. Further provided herein are methods for decreasing the mean percentage of ATXN3 mutant protein expression in a subject in need thereof, the method comprising administering an effective amount of a compound of Formula (I) or a form thereof to the subject.

Also provided herein are methods for decreasing ATXN3 mutant protein expression in a cell (e.g., ex vivo or in vivo), the method comprising contacting the cell with a therapeutically effective amount of a compound of Formula (I) or a form thereof. In some aspects the method is an in vitro method. In some aspects, the method is an in vivo method. In some aspects, the amount ATXN3 mutant protein expression is decreased in a cell selected from the group consisting of a lung cell, a muscle cell, a liver cell, a heart cell, a brain cell, a kidney cell, a spleen cell, and a nerve cell (e.g., a sciatic nerve cell or a trigeminal nerve cell), or any combination thereof. In some aspects thereof, the amount of ATXN3 mutant protein expression is decreased in the plasma.

Also provided herein are methods for decreasing ATXN3 mutant protein level in a subject in need thereof, the method comprising administering an effective amount of a compound of Formula (I) or a form thereof to the subject. For example, such methods include decreasing ATXN3 mutant protein level in serum samples from the subject. Further provided herein are methods for decreasing the mean percentage of ATXN3 mutant protein level in a subject in need thereof, the method comprising administering an effective amount of a compound of Formula (I) or a form thereof, to the subject.

Also provided herein are methods for decreasing ATXN3 mutant protein level in a cell (e.g., ex vivo or in vivo), the method comprising contacting the cell with a therapeutically effective amount of a compound of Formula (I) or a form thereof.

In some aspects, the method is an in vitro method. In some aspects, the method is an in vivo method. In some aspects, the amount of ATXN3 mutant protein level is decreased in a cell selected from the group consisting of a lung cell, a muscle cell, a liver cell, a heart cell, a brain cell, a kidney cell, a spleen cell, and a nerve cell (e.g., a sciatic nerve cell or a trigeminal nerve cell), or any combination thereof. In some aspects thereof, the amount of ATXN3 mutant protein level is decreased in plasma.

In some aspects, one or more of the compounds of Formula (I) or form thereof may be administered to a subject in need thereof in combination with at least one additional pharmaceutical agent.

Additional examples of suitable additional pharmaceutical agents for use in combination with the compounds of the present application for treatment of the diseases provided herein include, but are not limited to, antioxidants, anti-inflammatory agents, steroids, immunosuppressants, or other agents such as therapeutic antibodies. In some aspects, the compounds of Formula (I) or a form thereof may be administered to a subject in need thereof in combination with at least one additional pharmaceutical agent for the treatment of SCA3.

When employed as a therapeutic agent, the compounds provided herein can be administered in the form of a pharmaceutical composition; thus, the methods described herein can include administering a pharmaceutical composition. These compositions can be prepared as described herein or elsewhere, and can be administered by a variety of routes, depending upon whether local or systemic treatment is desired and upon the area to be treated. Administration may be pulmonary (e.g., by inhalation or insufflation of powders or aerosols, including by nebulizer; intratracheal or intranasal), oral, or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable. In some aspects, the compounds provided herein are suitable for oral and parenteral administration. In some aspects, the compounds provided herein are suitable for oral administration. In some aspects, the compounds provided herein are suitable for parenteral administration. In some aspects, the compounds provided herein are suitable for intravenous administration. In some aspects, the compounds provided herein are suitable for transdermal administration (e.g., administration using a patch or microneedle). Pharmaceutical compositions for topical administration may include transdermal patches (e.g., normal or electrostimulated), ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound of Formula (I) or a form thereof in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood that the amount of compound to be administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

In another aspect, the concentration-biological effect relationship observed with regard to a compound of Formula (I) or a form thereof indicate a target plasma concentration ranging from approximately 0.001 μg·hr/mL to approximately 50 μg·hr/mL, from approximately 0.01 μg·hr/mL to approximately 20 μg·hr/mL, from approximately 0.05 μg·hr/mL to approximately 10 μg·hr/mL, or from approximately 0.1 μg·hr/mL to approximately 5 μg·hr/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 tug/kg/day to about 1000 tug/kg/day, or about 0.001 mg/kg/day to about 500 mg/kg/day, or about 0.001 mg/kg/day to about 250 mg/kg/day, or about 0.001 tug/kg/day to about 200 mg/kg/day, or about 0.001 tug/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 tug/kg/day to about 2500 mg/kg/day, or about 0.01 mg/kg/day to about 2000 mg/kg/day, or about 0.01 mg/kg/day to about 1500 mg/kg/day, or about 0.01 tug/kg/day to about 1000 mg/kg/day, or about 0.01 mg/kg/day to about 500 tug/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12 h"), thrice (once in approximately an 8 hour period; i.e., "t.i.d." or "q.8 h"), or four times (once in approximately a 6 hour period; i.e., "q.d.s.", "qi.d." or "q.6 h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intraveneous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled (e.g., $^{14}C$ or $^{3}H$) compound of Formula (I), administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Preparation of Compounds

Compounds of Formula (I) can be prepared using reagents and methods known in the art, including the methods provided in International Application No. PCT/US2020/063612, the entire contents of which are incorporated herein by reference.

BIOLOGICAL EXAMPLES

The following in vitro biological examples demonstrate the usefulness of the compounds of the present description for treating SCA3.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

EXAMPLE 1

Endogenous Total ATXN3 (tATXN3) Protein Assay

Meso Scale Discovery (MSD) 96-well or 384-well plates were coated overnight at 4° C. with Ataxin 3 mouse monoclonal antibody (Invitrogen, MA3-082) at a concentration of 0.5 μg/mL in PBS (30 μL per well). Plates were then washed three times with 300 μL wash buffer (0.05% TWEEN®-20, polyethylene glycol sorbitan monolaurate, in PBS) and blocked (Meso Scale Diagnostics, R93BA-1; 5% BSA in PBS) for 2 h at room temperature with rotational shaking and then washed three times with wash buffer.

Test compounds were serially diluted 3.16-fold in 100% DMSO to generate a 7-point concentration curve. Aliquots of 0.5 μL of diluted compounds were transferred to a 96-well flat bottom plate by a liquid handler. An aliquot of 0.5 μL DMSO was also transferred to separate wells and used as controls. Duplicate samples were set up for each compound concentration and for the DMSO control.

Cells were thawed and incubated in cell culture media (DMEM, 10% FBS, and 1% antibiotic cocktail) for 72 h. Cells were trypsinized, counted, and re-suspended to a concentration of 100,000 cells/mL in cell culture media. A 100 μL aliquot of the cell suspensions were plated at 10,000 cells per well in the compound containing 96 well microtiter plate and incubated for in a cell culture incubator (37° C., 5% $CO_2$, 100% relative humidity). After 48 h, the medium was removed and 50-100 μL of lysis buffer (Meso Scale Diagnostics, R60TX-2) containing IX halt protease inhibitor cocktail of (Thermo Scientific, Halt™ Protease Inhibitor Cocktail, 78430) per well was added to cells to provide a "cell lysate". The plate was placed on a shaker at 4° C. for 30 minutes, then stored at −80° C.

Cell lysate samples (25 μL) were transferred to the antibody-coated MSD plate and incubated overnight at 4° C. After removal of the lysates, the plate was washed three times with wash buffer, and 25 μL of Ataxin 3 recombinant rabbit monoclonal antibody (Invitrogen, #702788) secondary antibody (diluted to 0.25 μg/mL in 0.05% TWEEN®-20 in blocking buffer) was added to each well and incubated with shaking for 1-2 h at room temperature. Following incubation with the secondary antibody, the wells were rinsed with wash buffer and then 25 μL of Anti Rabbit Antibody Goat SULFO-TAG Labeled (Meso Scale Diagnostics, R32AB-1) detecting antibody (diluted to 0.25 μg/mL in 0.05% TWEEN®-20 in blocking buffer) was added to each well and incubated with shaking for 1 h at room temperature. After rinsing three times with wash buffer, 150 μL of Read Buffer T with surfactant (tris-based buffer containing tripropylamine, Meso Scale Diagnostics, R92TC-1) were added to each empty well, and the plate was imaged on a SI 6000 imager (MSD) according to manufacturers' instructions provided for 96- or 384-well plates. The resulting average $IC_{50}$ values (μM) for the representative compounds tested are shown in Table 1.

An average $IC_{50}$>2 μM is indicated by one star (*), between >1.5 μM and ≤2 μM is indicated by two stars (), between >1.0 μM and ≤1.5 μM is indicated by three stars (*), between >0.5 μM and ≤1.0 μM is indicated by four stars (**), and ≤0.5 μM is indicated by five stars (***).

TABLE 1

| Cpd | $IC_{50}$ |
|---|---|
| 5 | ***** |
| 7 | inactive |
| 12 | ***** |
| 15 | **** |
| 23 | inactive |
| 24 | * |
| 27 | inactive |
| 28 | ***** |
| 29 | ***** |
| 30 | ** |
| 31 | * |
| 33 | ***** |
| 35 | ***** |
| 38 | ***** |
| 39 | ***** |
| 40 | ***** |
| 47 | inactive |
| 51 | ***** |
| 52 | * |
| 55 | * |

TABLE 1-continued

| Cpd | $IC_{50}$ |
|---|---|
| 56 | ***** |
| 57 | inactive |
| 59 | ** |
| 60 | * |
| 62 | ***** |
| 64 | *** |
| 66 | inactive |
| 67 | inactive |
| 68 | ***** |
| 70 | *** |
| 72 | * |
| 73 | inactive |
| 74 | ** |
| 75 | *** |
| 77 | ***** |
| 78 | ** |
| 80 | inactive |
| 81 | inactive |
| 82 | ***** |
| 86 | ***** |
| 88 | inactive |
| 90 | ***** |
| 92 | ***** |
| 93 | ***** |
| 94 | inactive |
| 97 | ***** |

EXAMPLE 2

RT-qPCR Assay to Quantify Exon 4 Skipping in ATXN3 pre-mRNA in Cells

Test compounds were serially diluted 3.16-fold in 100% DMSO to generate a 7-point concentration curve. Aliquots of 0.5 μL of diluted compounds were transferred to a 96-well flat bottom plate by a liquid handler. An aliquot of 0.5 μL DMSO was also transferred to separate wells and used as controls. Duplicate samples were set up for each compound concentration and for the DMSO control.

Cells were thawed and incubated in cell culture media (DMEM, 10% FBS, and 1% antibiotic cocktail) for 72 h. Cells were trypsinized, counted, and re-suspended to a concentration of 100,000 cells/mL in cell culture media. A 100 μL aliquot of the cell suspensions were plated at 10,000 cells per well in the compound containing 96 well microtiter plate and incubated for in a cell culture incubator (37° C., 5% $CO_2$, 100% relative humidity).

After 24 h, media was aspirated from the cells and 50 L of the RCL2 lysis buffer (10 mM Tris-HCL pH 7.4, 150 mM NaCl, 0.33% IGEPAL® CA-630) was added to each well and incubated at room temperature for 1 min. Chilled nuclease free water (50 μL per well) was added and the plates were immediately transferred on ice. After 1 min on ice, plates were frozen at −80° C. overnight.

Preparation of R.T-qPCR Reaction Mixture:

| Reagent | Volume (μL) | Supplier and Catalogue No. |
|---|---|---|
| RT-PCR buffer (2X) | 5.0 | Thermo Fisher, 4387391 |
| RT-PCR enzyme mixture (25X) | 0.4 | Thermo Fisher, 4387391 |
| Target Primer/Probe (60X) | 0.16 | Thermo Fisher, 4331182 |
| In house GAPDH assay (20X) | 0.5 | |
| $H_2O$ | 1.94 | |

Abbreviations:
GAPDH, glyceraldehyde 3-phosphate dehydrogenase
Target: TaqMan assay ID Hs00245261_ml
In house GAPDH assay:
Forward primer - 5' caacggatttggtcgtattgg 3'
Reverse primer - 5' tgatggcaacaatatccactttacc 3'
Probe (VIC-TAMRA) - 5' cgcctggtcaccagggctgct 3'

An aliquot of 2 μL/well of the cell lysates was transferred using the liquid handler to the Armadillo 384-Well PCR plate containing 8 μL/well of the RT-qPCR reaction mixture that was prepared as detailed above. The plates were then sealed with MicroAmp™ Optical Adhesive Film followed by spinning down for 1 min and placed in the CFX384 thermocycler (BioRad).

The RT-qPCR was carried out at the following temperatures for the indicated time:

Step 1: 48° C. (30 min)
Step 2: 95° C. (10 min)
Step 3: 95° C. (15 sec)
Step 4: 60° C. (1 min);

then, repeated Steps 3 and 4 for a total of 40 cycles.

The percent exon 4 skipping was calculated for each dose of compound treatment using Equations 1 and 2.

$$\text{Realtive gene expression} = \frac{2^{-Ct(target)}}{1.9^{-Ct(GAPDH)}} \quad \text{Equation 1}$$

$$\text{Percent exon 4 skipping (\%)} = 1 - \left[\frac{\text{Realtive gene expression, Compound}}{\text{Realtive gene expression, } DMSO}\right] \times 100 \quad \text{Equation 2}$$

Data were fit to a dose response curve and the $IC_{50}$ was interpolated using XLfit® statistical and curve fitting package. The resulting $IC_{50}$ values (μM) for the representative compounds tested are shown in Table 2.

An $IC_{50}$ value between >2.0 μM and ≤3.0 μM is indicated by one star (*). An $IC_{50}$ value between 1.5 μM and <2.0 μM is indicated by two stars (). An $IC_{50}$ value between >1.0 μM and ≤1.5 μM is indicated by three stars (*). $IC_{50}$ value between >0.5 μM and≤1.0 μM is indicated by four stars (**). An $IC_{50}$ value ≤0.5 μM is indicated by five stars (***).

TABLE 2

| Cpd | $IC_{50}$ |
|---|---|
| 5 | **** |
| 7 | inactive |
| 12 | ***** |
| 15 | ***** |
| 23 | inactive |
| 24 | ** |
| 27 | * |
| 28 | ***** |
| 29 | ***** |

TABLE 2-continued

| Cpd | $IC_{50}$ |
|---|---|
| 30 | *** |
| 31 | * |
| 33 | ***** |
| 35 | ***** |
| 38 | ***** |
| 39 | ***** |
| 40 | ***** |
| 47 | inactive |
| 51 | ***** |
| 52 | inactive |
| 55 | * |
| 56 | ***** |
| 57 | inactive |
| 59 | *** |
| 60 | * |
| 62 | ***** |
| 64 | **** |
| 66 | inactive |
| 67 | inactive |
| 68 | ***** |
| 70 | **** |
| 72 | ** |
| 73 | inactive |
| 74 | *** |
| 75 | **** |
| 77 | ***** |
| 78 | *** |

TABLE 2-continued

| Cpd | $IC_{50}$ |
|---|---|
| 80 | inactive |
| 81 | inactive |
| 82 | ***** |
| 86 | ***** |
| 88 | inactive |
| 90 | ***** |
| 92 | ***** |
| 93 | ***** |
| 94 | inactive |
| 97 | ***** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A method for inhibiting or ameliorating spinocerebellar ataxia type 3 (SCA3) in a subject in need thereof, comprising administering to said subject an effective amount of a compound of Formula (I):

(I)

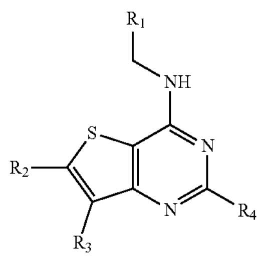

or a form thereof, wherein $R_1$ is selected from the group consisting of tetrazolyl, phenyl and heteroaryl, wherein the heteroaryl is a bicyclic aromatic carbon atom ring structure or a 5-8 membered monocyclic aromatic carbon atom ring structure containing 1-3 heteroatoms selected from N, O, and S, and wherein phenyl or heteroaryl is optionally substituted with one, two, three, or four, independently selected $R_{1a}$ substituents;

$R_{1a}$ is independently selected from the group consisting of cyano, halo, hydroxy, $C_{1-6}$alkyl, halo-$C_{1-6}$alkyl, deutero-$C_{1-6}$alkyl, and $C_{1-6}$alkoxy;

$R_2$ is selected from the group consisting of hydrogen, $C_{1-6}$alkyl, $C_{2-6}$alkenyl, $C_{2-6}$alkynyl, $C_{3-10}$cycloalkyl, phenyl, heterocyclyl, and heteroaryl, wherein heterocyclyl is a 3-7 membered monocyclic carbon atom ring structure containing 1-3 heteroatoms selected from N, O, and S, wherein the heteroaryl is a bicyclic aromatic carbon atom ring structure or a 5-8 membered monocyclic aromatic carbon atom ring structure containing 1-3 heteroatoms selected from N, O, and S, wherein $C_{1-6}$alkyl, $C_{2-6}$alkenyl, and $C_{2-6}$alkynyl optionally contain a chiral carbon having an (R) or (S) configuration, and wherein $C_{1-6}$alkyl, $C_{2-6}$alkenyl, $C_{2-6}$alkynyl, $C_{3-10}$cycloalkyl, phenyl, heterocyclyl, or heteroaryl are optionally substituted with one, two, three, or four independently selected $R_{2a}$ substituents;

$R_{2a}$ is independently selected from the group consisting of cyano, halo, hydroxy, oxo, $C_{1-6}$alkyl, halo-$C_{1-6}$alkyl, deutero-$C_{1-6}$alkyl, $C_{2-6}$alkenyl, $C_{2-6}$alkynyl, $C_{1-6}$alkoxy, halo-$C_{1-6}$alkoxy, carboxyl, amino, $C_{1-6}$alkyl-amino, halo-$C_{1-6}$alkyl-amino, deutero-$C_{1-6}$alkyl-amino, $(C_{1-6}alkyl)_2$-amino, $C_{3-10}$cycloalkyl-amino, phenyl-amino, heterocyclyl-amino, heteroaryl-amino, $C_{1-6}$alkyl-thio, $C_{1-6}$alkyl-sulfonyl, $C_{3-10}$cycloalkyl, phenyl, heterocyclyl, and heteroaryl, wherein heterocyclyl is a 3-7 membered monocyclic carbon atom ring structure containing 1-3 heteroatoms selected from N, O, and S, wherein the heteroaryl is a bicyclic aromatic carbon atom ring structure or a 5-8 membered monocyclic aromatic carbon atom ring structure containing 1-3 heteroatoms selected from N, O, and S, and wherein each instance of $C_{3-10}$cycloalkyl, phenyl, heterocyclyl or heteroaryl is optionally substituted with one, two, three or four independently selected $R_{2a'}$ substituents;

$R_{2a'}$ is independently selected from the group consisting of cyano, halo, hydroxy, oxo, $C_{1-6}$alkyl, halo-$C_{1-6}$alkyl, deutero-$C_{1-6}$alkyl, and $C_{1-6}$alkoxy;

$R_3$ is selected from the group consisting of hydrogen, cyano, halo, hydroxy, $C_{1-6}$alkyl, halo-$C_{1-6}$alkyl, $C_{1-6}$alkoxy, amino, $C_{1-6}$alkyl-amino, $(C_{1-6}alkyl)_2$-amino, $C_{3-10}$cycloalkyl, phenyl, heterocyclyl, and heteroaryl, wherein heterocyclyl is a 3-7 membered monocyclic carbon atom ring structure containing 1-3 heteroatoms selected from N, O, and S, and wherein the heteroaryl is a bicyclic aromatic carbon atom ring structure or a 5-8 membered monocyclic aromatic carbon atom ring structure containing 1-3 heteroatoms selected from N, O, and S, and wherein $C_{1-6}$alkyl, $C_{3-10}$cycloalkyl, phenyl, heterocyclyl, or heteroaryl is optionally substituted with one, two, three, or four independently selected $R_{3a}$ substituents;

$R_{3a}$ is independently selected from the group consisting of cyano, halo, hydroxy, $C_{1-6}$alkyl, halo-$C_{1-6}$alkyl, and $C_{1-6}$alkoxy;

$R_4$ is selected from the group consisting of hydrogen, cyano, halo, hydroxy, $C_{1-6}$alkyl, halo-$C_{1-6}$alkyl, $C_{1-6}$alkoxy, carbamoyl, $C_{3-10}$cycloalkyl, phenyl, and heterocyclyl, and wherein heterocyclyl is a 3-7 membered monocyclic carbon atom ring structure containing 1-3 heteroatoms selected from N, O, and S; and wherein the form of the compound is selected from the group consisting of a salt, hydrate, solvate, and tautomer form thereof.

2. The method of claim 1, wherein $R_1$ is phenyl optionally substituted with one, two, three, or four independently selected $R_{1a}$ substituents.

3. The method of claim 1, wherein $R_1$ is heteroaryl selected from the group consisting of furanyl, thiophenyl, 1H-pyrazolyl, 1H-imidazolyl, isoxazolyl, 1,2-thiazolyl, 1,3-thiazolyl, 1,2-oxazolyl, 1,3-oxazolyl, tetrazolyl, 1,2,3-triazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, wherein heteoraryl is optionally substituted with one, two, three, or four independently selected $R_{1a}$ substituents.

4. The method of claim 1, wherein $R_1$ is heteroaryl selected from the group consisting of furanyl, thiophenyl, 1H-pyrazolyl, 1H-imidazolyl, 1,2-thiazolyl, 1,3-thiazolyl, 1,2-oxazolyl, 1,3-oxazolyl, pyridinyl, pyrimidinyl, and pyrazinyl.

5. The method of claim 1, wherein $R_{1a}$ is selected from the group consisting of halo and $C_{1-6}$alkyl.

6. The method of claim 1, wherein $R_2$ is selected from the group consisting of hydrogen, $C_{1-6}$alkyl, and heterocyclyl.

7. The method of claim 1, wherein $R_2$ is $C_{1-6}$alkyl selected from the group consisting of methyl, ethyl, propyl, butyl, and pentyl.

8. The method of claim 1, wherein $R_2$ is $C_{1-6}$alkyl, and wherein $C_{1-6}$alkyl contains a chiral carbon having the (R) configuration.

9. The method of claim 1, wherein $R_2$ is $C_{1-6}$alkyl, and wherein $C_{1-6}$alkyl contains a chiral carbon having the (S) configuration.

10. A method for inhibiting or ameliorating spinocerebellar ataxia type 3 (SCA3) in a subject in need thereof, comprising administering to said subject an effective amount of a compound or a form thereof wherein the compound is selected from the group consisting of;

2-chloro-N-[(pyridin-4-yl)methyl]thieno[3,2-d]pyrimidin-4-amine;

2-chloro-N-[(furan-2-yl)methyl]thieno[3,2-d]pyrimidin-4-amine;

6-[(2S)-2-aminopropyl]-2-chloro-N-[(furan-2-yl)methyl]thieno[3,2-d]pyrimidin-4-amine;

6-[(2S)-2-aminobutyl]-2-chloro-N-[(furan-2-yl)methyl]thieno[3,2-d]pyrimidin-4-amine;

6-[(2R)-2-amino-3-methylbutyl]-2-chloro-N-[(furan-2-yl)methyl]thieno[3,2-d]pyrimidin-4-amine;

6-[(2R,3S)-2-amino-3-methylpentyl]-2-chloro-N-[(furan-2-yl)methyl]thieno[3,2-d]pyrimidin-4-amine;

6-[(2R)-2-amino-3,3-dimethylbutyl]-2-chloro-N-[(furan-2-yl)methyl]thieno[3,2-d]pyrimidin-4-amine;

6-[(2S)-2-aminopropyl]-N-[(furan-2-yl)methyl]thieno[3,2-d]pyrimidin-4-amine;

6-[(2S)-2-aminopropyl]-2-chloro-N-[(pyridin-4-yl)methyl]thieno[3,2-d]pyrimidin-4-amine;

6-[(2S)-2-aminobutyl]-2-chloro-N-[(thiophen-2-yl)methyl]thieno[3,2-d]pyrimidin-4-amine;

6-[(2S)-2-aminopropyl]-N-[(pyridin-4-yl)methyl]thieno[3,2-d]pyrimidin-4-amine;

6-[(2S)-2-aminopropyl]-2-chloro-N-[(furan-2-yl)methyl]-7-methylthieno[3,2-d]pyrimidin-4-amine;

6-[(2S)-2-aminobutyl]-2-chloro-N-[(furan-2-yl)methyl]-7-methylthieno[3,2-d]pyrimidin-4-amine;

6-[(2S)-2-aminopropyl]-2-chloro-N-[(thiophen-2-yl)methyl]thieno[3,2-d]pyrimidin-4-amine;

6-[(2S)-2-aminopropyl]-N-[(furan-2-yl)methyl]-2,7-dimethylthieno[3,2-d]pyrimidin-4-amine;

6-[(2S)-2-aminopropyl]-2-ethyl-N-[(furan-2-yll)methyl]-7-methylthieno[3,2-d]pyrimidin-4-amine;

6-[(2S)-2-aminopropyl]-2-cyclopropyl-N-[(furan-2-yl)methyl]-7-methylthieno[3,2-d]pyrimidin-4-amine;

2-chloro-N-[(furan-2-yl)methyl]-7-methylthieno[3,2-d]pyrimidin-4-amine;

(2R)-2-amino-3-(2-chloro-4-{[(furan-2-yl)methyl]amino}-7-methylthieno[3,2-d]pyrimidin-6-yl)propan-1-ol;

6-[(2S)-2-aminopropyl]-4-{[(furan-2-yl)methyl]amino}-7-methylthieno[3,2-d]pyrimidine-2-carboxamide;

6-[(2S)-2-aminopropyl]-4-{[(furan-2-yl)methyl]amino}-7-methylthieno[3,2-d]pyrimidine-2-carbonitrile;

(2R)-2-amino-3-(2-chloro-4-{[(furan-2-yl)methyl]amino}thieno[3,2-d]pyrimidin-6-yl)propan-1-ol;

2-chloro-7-methyl-N-[(pyridin-4-yl)methyl]thieno[3,2-d]pyrimidin-4-amine;

6-[(2S)-2-aminopropyl]-2-chloro-7-methyl-N-[(5-methylfuran-2-yl)methyl]thieno[3,2-d]pyrimidin-4-amine;

N-[(furan-2-yl)methyl]-7-methyl-2-(trifluoromethyl)thieno[3,2-d]pyrimidin-4-amine;

6-[(2S)-2-aminopropyl]-N-[(furan-2-yl)methyl]-7-methyl-2-(trifluoromethyl)thieno[3,2-d]pyrimidin-4-amine;

6-[(2S)-2-aminopropyl]-2-chloro-7-methyl-N-[(4-methyl-1,3-thiazol-2-yl)methyl]thieno[3,2-d]pyrimidin-4-amine;

6-[(2S)-2-aminopropyl]-2-chloro-7-methyl-N-[(thiophen-2-yl)methyl]thieno[3,2-d]pyrimidin-4-amine;

6-[(2S)-2-aminopropyl]-2-chloro-7-methyl-N-[(1,3-thiazol-2-yl)methyl]thieno[3,2-d]pyrimidin-4-amine;

6-[(2S)-2-aminopropyl]-2-chloro-7-methyl-V-[(3-methylfuran-2-yl)methyl]thieno[3,2-d]pyrimidin-4-amine;

6-[(2S)-2-aminopropyl]-2-chloro-7-methyl-N-[(5-methyl-1,3-thiazol-2-yl)methyl]thieno[3,2-d]pyrimidin-4-amine;

6-[(2S)-2-aminopropyl]-2-chloro-7-methyl-N-[(pyrazin-2-yl)methyl]thieno[3,2-d]pyrimidin-4-amine;

6-[(2S)-2-aminopropyl]-2-chloro-N-[(5-fluorothiophen-2-yl)methyl]-7-methylthieno[3,2-d]pyrimidin-4-amine 6-[(2S)-2-aminopropyl]-N-benzyl-2-chloro-7-methylthieno[3,2-d]pyrimidin-4-amine;

6-[(2,S)-2-aminopropyl]-2-chloro-N-[(3-fluoropyridin-4-yl)methyl]-7-methylthieno[3,2-d]pyrimidin-4-amine;

6-[(2S)-2-aminopropyl]-2-chloro-7-cyclopropyl-N-[(furan-2-yl)methyl]thieno[3,2-d]pyrimidin-4-amine;

6-[(2S)-2-aminobutyl]-2-chloro-7-methyl-N-[(thiophen-2-yl)methyl]thieno[3,2-d]pyrimidin-4-amine;

6-[(2S)-2-aminopropyl]-2-bromo-N-[(furan-2-yl)methyl]-7-methylthieno[3,2-d]pyrimidin-4-amine;

6-[(2S)-2-aminopropyl]-2-chloro-7-methyl-N-[(1,2-oxazol-5-yl)methyl]thieno[3,2-d]pyrimidin-4-amine;

6-[(2S)-2-aminopropyl]-7-bromo-2-chloro-N-[(furan-2-yl)methyl]thieno[3,2-d]pyrimidin-4-amine;

6-(azetidin-3-yl)-2-chloro-N-[(furan-2-yl)methyl]-7-methylthieno[3,2-d]pyrimidin-4-amine;

7-bromo-2-chloro-N-[(furan-2-yl)methyl]thieno[3,2-d]pyrimidin-4-amine;

7-bromo-2-chloro-N-[(pyridin-4-yl)methyl]thieno[3,2-d]pyrimidin-4-amine;

6-[(2S)-2-aminopropyl]-2-chloro-N-[(2-fluorophenyl)methyl]-7-methylthieno[3,2-d]pyrimidin-4-amine;

6-[(2S)-2-aminopropyl]-2-chloro-7-methyl-N-[(pyridin-4-yl)methyl]thieno[3,2-d]pyrimidin-4-amine;

6-[(IS)-1-aminoethyl]-7-bromo-2-chloro-N-[(furan-2-yl)methyl]thieno[3,2-d]pyrimidin-4-amine;

6-[(1S)-1-aminoethyl]-2-chloro-N-[(furan-2-yl)methyl]-7-methylthieno[3,2-d]pyrimidin-4-amine;

6-[(1S)-1-aminopropyl]-2-chloro-N-[(furan-2-yl)methyl]-7-methylthieno[3,2-d]pyrimidin-4-amine;

6-[(1R)-1-aminopropyl]-2-chloro-N-[(furan-2-yl)methyl]-7-methylthieno[3,2-d]pyrimidin-4-amine;

6-[(2S)-2-aminopropyl]-2-chloro-7-methyl-N-[(pyrimidin-4-yl)methyl]thieno[3,2-d]pyrimidin-4-amine;

6-[(2S)-2-amino-4-fluorobutyl]-2-chloro-V-[(furan-2-yl)methyl]-7-methylthieno[3,2-d]pyrimidin-4-amine;

(4S)-4-[(2-chloro-4-{[(furan-2-yl)methyl]amino}-7-methylthieno[3,2-d]pyrimidin-6-yl)methyl]-1,3-oxazinan-2-one;

6-[(2S)-2-aminobutyl]-2-chloro-N-[(3-fluoropyridin-4-yl)methyl]-7-methylthieno[3,2-d]pyrimidin-4-amine;

6-[(2S)-2-aminobutyl]-2-chloro-7-methyl-N-[(1,3-thiazol-2-yl)methyl]thieno[3,2-d]pyrimidin-4-amine;

6-[(2S)-2-aminopropyl]-2-chloro-7-methyl-N-[(pyrimidin-2-yl)methyl]thieno[3,2-d]pyrimidin-4-amine;

(2R)-2-amino-3-(2-chloro-7-methyl-4-{[(thiophen-2-yl)methyl]amino}thieno[3,2-d]pyrimidin-6-yl)propan-1-ol;

2-chloro-N-[(furan-2-yl)methyl]-7-methyl-6-(pyrrolidin-3-yl)thieno[3,2-d]pyrimidin-4-amine;

6-[(1S)-1-aminoethyl]-2-chloro-N-[(furan-2-yl)methyl]-7-phenylthieno[3,2-d]pyrimidin-4-amine;

6-[(2S)-2-aminopropyl]-2-chloro-N-[(3-fluoropyridin-2-yl)methyl]-7-methylthieno[3,2-d]pyrimidin-4-amine;

6-[(2S)-2-aminopropyl]-2-chloro-N-[(2-fluoropyridin-3-yl)methyl]-7-methylthieno[3,2-d]pyrimidin-4-amine;

6-[(1S)-1-aminoethyl]-N-[(furan-2-yl)methyl]-2,7-diphenylthieno[3,2-d]pyrimidin-4-amine;

6-[(2S)-2-aminobutyl]-2-chloro-7-methyl-N-[(1,2-thiazol-5-yl)methyl]thieno[3,2-d]pyrimidin-4-amine;

3-(2-chloro-4-{[(furan-2-yl)methyl]amino}-7-methylthieno[3,2-d]pyrimidin-6-yl)propan-I-ol;

6-[(2S)-2-aminopropyl]-2-chloro-N-[(3,5-difluoropyridin-4-yl)methyl]-7-methylthieno[3,2-d]pyrimidin-4-amine;

6-[(2S)-2-aminopropyl]-2-chloro-N-[(furan-2-yl)methyl]-7-(4-methoxyphenyl)thieno[3,2-d]pyrimidin-4-amine;

(2S)-3-(2-chloro-4-{[(furan-2-yl)methyl]amino}-7-methylthieno[3,2-d]pyrimidin-6-yl)-2-methylpropan-1-ol;

6-(3-aminopropyl)-2-chloro-N-[(furan-2-yl)methyl]-7-methylthieno[3,2-d]pyrimidin-4-amine;

6-[(2S)-2-aminopropyl]-7-bromo-2-chloro-V-[(3-fluoropyridin-4-yl)methyl]thieno[3,2-d]pyrimidin-4-amine;

6-[(2S)-2-aminobutyl]-2-chloro-7-methyl-N-[(1,3-oxazol-2-yl)methyl]thieno[3,2-d]pyrimidin-4-amine;

6-[(2S)-3-amino-2-methylpropyl]-2-chloro-N-[(furan-2-yl)methyl]-7-methylthieno[3,2-d]pyrimidin-4-amine;

(2R)-3-(2-chloro-4-{[(furan-2-yl)methyl]amino}-7-methylthieno[3,2-d]pyrimidin-6-yl)-2-methylpropan-1-ol;

6-[(2R)-3-amino-2-methylpropyl]-2-chloro-N-[(furan-2-yl)methyl]-7-methylthieno[3,2-d]pyrimidin-4-amine;

6-[(2S)-2-aminopropyl]-2-chloro-N-[(1H-imidazol-2-yl)methyl]-7-methylthieno[3,2-d]pyrimidin-4-amine;

6-[(2S)-2-aminopropyl]-2-chloro-7-methyl-N-[(1,3-thiazol-5-yl)methyl]thieno[3,2-d]pyrimidin-4-amine;

6-[(2S)-2-aminopropyl]-2-chloro-7-methyl-N-[(1,3-oxazol-5-yl)methyl]thieno[3,2-d]pyrimidin-4-amine;

6-[(2R)-2-amino-3-methoxypropyl]-2-chloro-N-[(furan-2-yl)methyl]-7-methylthieno[3,2-d]pyrimidin-4-amine;

6-[(2S)-2-aminopropyl]-2-chloro-7-ethyl-N-[(furan-2-yl)methyl]thieno[3,2-d]pyrimidin-4-amine;

2-chloro-6-[(2S)-2-(cyclobutylamino)propyl]-N-[(furan-2-yl)methyl]-7-methylthieno[3,2-d]pyrimidin-4-amine;

2-chloro-N-[(furan-2-yl)methyl]-7-methyl-6-[(2S)-2-(methylamino)propyl]thieno[3,2-d]pyrimidin-4-amine;

7-bromo-2-chloro-N-[(thiophen-2-yl)methyl]thieno[3,2-d]pyrimidin-4-amine:

6-[(2S)-2-aminopropyl]-2-chloro-7-methyl-N-[(1-methyl-1H-pyrazol-5-yl)methyl]thieno[3,2-d]pyrimidin-4-amine;

6-[((2S)-2-aminopropyl]-7-bromo-2-chloro-N-[(thiophen-2-yl)methyl]thieno[3,2-d]pyrimidin-4-amine;

6-[(2S)-2-aminopropyl]-7-bromo-4-{[(thiophen-2-yl)methyl]amino}thieno[3,2-d]pyrimidine-2-carbonitrile;

2-chloro-4-{[(thiophen-2-yl)methyl]amino}thieno[3,2-d]pyrimidine-7-carbonitrile;

6-[(2S)-2-aminopropyl]-4-{[(thiophen-2-yl)methyl]amino}thieno[3,2-d]pyrimidine-2,7-dicarbonitrile;

6-[(2S)-2-aminopropyl]-2-chloro-7-cyclopropyl-V-[(thiophen-2-yl)methyl]thieno[3,2-d]pyrimidin-4-amine;

6-[(2S)-2-aminopropyl]-2-chloro-7-phenyl-N-[(thiophen-2-yl)methyl]thieno[3,2-d]pyrimidin-4-amine;

6-[(2S)-2-aminopropyl]-2-chloro-7-(4-chlorophenyl)-N-[(thiophen-2-yl)methyl]thieno[3,2-d]pyrimidin-4-amine;

6-[(2S)-2-aminobutyl]-2-chloro-7-methyl-N-[(pyrimidin-4-yl)methyl]thieno[3,2-d]pyrimidin-4-amine;

6-[(2S)-2-aminopropyl]-2-chloro-N-[(3-fluorothiophen-2-yl)methyl]-7-methylthieno[3,2-d]pyrimidin-4-amine;

6-[(2S)-2-aminobutyl]-2-chloro-N-[(3-fluorothiophen-2-yl)methyl]-7-methylthieno[3,2-d]pyrimidin-4-amine;

6-[(2S)-2-aminopropyl]-2-chloro-N-[(4-fluoro-1,3-thiazol-2-yl)methyl]-7-methylthieno[3,2-d]pyrimidin-4-amine;

6-[(2S)-2-aminopropyl]-2-chloro-N-[(5-fluoro-1,3-thiazol-2-yl)methyl]-7-methylthieno[3,2-d]pyrimidin-4-amine;

6-[(1R)-1-aminoethyl]-2-chloro-N-[(furan-2-yl)methyl]-7-methylthieno[3,2-d]pyrimidin-4-amine;

2-chloro-N-[(pyrimidin-4-yl)methyl]thieno[3,2-d]pyrimidin-4-amine;

2-chloro-N-[(1,3-thiazol-2-yl)methyl]thieno[3,2-d]pyrimidin-4-amine;

(3S)-3-amino-4-(2-chloro-4-{[(furan-2-yl)methyl]amino}-7-methylthieno[3,2-d]pyrimidin-6-yl)butan-1-ol;

6-[(2S)-2-aminopropyl]-2-chloro-N-[(5-fluoropyrimidin-4-yl)methyl]-7-methylthieno[3,2-d]pyrimidin-4-amine, and (2R)-2-amino-3-(2-chloro-7-methoxy-4-{[(thiophen-2-yl)methyl]amino}thieno[3,2-d]pyrimidin-6-yl)propan-1-ol; and wherein the form of the compound is selected from the group consisting of a salt, hydrate, solvate, and tautomer form thereof.

11. The method of claim 10, wherein the compound is selected from the group consisting of;

6-[(2R)-2-amino-3-methylbutyl]-2-chloro-N-[(furan-2-yl)methyl]thieno[3,2-d]pyrimidin-4-amine;

6-[(2S)-2-aminopropyl]-2-chloro-N-[(furan-2-yl)methyl]-7-methylthieno[3,2-d]pyrimidin-4-amine;

6-[(2S)-2-aminopropyl]-N-[(furan-2-yl)methyl]-2,7-dimethylthieno[3,2-d]pyrimidin-4-amine;

6-[(2S)-2-aminopropyl]-2-chloro-7-methyl-N-[(5-methylfuran-2-yl)methyl]thieno[3,2-d]pyrimidin-4-amine;

6-[(2S)-2-aminopropyl]-2-chloro-7-methyl-N-[(thiophen-2-yl)methyl]thieno[3,2-d]pyrimidin-4-amine;

6-[(2S)-2-aminopropyl]-2-chloro-7-methyl-N-[(1,3-thiazol-2-yl)methyl]thieno[3,2-d]pyrimidin-4-amine;

6-[(2S)-2-aminopropyl]-2-chloro-7-methyl-N-[(3-methylfuran-2-yl)methyl]thieno[3,2-d]pyrimidin-4-amine;

6-[(2S)-2-aminopropyl]-2-chloro-7-methyl-N-[(5-methyl-1,3-thiazol-2-yl)methyl]thieno[3,2-d]pyrimidin-4-amine;

6-[(2S)-2-aminopropyl]-2-chloro-V-[(5-fluorothiophen-2-yl)methyl]-7-methylthieno[3,2-d]pyrimidin-4-amine;

6-[(2S)-2-aminopropyl]-2-chloro-N-[(3-fluoropyridin-4-yl)methyl]-7-methylthieno[3,2-d]pyrimidin-4-amine;

6-[(2S)-2-aminopropyl]-2-bromo-N-[(furan-2-yl)methyl]-7-methylthieno[3,2-d]pyrimidin-4-amine;

6-[(2S)-2-aminopropyl]-2-chloro-7-methyl-N-[(1,2-oxazol-5-yl)methyl]thieno[3,2-d]pyrimidin-4-amine;

6-[(2S)-2-aminopropyl]-7-bromo-2-chloro-N-[(furan-2-yl)methyl]thieno[3,2-d]pyrimidin-4-amine;

6-[(2S)-2-amino-4-fluorobutyl]-2-chloro-N-[(furan-2-yl)methyl]-7-methylthieno[3,2-d]pyrimidin-4-amine;

(4S)-4-[(2-chloro-4-{[(furan-2-yl)methyl]amino}-7-methylthieno[3,2-d]pyrimidin-6-yl)methyl]-1,3-oxazinan-2-one;

6-[(2S)-2-aminopropyl]-2-chloro-7-methyl-N-[(pyrimidin-2-yl))methyl]thieno[3,2-d]pyrimidin-4-amine;

(2R)-2-amino-3-(2-chloro-7-methyl-4-{[(thiophen-2-yl)methyl]amino}thieno[3,2-d]pyrimidin-6-yl)propan-1-ol;

6-[(2S)-2-aminopropyl]-2-chloro-V-[(3-fluoropyridin-2-yl)methyl]-7-methylthieno[3,2-d]pyrimidin-4-amine;

6-[(2S)-2-aminopropyl]-2-chloro-N-[(2-fluoropyridin-3-yl)methyl]-7-methylthieno[3,2-d]pyrimidin-4-amine;

6-[(2S)-2-aminobutyl]-2-chloro-7-methyl-N-[(1,2-thiazol-5-yl)methyl]thieno[3,2-d]pyrimidin-4-amine;

6-[(2S)-2-aminopropyl]-2-chloro-N-[(3,5-difluoropyridin-4-yl)methyl]-7-methylthieno[3,2-d]pyrimidin-4-amine;

6-[(2S)-2-aminopropyl]-7-bromo-2-chloro-N-[(3-fluoropyridin-4-yl)methyl]thieno[3,2-d]pyrimidin-4-amine;

6-[(2S)-3-amino-2-methylpropyl]-2-chloro-N-[(furan-2-yl)methyl]-7-methylthieno[3,2-d]pyrimidin-4-amine;

6-[(2R)-3-amino-2-methylpropyl]-2-chloro-N-[(furan-2-yl)methyl]-7-methylthieno[3,2-d]pyrimidin-4-amine;

6-[(2S)-2-aminopropyl]-2-chloro-7-methyl-N-[(1,3-thiazol-5-yl)methyl]thieno[3,2-d]pyrimidin-4-amine;

6-[(2S)-2-aminopropyl]-2-chloro-7-methyl-N-[(1,3-oxazol-5-yl)methyl]thieno[3,2-d]pyrimidin-4-amine;

6-[(2S)-2-aminopropyl]-2-chloro-7-ethyl-N-[(furan-2-yl)methyl]thieno[3,2-d]pyrimidin-4-amine;

2-chloro-6-[(2S)-2-(cyclobutylamino)propyl]-N-[(furan-2-yl)methyl]-7-methylthieno[3,2-d]pyrimidin-4-amine;

6-[(2S)-2-aminopropyl]-7-bromo-2-chloro-N-[(thiophen-2-yl)methyl]thieno[3,2-d]pyrimidin-4-amine;

6-[(2S)-2-aminopropyl]-2-chloro-7-cyclopropyl-N-[(thiophen-2-yl)methyl]thieno[3,2-d]pyrimidin-4-amine;

6-[(2S)-2-aminopropyl]-2-chloro-N-[(3-fluorothiophen-2-yl)methyl]-7-methylthieno[3,2-d]pyrimidin-4-amine;

6-[(2S)-2-aminopropyl]-2-chloro-N-[(4-fluoro-1,3-thiazol-2-yl)methyl]-7-methylthieno[3,2-d]pyrimidin-4-amine;

6-[(2S)-2-aminopropyl]-2-chloro-N-[(5-fluoro-1,3-thiazol-2-yl)methyl]-7-methylthieno[3,2-d]pyrimidin-4-amine; and (3S)-3-amino-4-(2-chloro-4-{[(furan-2-yl)methyl]amino}-7-methylthieno[3,2-d]pyrimidin-6-yl)butan-1-ol; and wherein the form of the compound is selected from the group consisting of a salt, hydrate, solvate, and tautomer form thereof.

12. A method for inhibiting or ameliorating spinocerebellar ataxia type 3 (SCA3) in a subject in need thereof, comprising administering to said subject an effective amount of a compound salt or form thereof wherein the compound salt is selected from the group consisting of;

6-[(2S)-2-aminopropyl]-2-chloro-N-[(furan-2-yl)methyl]thieno[3,2-d]pyrimidin-4-amine dihydrochloride;

6-[(2S)-2-aminobutyl]-2-chloro-N-[(furan-2-yl)methyl]thieno[3,2-d]pyrimidin-4-amine dihydrochloride;

6-[(2R)-2-amino-3-methylbutyl]-2-chloro-N-[(furan-2-yl)methyl]thieno[3,2-d]pyrimidin-4-amine dihydrochloride;

6-[(2R,3S)-2-amino-3-methylpentyl]-2-chloro-N-[(furan-2-yl)methyl]thieno[3,2-d]pyrimidin-4-amine dihydrochloride;

6-[(2R)-2-amino-3,3-dimethylbutyl]-2-chloro-N-[(furan-2-yl)methyl]thieno[3,2-d]pyrimidin-4-amine dihydrochloride;

6-[(2S)-2-aminopropyl]-N-[(furan-2-yl)methyl]thieno[3,2-d]pyrimidin-4-amine dihydrochloride;

6-[(2S)-2-aminopropyl]-2-chloro-N-[(pyridin-4-yl)methyl]thieno[3,2-d]pyrimidin-4-amine dihydrochloride;

6-[(2S)-2-aminobutyl]-2-chloro-N-[(thiophen-2-yl)methyl]thieno[3,2-d]pyrimidin-4-amine dihydrochloride;

6-[(2S)-2-aminopropyl]-N-[(pyridin-4-yl)methyl]thieno[3,2-d]pyrimidin-4-amine dihydrochloride;

6-[(2S)-2-aminopropyl]-2-chloro-N-[(furan-2-yl)methyl]-7-methylthieno[3,2-d]pyrimidin-4-amine dihydrochloride;

6-[(2S)-2-aminobutyl]-2-chloro-N-[(furan-2-yl)methyl]-7-methylthieno[3,2-d]pyrimidin-4-amine dihydrochloride;

6-[(2S)-2-aminopropyl]-2-chloro-N-[(thiophen-2-yl)methyl]thieno[3,2-d]pyrimidin-4-amine dihydrochloride;

6-[(2S)-2-aminopropyl]-N-[(furan-2-yl)methyl]-2,7-dimethylthieno[3,2-d]pyrimidin-4-amine dihydrochloride;

6-[(2S)-2-aminopropyl]-2-ethyl-N-[(furan-2-yl)methyl]-7-methylthieno[3,2-d]pyrimidin-4-amine dihydrochloride;

6-[(2S)-2-aminopropyl]-2-cyclopropyl-N-[(furan-2-yl)methyl]-7-methylthieno[3,2-d]pyrimidin-4-amine dihydrochloride;

2-chloro-N-[(furan-2-yl)methyl]-7-methylthieno[3,2-d]pyrimidin-4-amine hydrochloride;

(2R)-2-amino-3-(2-chloro-4-{[(furan-2-yl)methyl]amino}-7-methylthieno[3,2-d]pyrimidin-6-yl)propan-1-ol dihydrochloride;

6-[(2S)-2-aminopropyl]-4-{[(furan-2-yl)methyl]amino}-7-methylthieno[3,2-d]pyrimidine-2-carboxamide trifluoroacetate;

6-[(2S)-2-aminopropyl]-4-{[(furan-2-yl)methyl]amino}-7-methylthieno[3,2-d]pyrimidine-2-carbonitrile trifluoroacetate;

6-[(2S)-2-aminopropyl]-2-chloro-7-methyl-N-[(5-methylfuran-2-yl)methyl]thieno[3,2-d]pyrimidin-4-amine dihydrochloride;

6-[(2S)-2-aminopropyl]-N-[(furan-2-yl)methyl]-7-methyl-2-(trifluoromethyl)thieno[3,2-d]pyrimidin-4-amine dihydrochloride;

6-[(2S)-2-aminopropyl]-2-chloro-7-methyl-N-1[(4-methyl-1,3-thiazol-2-yl)methyl]thieno[3,2-d]pyrimidin-4-amine dihydrochloride;

6-[(2S)-2-aminopropyl]-2-chloro-7-methyl-N-[(thiophen-2-yl)methyl]thieno[3,2-d]pyrimidin-4-amine dihydrochloride;

6-[(2S)-2-aminopropyl]-2-chloro-7-methyl-N-[(1,3-thiazol-2-yl)methyl]thieno[3,2-d]pyrimidin-4-amine trifluoroacetate;

6-[(2S)-2-aminopropyl]-2-chloro-7-methyl-N-1[(3-methylfuran-2-yl)methyl]thieno[3,2-d]pyrimidin-4-amine dihydrochloride;

6-[(2S)-2-aminopropyl]-2-chloro-7-methyl-N-[(5-methyl-1,3-thiazol-2-yl)methyl]thieno[3,2-d]pyrimidin-4-amine dihydrochloride;

6-[(2S)-2-aminopropyl]-2-chloro-7-methyl-N-[(pyrazin-2-yl)methyl]thieno[3,2-d]pyrimidin-4-amine dihydrochloride;

6-[(2S)-2-aminopropyl]-2-chloro-N-[(5-fluorothiophen-2-yl)methyl]-7-methylthieno[3,2-d]pyrimidin-4-amine dihydrochloride;

6-[(2S)-2-aminopropyl]-N-benzyl-2-chloro-7-methylthieno[3,2-d]pyrimidin-4-amine dihydrochloride;

6-[(2S)-2-aminopropyl]-2-chloro-N-[(3-fluoropyridin-4-yl)methyl]-7-methylthieno[3,2-d]pyrimidin-4-amine dihydrochloride;

6-[(2S)-2-aminopropyl]-2-chloro-7-cyclopropyl-N-[(furan-2-yl)methyl]thieno[3,2-d]pyrimidin-4-anine trifluoroacetate;
6-[(2S)-2-aminobutyl]-2-chloro-7-methyl-N-[(thiophen-2-yl)methyl]thieno[3,2-d]pyrimidin-4-amine dihydrochloride;
6-[(2S)-2-aminopropyl]-2-bromo-N-[(furan-2-yl)methyl]-7-methylthieno[3,2-d]pyrimidin-4-amine trifluoroacetate;
6-[(2S)-2-aminopropyl]-2-chloro-7-methyl-N-[(1,2-oxazol-5-yl)methyl]thieno[3,2-d]pyrimidin-4-amine hydrochloride;
6-[(2S)-2-aminopropyl]-7-bromo-2-chloro-N-[(furan-2-yl)methyl]thieno[3,2-d]pyrimidin-4-amine dihydrochloride;
6-(azetidin-3-yl)-2-chloro-N-[(furan-2-yl)methyl]-7-methylthieno[3,2-d]pyrimidin-4-amine trifluoroacetate;
6-[(2S)-2-aminopropyl]-2-chloro-N-[(2-fluorophenyl)methyl]-7-methylthieno[3,2-d]pyrimidin-4-amine dihydrochloride;
6-[(2S)-2-aminopropyl]-2-chloro-7-methyl-N-[(pyridin-4-yl)methyl]thieno[3,2-d]pyrimidin-4-amine dihydrochloride;
6-[(1S)-1-aminoethyl]-7-bromo-2-chloro-N-[(furan-2-yl)methyl]thieno[3,2-d]pyrimidin-4-amine hydrochloride;
6-[(1S)-1-aminoethyl]-2-chloro-N-[(furan-2-yl)methyl]-7-methylthieno[3,2-d]pyrimidin-4-amine hydrochloride;
6-[(1S)-1-aminopropyl]-2-chloro-N-[(furan-2-yl)methyl]-7-methylthieno[3,2-d]pyrimidin-4-amine hydrochloride;
6-[(1R)-1-aminopropyl]-2-chloro-N-[(furan-2-yl)methyl]-7-methylthieno[3,2-d]pyrimidin-4-amine hydrochloride;
6-[(2S)-2-aminopropyl]-2-chloro-7-methyl-N-[(pyrimidin-4-yl)methyl]thieno[3,2-d]pyrimidin-4-amine dihydrochloride;
6-[(2S)-2-amino-4-fluorobutyl]-2-chloro-N-[(furan-2-yl)methyl]-7-methylthieno[3,2-d]pyrimidin-4-amine dihydrochloride;
6-[(2S)-2-aminobutyl]-2-chloro-N-[(3-fluoropyridin-4-yl)methyl]-7-methylthieno[3,2-d]pyrimidin-4-amine dihydrochloride;
6-[(2S)-2-aminobutyl]-2-chloro-7-methyl-N-[(1,3-thiazol-2-yl)methyl]thieno[3,2-d]pyrimidin-4-amine dihydrochloride;
6-[(2S)-2-aminopropyl]-2-chloro-7-methyl-N-[(pyrimidin-2-yl)methyl]thieno[3,2-d]pyrimidin-4-amine dihydrochloride;
(2R)-2-amino-3-(2-chloro-7-methyl-4-{[(thiophen-2-yl)methyl]amino}thieno[3,2-d]pyrimidin-6-yl)propan-1-ol dihydrochloride;
2-chloro-N-[(furan-2-yl)methyl]-7-methyl-6-(pyrrolidin-3-yl)thieno[3,2-d]pyrimidin-4-amine formate;
6-[(1S)-1-aminoethyl]-2-chloro-N-[(furan-2-yl)methyl]-7-phenylthieno[3,2-d]pyrimidin-4-amine formate;
6-[(2S)-2-aminopropyl]-2-chloro-N-[(3-fluoropyridin-2-yl)methyl]-7-methylthieno[3,2-d]pyrimidin-4-amine dihydrochloride;
6-[(2S)-2-aminopropyl]-2-chloro-N-[(2-fluoropyridin-3-yl)methyl]-7-methylthieno[3,2-d]pyrimidin-4-amine dihydrochloride;
6-[(1S)-1-aminoethyl]-N-[(furan-2-yl)methyl]-2,7-diphenylthieno[3,2-d]pyrimidin-4-amine formate;
6-[(2S)-2-aminobutyl]-2-chloro-7-methyl-N-[(1,2-thiazol-5-yl)methyl]thieno[3,2-d]pyrimidin-4-amine formate;
6-[(2S)-2-aminopropyl]-2-chloro-N-[(3,5-difluoropyridin-4-yl)methyl]-7-methylthieno[3,2-d]pyrimidin-4-amine dihydrochloride;
6-[(2S)-2-aminopropyl]-2-chloro-N-[(furan-2-yl)methyl]-7-(4-methoxyphenyl)thieno[3,2-d]pyrimidin-4-amine formate;
6-(3-aminopropyl)-2-chloro-N-[(furan-2-yl)methyl]-7-methylthieno[3,2-d]pyrimidin-4-amine hydrochloride;
6-[(2S)-2-aminopropyl]-7-bromo-2-chloro-N-[(3-fluoropyridin-4-yl)methyl]thieno[3,2-d]pyrimidin-4-amine dihydrochloride;
6-[(2S)-2-aminobutyl]-2-chloro-7-methyl-N-[(1,3-oxazol-2-yl)methyl]thieno[3,2-d]pyrimidin-4-amine dihydrochloride;
6-[(2S)-3-amino-2-methylpropyl]-2-chloro-N-[(furan-2-yl)methyl]-7-methylthieno[3,2-d]pyrimidin-4-amine hydrochloride;
6-[(2R)-3-amino-2-methylpropyl]-2-chloro-N-[(furan-2-yl)methyl]-7-methylthieno[3,2-d]pyrimidin-4-amine hydrochloride;
6-[(2S)-2-aminopropyl]-2-chloro-N-[(1H-imidazol-2-yl)methyl]-7-methylthieno[3,2-d]pyrimidin-4-amine dihydrochloride;
6-[(2S)-2-aminopropyl]-2-chloro-7-methyl-N-[(1,3-thiazol-5-yl)methyl]thieno[3,2-d]pyrimidin-4-amine dihydrochloride;
6-[(2S)-2-aminopropyl]-2-chloro-7-methyl-V-[(1,3-oxazol-5-yl)methyl]thieno[3,2-d]pyrimidin-4-amine dihydrochloride;
6-[(2R)-2-amino-3-methoxypropyl]-2-chloro-N-[(furan-2-yl)methyl]-7-methylthieno[3,2-d]pyrimidin-4-amine dihydrochloride;
6-[(2S)-2-aminopropyl]-2-chloro-7-ethyl-N-[(furan-2-yl)methyl]thieno[3,2-d]pyrimidin-4-amine hydrochloride;
2-chloro-6-[(2S)-2-(cyclobutylamino)propyl]-N-[(furan-2-yl)methyl]-7-methylthieno[3,2-d]pyrimidin-4-amine formate;
2-chloro-N-[(furan-2-yl)methyl]-7-methyl-6-[(2S)-2-(methylamino)propyl]thieno[3,2-d]pyrimidin-4-amine hydrochloride;
6-[(2S)-2-aminopropyl]-2-chloro-7-methyl-N-[(1-methyl-1H-pyrazol-5-yl)methyl]thieno[3,2-d]pyrimidin-4-amine hydrochloride;
6-[(2S)-2-aminopropyl]-7-bromo-2-chloro-N-[(thiophen-2-yl)methyl]thieno[3,2-d]pyrimidin-4-amine hydrochloride;
6-[(2S)-2-aminopropyl]-7-bromo-4-{[(thiophen-2-yl)methyl]amino}thieno[3,2-d]pyrimidine-2-carbonitrile formate;
6-[(2S)-2-aminopropyl]-4-{[(thiophen-2-yl)methyl]amino}thieno[3,2-d]pyrimidine-2,7-dicarbonitrile hydrochloride;
6-[(2S)-2-aminopropyl]-2-chloro-7-cyclopropyl-N-[(thiophen-2-yl)methyl]thieno[3,2-d]pyrimidin-4-amine formate;
6-[(2S)-2-aminopropyl]-2-chloro-7-phenyl-N-[(thiophen-2-yl)methyl]thieno[3,2-d]pyrimidin-4-amine hydrochloride;
6-[(2S)-2-aminopropyl]-2-chloro-7-(4-chlorophenyl)-N-[(thiophen-2-yl)methyl]thieno[3,2-d]pyrimidin-4-amine hydrochloride;
6-[(2S)-2-aminobutyl]-2-chloro-7-methyl-N-[(pyrimidin-4-yl)methyl]thieno[3,2-d]pyrimidin-4-amine dihydrochloride;

6-[(2S)-2-aminopropyl]-2-chloro-N-[(3-fluorothiophen-2-yl)methyl]-7-methylthieno[3,2-d]pyrimidin-4-amine dihydrochloride;

6-[(2S)-2-aminobutyl]-2-chloro-N-[(3-fluorothiophen-2-yl)methyl]-7-methylthieno[3,2-d]pyrimidin-4-amine dihydrochloride;

6-[(2S)-2-aminopropyl]-2-chloro-N-[(4-fluoro-1,3-thiazol-2-yl)methyl]-7-methylthieno[3,2-d]pyrimidin-4-amine dihydrochloride;

6-[(2S)-2-aminopropyl]-2-chloro-N-[(5-fluoro-1,3-thiazol-2-yl)methyl]-7-methylthieno[3,2-d]pyrimidin-4-amine dihydrochloride;

6-[(1R)-1-aminoethyl]-2-chloro-N-[(furan-2-yl)methyl]-7-methylthieno[3,2-d]pyrimidin-4-amine hydrochloride;

(3S)-3-amino-4-(2-chloro-4-{[(furan-2-yl)methyl]amino}-7-methylthieno[3,2-d]pyrimidin-6-yl)butan-1-ol dihydrochloride;

6-[(2S)-2-aminopropyl]-2-chloro-N-[(5-fluoropyrimidin-4-yl)methyl]-7-methylthieno[3,2-d]pyrimidin-4-amine formate, and (2R)-2-amino-3-(2-chloro-7-methoxy-4-{[(thiophen-2-yl)methyl]amino}thieno[3,2-d]pyrimidin-6-yl)propan-1-ol dihydrochloride; and wherein the form of the compound salt is selected from the group consisting of a hydrate, solvate, and tautomer form thereof.

13. The method of claim 12, wherein the compound salt is selected from the group consisting of;

6-[(2R)-2-amino-3-methylbutyl]-2-chloro-N-[(furan-2-yl)methyl]thieno[3,2-d]pyrimidin-4-amine dihydrochloride;

6-[(2S)-2-aminopropyl]-2-chloro-N-[(furan-2-yl)methyl]-7-methylthieno[3,2-d]pyrimidin-4-amine dihydrochloride;

6-[(2S)-2-aminopropyl]-N-[(furan-2-yl)methyl]-2,7-dimethylthieno[3,2-d]pyrimidin-4-amine dihydrochloride;

6-[(2S)-2-aminopropyl]-2-chloro-7-methyl-N-[(5-methylfuran-2-yl)methyl]thieno[3,2-d]pyrimidin-4-amine dihydrochloride;

6-[(2S)-2-aminopropyl]-2-chloro-7-methyl-N-[(thiophen-2-yl)methyl]thieno[3,2-d]pyrimidin-4-amine dihydrochloride;

6-[(2S)-2-aminopropyl]-2-chloro-7-methyl-N-[(1,3-thiazol-2-yl)methyl]thieno[3,2-d]pyrimidin-4-amine trifluoroacetate;

6-[(2S)-2-aminopropyl]-2-chloro-7-methyl-N-[(3-methylfuran-2-yl)methyl]thieno[3,2-d]pyrimidin-4-amine dihydrochloride;

6-[(2S)-2-aminopropyl]-2-chloro-7-methyl-N-1[(5-methyl-1,3-thiazol-2-yl)methyl]thieno[3,2-d]pyrimidin-4-amine dihydrochloride;

6-[(2S)-2-aminopropyl]-2-chloro-N-[(5-fluorothiophen-2-yl)methyl]-7-methylthieno[3,2-d]pyrimidin-4-amine dihydrochloride;

6-[(2S)-2-aminopropyl]-2-chloro-N-[(3-fluoropyridin-4-yl)methyl]-7-methylthieno[3,2-d]pyrimidin-4-amine dihydrochloride;

6-[(2S)-2-aminopropyl]-2-bromo-N-[(furan-2-yl)methyl]-7-methylthieno[3,2-d]pyrimidin-4-amine trifluoroacetate;

6-[(2S)-2-aminopropyl]-2-chloro-7-methyl-N-[(1,2-oxazol-5-yl)methyl]thieno[3,2-d]pyrimidin-4-amine hydrochloride;

6-[(2S)-2-aminopropyl]-7-bromo-2-chloro-N-[(furan-2-yl)methyl]thieno[3,2-d]pyrimidin-4-amine dihydrochloride;

6-[(2S)-2-amino-4-fluorobutyl]-2-chloro-N-[(furan-2-yl)methyl]-7-methylthieno[3,2-d]pyrimidin-4-amine dihydrochloride;

6-[(2S)-2-aminopropyl]-2-chloro-7-methyl-N-[(pyrimidin-2-yl)methyl]thieno[3,2-d]pyrimidin-4-amine dihydrochloride:

(2R)-2-amino-3-(2-chloro-7-methyl-4-{[(thiophen-2-yl)methyl]amino}thieno[3,2-d]pyrimidin-6-yl)propan-1-ol dihydrochloride;

6-[(2S)-2-aminopropyl]-2-chloro-N-[(3-fluoropyridin-2-yl)methyl]-7-methylthieno[3,2-d]pyrimidin-4-anine dihydrochloride;

6-[(2S)-2-aminopropyl]-2-chloro-N-[(2-fluoropyridin-3-yl)methyl]-7-methylthieno[3,2-d]pyrimidin-4-amine dihydrochloride;

6-[(2S)-2-aminobutyl]-2-chloro-7-methyl-N-[(1,2-thiazol-5-yl)methyl]thieno[3,2-d]pyrimidin-4-amine formate;

6-[(2S)-2-aminopropyl]-2-chloro-N-[(3,5-difluoropyridin-4-yl)methyl]-7-methylthieno[3,2-d]pyrimidin-4-amine dihydrochloride;

6-[(2S)-2-aminopropyl]-7-bromo-2-chloro-N-[(3-fluoropyridin-4-yl)methyl]thieno[3,2-d]pyrimidin-4-amine dihydrochloride;

6-[(2S)-3-amino-2-methylpropyl]-2-chloro-N-[(furan-2-yl)methyl]-7-methylthieno[3,2-d]pyrimidin-4-amine hydrochloride;

6-[(2R)-3-amino-2-methylpropyl]-2-chloro-N-[(furan-2-yl)methyl]-7-methylthieno[3,2-d]pyrimidin-4-amine hydrochloride;

6-[(2S)-2-aminopropyl]-2-chloro-7-methyl-N-[(1,3-thiazol-5-yl)methyl]thieno[3,2-d]pyrimidin-4-amine dihydrochloride;

6-[(2S)-2-aminopropyl]-2-chloro-7-methyl-N-[(1,3-oxazol-5-yl)methyl]thieno[3,2-d]pyrimidin-4-amine dihydrochloride;

6-[(2S)-2-aminopropyl]-2-chloro-7-ethyl-N-[(furan-2-yl)methyl]thieno[3,2-d]pyrimidin-4-amine hydrochloride;

2-chloro-6-[(2S)-2-(cyclobutylamino)propyl]-N-[(furan-2-yl)methyl]-7-methylthieno[3,2-d]pyrimidin-4-amine formate;

6-[(2S)-2-aminopropyl]-7-bromo-2-chloro-N-[(thiophen-2-yl)methyl]thieno[3,2-d]pyrimidin-4-amine hydrochloride;

6-[(2S)-2-aminopropyl]-2-chloro-7-cyclopropyl-N-[(thiophen-2-yl)methyl]thieno[3,2-d]pyrimidin-4-amine formate;

6-[(2S)-2-aminopropyl]-2-chloro-N-[(3-fluorothiophen-2-yl)methyl]-7-methylthieno[3,2-d]pyrimidin-4-amine dihydrochloride;

6-[(2S)-2-aminopropyl]-2-chloro-N-[(4-fluoro-1,3-thiazol-2-yl)methyl]-7-methylthieno[3,2-d]pyrimidin-4-amine dihydrochloride;

6-[(2S)-2-aminopropyl]-2-chloro-N-[(5-fluoro-1,3-thiazol-2-yl)methyl]-7-methylthieno[3,2-d]pyrimidin-4-amine dihydrochloride; and (3S)-3-amino-4-(2-chloro-4-{[(furan-2-yl)methyl]amino}-7-methylthieno[3,2-d]pyrimidin-6-yl)butan-1-ol dihydrochloride; and wherein the form of the compound salt is selected from the group consisting of a hydrate, solvate, and tautomer form thereof.

14. The method of any one of claims 1 or 10-13, wherein the effective amount of the compound or form thereof or the effective amount of the compound salt or form thereof induces exon skipping in ATXN3 pre-mRNA in the subject.

15. The method of any one of claims 1 or 10-13, wherein the effective amount of the compound or form thereof or the effective amount of the compound salt or form thereof induces exon skipping.

16. The method of any one of claims 1 or 10-13, wherein the effective amount of the compound or form thereof or the effective amount of the compound salt or form thereof is in an admixture with one or more pharmaceutically acceptable excipient(s).

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Homo sapiens

<400> SEQUENCE: 1

caacggattt ggtcgtattg g                                   21


<210> SEQ ID NO 2
<211> LENGTH: 25
<212> TYPE: DNA
<213> ORGANISM: Homo sapiens

<400> SEQUENCE: 2

tgatggcaac aatatccact ttacc                               25


<210> SEQ ID NO 3
<211> LENGTH: 21
<212> TYPE: DNA
<213> ORGANISM: Homo sapiens

<400> SEQUENCE: 3

cgcctggtca ccagggctgc t                                   21
```